(12) United States Patent
Hancock

(10) Patent No.: US 9,675,716 B2
(45) Date of Patent: Jun. 13, 2017

(54) MICROWAVE PLASMA STERILISATION SYSTEM AND APPLICATORS THEREFOR

(71) Applicant: CREO MEDICAL LIMITED, Gwent, Wales (GB)

(72) Inventor: Christopher Paul Hancock, Bristol (GB)

(73) Assignee: Creo Medical Limited, Chepstow (GB)

( * ) Notice: Subject to any disclaimer, the term of this patent is extended or adjusted under 35 U.S.C. 154(b) by 206 days.

(21) Appl. No.: 14/526,208

(22) Filed: Oct. 28, 2014

(65) Prior Publication Data

US 2015/0056107 A1 Feb. 26, 2015

Related U.S. Application Data

(60) Continuation of application No. 14/072,422, filed on Nov. 5, 2013, now Pat. No. 8,900,521, which is a (Continued)

(30) Foreign Application Priority Data

Nov. 6, 2007 (GB) .................................. 0721714.4
Mar. 15, 2008 (GB) .................................. 0804885.2

(Continued)

(51) Int. Cl.
*A61L 2/02* (2006.01)
*A61L 2/14* (2006.01)
(Continued)

(52) U.S. Cl.
CPC .............. *A61L 2/02* (2013.01); *A61L 2/0011* (2013.01); *A61L 2/14* (2013.01); *A61L 2/24* (2013.01);
(Continued)

(58) Field of Classification Search
None
See application file for complete search history.

(56) References Cited

U.S. PATENT DOCUMENTS

| 4,207,286 A | 6/1980 | Boucher |
| 6,340,863 B1 | 1/2002 | Ikeda et al. |

(Continued)

FOREIGN PATENT DOCUMENTS

| EP | 1 765 044 A | 3/2007 |
| WO | WO 2006/014862 A | 2/2006 |

*Primary Examiner* — Kishor Mayekar

(74) *Attorney, Agent, or Firm* — Arent Fox LLP

(57) ABSTRACT

A sterilization system having a controllable non-ionizing microwave radiation source for providing microwave energy for combining with a gas to produce atmospheric low temperature plasma for sterilizing biological tissue surfaces or the like. A plasma generating region may be contained in a hand held plasma applicator. The system may include an impedance adjustor e.g. integrated in the plasma applicator arranged to set a plasma strike condition and plasma sustain condition. The gas and microwave energy may be transported to a plasma generating region along an integrated cable assembly. The integrated cable assembly may provide a two way gas flow arrangement to permit residual gas to be removed from the surface. Invasive surface plasma treatment is therefore possible. The plasma applicator may have multiple plasma emitters to produce a line or blanket of plasma.

11 Claims, 27 Drawing Sheets

Related U.S. Application Data division of application No. 12/741,517, filed as application No. PCT/GB2008/003763 on Nov. 6, 2008, now Pat. No. 8,647,585.

(30) Foreign Application Priority Data

Apr. 23, 2008 (GB) .................................. 0807347.0
Oct. 17, 2008 (GB) .................................. 0819030.8

(51) Int. Cl.
*A61L 2/24* (2006.01)
*H05H 1/46* (2006.01)
*A61L 2/00* (2006.01)

(52) U.S. Cl.
CPC ......... *H05H 1/46* (2013.01); *H05H 2001/463* (2013.01); *H05H 2001/4682* (2013.01); *H05H 2240/10* (2013.01); *H05H 2240/20* (2013.01)

(56) References Cited

U.S. PATENT DOCUMENTS

| | | |
|---|---|---|
| 6,969,487 B1 | 11/2005 | Sias et al. |
| 8,647,585 B2 * | 2/2014 | Hancock .................. A61L 2/14 422/186 |
| 8,900,521 B2 * | 12/2014 | Hancock .................. A61L 2/14 422/186 |
| 2002/0127155 A1 | 9/2002 | Minaee et al. |
| 2005/0269199 A1 | 12/2005 | Pollak et al. |
| 2007/0193517 A1 | 8/2007 | Matsuuchi et al. |
| 2007/0290620 A1 * | 12/2007 | Lee ......................... H05H 1/24 315/111.21 |

* cited by examiner

MICROWAVE PLASMA STERILISATION SYSTEM AND APPLICATORS THEREFOR

CROSS-REFERENCE TO RELATED APPLICATIONS

This application is a Continuation Application of U.S. patent application Ser. No. 14/072,422, filed Nov. 5, 2013; which is a Divisional Application of U.S. patent application Ser. No. 12/741,517, filed Aug. 3, 2010; which in turn is a National Stage Entry of International Application No. PCT/GB2008/003763, filed Nov. 6, 2008; which claims priority to British Patent Application Nos. 0721714.4, filed Nov. 6, 2007, 0804885.2, filed Mar. 5, 2008, 0807347.0, filed Apr. 23, 2008, and 0819030.8, filed Oct. 17, 2008. The disclosures of each of the prior applications are hereby incorporated in their entirety by reference.

FIELD OF THE INVENTION

The invention relates to sterilisation systems suitable for clinical use, e.g. on or in the human or animal body. For example, the invention may provide a system that can be used to destroy or treat certain bacteria and/or viruses associated with the human or animal biological system and/or the surrounding environment. In particular the invention may be suitable for the sterilisation of wound and wound beds.

BACKGROUND TO THE INVENTION

Bacteria are single-celled organisms that are found almost everywhere, exist in large numbers and are capable of dividing and multiplying rapidly. Most bacteria are harmless, but there are three harmful groups; namely: cocci, spirilla, and bacilla. The cocci bacteria are round cells, the spirilla bacteria are coil-shaped cells, and the bacilli bacteria are rod-shaped. The harmful bacteria cause diseases such as tetanus and typhoid.

Viruses can only live and multiply by taking over other cells, i.e. they cannot survive on their own. Viruses cause diseases such as colds, flue, mumps and AIDS.

Fungal spores and tiny organisms called protozoa can cause illness.

Sterilisation is an act or process that destroys or eliminates all form of life, especially micro-organisms. During the process of plasma sterilisation, active agents are produced. These active agents are high intensity ultraviolet photons and free radicals, which are atoms or assemblies of atoms with chemically unpaired electrons. An attractive feature of plasma sterilisation is that it is possible to achieve sterilisation at relatively low temperatures, such as body temperature. Plasma sterilisation also has the benefit that it is safe to the is operator and the patient.

Low temperature atmospheric pressure plasmas may be used to replace conventional sterilisation methods and offer clear advantage over existing means of sterilisation in terms of their non-toxic nature, instant treatment effects, and the ability to produce the plasma at a range of energy levels and in a range of different forms. In a room temperature environment, plasma is usually supported by electro-magnetic (EM) fields. Light electrons absorb energy from an electric field and transfer part of this energy to heavy particles in the plasma. If electrons are not given sufficient opportunity to transfer their energy, heavier plasma components remain at much lower temperatures than the electrons. Such plasmas are called non-thermal plasma and their gas temperatures can be as low as room temperature.

Active plasma particles (electrons, ions, radicals, and other chemically active species) and UV radiation may be used to disinfect and sterilise living tissue, biological inserts placed inside living tissue, external surfaces, or surgical instruments. The closer the plasma source is located with respect to the living tissue (or other surfaces) and the higher the electric field in the plasma, the higher the intensity and efficacy of the non-thermal plasma sterilisation treatment process.

For practical use inside or on the surface of the body, i.e. for wound sterilisation to kill bacteria within the wound or bacteria that resides on the surface of the wound, the destruction or reduction of bacteria contained within natural orifices inside the body, to kill bacteria contained on inserts placed inside the human body (and that manifested within biological tissue in the vicinity of the insert), or to kill bacteria that may exist on the skin before opening up the patient (and to re-sterilise prior to closure) and other surfaces that are required to be sterilised where it is undesirable for the temperature to rise excessively, i.e. for beds, curtains, instruments, pillows and certain plastics, the temperature at the surface or at the treatment site (the biological tissue or environment) produced by the plasma should not exceed normal human body temperature. It may be desirable to consider the maximum temperature at a surface produced by a plasma jet to be limited to a maximum of 10° C. above room temperature, i.e. $T_r \leq T_t \leq T_r+10$, where $T_r$ is room temperature (° C.), and $T_t$ is the treatment temperature (° C.). A nominal temperature for non-thermal plasma is 37° C.

Although for some applications it is desirable to operate within these boundaries, the invention described herein may not be limited by such. For example, it may be desirable to increase the temperature well above body temperature when considering the sterilisation of hospital floors, hospital beds or other general materials within a hospital environment where temperatures in excess of body temperature can be tolerated.

The length of the plasma and the temperature produced at a surface may be found using the energy balance, i.e. electron-induced heating of heavy particles versus energy losses by thermal conduction. The length of a plasma jet may be calculated as follows:

$$L = \sqrt{\frac{m_i 3 K_i \Delta T}{m_e v_i N_D k T_e}}, \qquad 1$$

where $m_i$ is atomic mass, $K_i$ is thermal conductivity, $v_i$ is effective electron-atom collision frequency, $N_D$ is electron density, $\Delta T$ is temperature change and $T_e$, is energy level. Tables 1 and 2 list the parameters for calculating plasma length in certain gases. Table 3 lists typical plasma lengths at room temperature for those gases.

TABLE 1

Parameters for calculation of plasma length at a temperature of 300 K and pressure of 1 Torr (133.3 Pa), and where u is an atomic mass unit (=1.66 × 10$^{-27}$ kg).

| | Ar | $CO_2$ | He | $N_2$ |
|---|---|---|---|---|
| $K_i$ (Wm$^{-1}$K$^{-1}$) | 16.2 | 14.5 | 146.10 | 24.3 |
| $v_i$ (s$^{-1}$) | 6.3117 × 10$^7$ | 3.22 × 10$^9$ | 2.27 × 10$^8$ | 1.497 × 10$^8$ |
| $m_i$ (kg) | 39.948 u | 44.01 u | 4.002602 u | 14.0067 u |

TABLE 1-continued

Parameters for calculation of plasma length at a temperature of 300 K and pressure of 1 Torr (133.3 Pa), and where u is an atomic mass unit (=1.66 × 10$^{-27}$ kg).

| Ar | CO$_2$ | He | N$_2$ |
| --- | --- | --- | --- |

TABLE 2

Other parameters used in the calculation

| Parameter | Value |
| --- | --- |
| N$_D$ | 3.22 × 10$^{22}$ m$^{-3}$ |
| m$_e$ | 9.109 × 10$^{-31}$ kg |
| k | 1.380622 × 10$^{-23}$ |
| T$_e$ | 3 eV |
| ΔT | 10 K |

TABLE 3

Calculated plasma length at a temperature of 300 K and pressure of 1 Torr (133.3 Pa)

| | Ar | CO$_2$ | He | N$_2$ |
| --- | --- | --- | --- | --- |
| Plasma Length (m) | 5.35 × 10$^{-4}$ | 7.438 × 10$^{-5}$ | 8.478 × 10$^{-4}$ | 4.337 × 10$^{-4}$ |

The non-thermal plasma can be used to create highly reactive molecules called free radicals that can be used to break down contaminants. Free radicals are atoms or molecules that have unpaired electrons.

Non-thermal plasma cells may use a high voltage electric field to create large quantities of highly reactive free radicals. The free radicals may be used to react with and break up hazardous organic chemicals to convert them into non-hazardous substances, such as carbon dioxide or water.

Ultraviolet photons in the plasma affect bacteria cells by inducing the formation of thymine dimers in the DNA. This inhibits the ability of the bacteria to replicate properly. This effect may be particularly useful in the application of treating sexually transmitted diseases where it may be desirable to reduce the level of bacteria, but not totally destroy it, i.e. so as not to destroy the body's natural flora.

It is also recognised that reactive species created in the plasma play an important role in sterilisation. In particular, discharges containing oxygen may have a strong germicidal effect. For example, plasma typically contains charged electrons and ions as well as chemically active species, such as ozone, nitrous oxides, and hydroxyl radicals. As an example of a clinical effect that may be produced using these systems, nitric oxide plasma may be produced using a helium gas and air, whereby the helium helps the plasma to form efficiently from air at low energies; if this plasma could be inserted into the body then it could be used to help fight infection and inflammation—this could be particularly useful for minimally invasive or keyhole applications, e.g. treatment of sexually transmitted diseases or body insert sterilisation. Hydroxyl radicals that may be produced from plasma are another useful source as they are far more effective at oxidizing pollutants in the air than ozone and are several times more germicidal and fungicidal than chlorine, which makes them very interesting in terms of destroying mould, bacteria and viruses.

It has also been suggested that charged particles may play a significant role in rupturing the outer membrane of the bacteria cells. Electrostatic force caused by charge accumulation on the outer surface of the cells' membrane can overcome the tensile strength of the membrane and therefore cause it to rupture. This process is more likely to occur for gram-negative bacteria, which possess irregular surfaces.

SUMMARY OF THE INVENTION

At its most general the invention proposes a sterilisation system having a controllable (e.g. adjustably modulatable) non-ionising microwave radiation source for providing microwave energy for combining with a gas (e.g. an inert gas or a mixture of inert gases) to produce atmospheric plasma. The disclosure presented below contains a number of interrelated aspects. The first aspect relates to the system as a whole and the subsequent aspects relate to various plasma applicators, e.g. plasma generating and directing tools, which take in a gas (or a mixture of gases) and microwave energy and contain a structure that can be used to generate the plasma and may be used with the system to provide particular benefits associated with different modes of use.

The plasma applicators may direct and/or focus the plasma into regions of interest using suitable antenna arrangements that are designed and developed specifically to enable a suitable plume of plasma, or a plurality of plumes, to be created and delivered in such a manner that controlled atmospheric plasma may be produced that is useful for destroying various types of bacteria or viruses or fungi or used for treating viruses or viral infections.

This invention may be used to significantly reduce levels of bacteria without wiping it out completely, e.g. for use in regions of the body where it is necessary for a residual level of bacteria to exist. For other applications, it may be appropriate to arrange the system or equipment in such a manner that enables the bacteria or viruses to be totally destroyed.

The treatment system introduced here uses non-ionising radiation, e.g. generated using a source oscillator to produce a low power microwave frequency signal and a power amplifier (e.g. an arrangement of microwave transistors) to amplify the low power signal to a level that is high enough to enable an electric field to be produced which is required to strike the plasma using a gas found to be suitable for the particular application. Solid state signal amplifiers may be used. The system may also operate in a mode whereby the amplifier is driven into saturation or full power to set up an electric field necessary to strike the plasma and then backed off once it has been struck.

In this specification microwave frequency may be used broadly to indicate the range 400 MHz to 100 GHz, but preferably the range 1 GHz to 60 GHz. Specific frequencies that have been considered are: 900 MHz, 2.45 GHz, 3.3 GHz, 5.2 GHz, 10 GHz, 14.5 GHz and 24 GHz.

Sterilisation System

According to a first aspect of the invention there may be provided plasma sterilisation apparatus comprising: a plasma applicator having an enclosed plasma generating region and an outlet for directing plasma out of the plasma generating region towards a surface to be sterilised; a microwave radiation generator connected to deliver microwave energy into the plasma generating region; and a gas feed connected to deliver gas into the plasma generating region, wherein the apparatus is configured to create a high impedance at the plasma generating region when gas and microwave energy are delivered thereto thereby to strike a non-thermal plasma for delivery out of the applicator, and wherein the microwave radiation generator comprises a controller arranged adjustably to control the microwave energy delivered to the plasma generating region. The apparatus therefore has an inbuilt facility for striking the plasma.

The plasma applicator may be a hand held unit remote from the generator (but connected thereto via a microwave feed line). In that embodiment the plasma is generated remotely and the microwave energy control extends along the feed line. In an alternative arrangement, the plasma applicator may be at the generator and delivered to the region to be sterilised along its own feed pipe. The arrangement may be advantageous because it limits the extent of the apparatus over which microwave control needs to be exerted.

The ability to control the microwave energy can enable a plasma to be generated that is most suitable for any one of a variety of applications of interest. Control of the microwave energy and/or the gas flow rate and/or the gas mixture gives control over the size of the plume and the temperature at the surface of the tissue or material being treated. Furthermore, the system may be arranged to quantify the dosage of plasma energy delivered to the surface to be treated, e.g. biological tissue surface.

The microwave energy may be controlled by any one or more of varying a frequency of the microwave energy in a controlled manner (e.g. controlling the frequency of radiation from the microwave radiation generator), varying the power level in a controlled manner, and modulating the microwave energy in a controlled manner.

The controller may include a microwave signal modulator arranged to modulate the microwave energy delivered to the plasma generating region. The modulation frequency may be contained within the range from 0.1 Hz up to 10 MHz. The duty cycle may be from less than 1% to 100%. In some embodiments, the modulation frequency may be from 10 Hz to 100 KHz and the duty cycle may be between 10% and 25%. In preferred embodiments the modulation frequency may be between 100 Hz and 1 KHz, and the duty cycle may be 20%.

The apparatus may thus be arranged to generate the plasma using pulsed operation. In one embodiment, the plasma may be struck on each pulse (the strike may occur due to a transient produced on one of the edges of the pulse—normally the positive going edge). The operation of the system may be such that it is necessary to keep applying pulses to the system in order to generate the required clinical and biological effects.

A DC field or DC voltage level may be applied to the microwave field in the plasma generating region. In a particular arrangement, a bias 'T' may be used at the input to the plasma applicator or the antenna and the DC voltage applied through an inductor, whereas the microwave field may be applied through a capacitor. In this arrangement, the inductor will pass the DC voltage but block the high frequency microwave signal. The inductive reactance is given by $2\pi fL$ (where f is the frequency of the microwave energy and L is the inductance of the inductor). If the frequency is zero (i.e. DC), and inductance has a finite value, the impedance tends to zero. The capacitor will pass the high frequency microwave signal but block the DC voltage. The capacitive reactance is given by $$\frac{1}{2\pi fC}$$

(where C is the capacitance of the capacitor). If the frequency tends to infinity (e.g. 400 MHz or more) and the capacitance has a finite value, the impedance tends to zero. The DC voltage may be used to initiate or strike the plasma and the microwave field may be used to sustain the plasma. A fixed tuning stub or a plurality of tuning stubs may also be arranged as a band reject filter to replace the inductor and be used to block or stop the high frequency signals getting back into the low frequency or DC generator.

The microwave radiation generator may include an amplifier, e.g. comprising a plurality of solid state transistors or a tube amplifier or a resonant cavity. The controller may include a variable attenuator arranged to control a power level or the pulse width of a microwave signal input to the amplifier. The variable attenuator may have a fast enough response time to operate as the microwave signal modulator mentioned above.

In one embodiment, the controller may include an amplifier signal modulator arranged to modulate an activation signal for the amplifier. This embodiment may thus provide dual modulation, i.e. modulation of both the amplifier input signal and drive signal. This may enable the thermal mass and amplifier cooing requirements, e.g. fans and water cooling requirements, to be reduced by switching off the activation signal when microwave power delivery is not required, e.g. when the input signal is zero or the first modulator (fast switch) is turned off.

An output stage of the amplifier may include a microwave power combiner arrangement arranged to combine the output power from a plurality of power devices to provide a single output power that is the sum of the outputs from each of the power devices.

Conversely, the microwave power from a single high power source may be split to drive a plurality of plasma applicators or antennas to enable an array of plasma plumes to be produced. This idea is explored in further detail below.

The apparatus may include an impedance adjustor arranged to control the impedance at the plasma generating region when gas and microwave energy are delivered thereto. The impedance adjustor may permit the apparatus repeatably to create a high impedance condition in the plasma generating region to enable the plasma consistently to be struck. Moreover, the impedance adjustor may enable the apparatus to operate with different levels of microwave energy, different gas compositions, and/or different flow rates, and/or different treatment materials, each of which may affect the impedance seen at the plasma generating region.

The impedance adjustor may be arranged to selectively occupy either (i) a plasma strike state in which a first impedance for striking the plasma is created in the plasma generating region when gas and microwave energy are delivered thereto, or (ii) a plasma maintenance state in which a second impedance for maintaining the plasma is created in the plasma generating region when gas and microwave energy are delivered thereto, the second impedance being lower than the first impedance. The first impedance may be very high, e.g. as close as possible to infinity. The apparatus may include a strike detector arranged to determine if the plasma has been struck; the impedance adjustor may be arranged to switch its state based on a signal from the strike detector. In one example, the strike detector comprises a reflected signal detector arranged to detect microwave energy reflected back from the plasma generating region, wherein the reflected signal detector is connected to the controller and the controller is arranged to operate the impedance adjustor based on information concerning detected reflected microwave energy from the reflected signal detector. The strike detector may also include a forward signal detector arranged to detect microwave energy delivered to the plasma generating region, wherein the forward signal detector is connected to the controller and the controller is arranged adjustably to control the microwave energy delivered to the plasma generating region based on information about detected forward and reflected microwave energy from the forward and reflected signal detectors respectively. The forward and reflected signal detectors may be power couplers arranged to sample the magnitude of microwave power delivered to the plasma generating region (i.e. forward power) and microwave power reflected from the plasma generating region (e.g. due to an impedance mismatch). From these samples, it is possible to detect a change in the impedance seen at the plasma generating region that is indicative of a plasma strike.

To strike plasma it is desirable to have a high electric field (e.g. high voltage condition). The invention may achieve this by providing a microwave power feed structure at the plasma generating region which exhibits high impedance at a location where microwave energy meets gas from the gas feed. The high impedance of the microwave power feed structure (which may be arranged as an antenna) may contribute towards the creation of a high voltage condition and the concentration of an electric field set up by the microwave energy for striking the plasma. In the plasma strike state (i.e. before the plasma exists) the gas is non-conducting and therefore has high impedance. In order to strike plasma, it is necessary to set-up the high impedance state at the distal end of the applicator or within the applicator in order to enable the high voltage (high electric field) necessary to break down the gas to be generated.

After the plasma is struck, the impedance seen by the microwave power feed structure, which is referenced to the distal end of the applicator, changes (i.e. due to the change of the non-conducting gas into the conducting plasma). An impedance mismatch may therefore occur, which can be detected by the strike detector. After the plasma is struck it is desirable efficiently to deliver the microwave energy into it, which means that it is desirable to match the generator impedance (i.e. the impedance of the microwave power feed structure) to the impedance of the plasma. This is the purpose of the plasma maintenance state. When occupying the plasma maintenance state, the impedance adjustor may be arranged to match the impedance of the microwave generator to a load seen at the plasma generating region, i.e. to the plasma. The reference plane may move from the distal end of the applicator (where the applicator forms a part of a transmission line that connects the generator to the applicator) to the proximal end of the applicator or somewhere inside the applicator after the plasma has been struck. The impedance of the maintenance state may vary according to gas flow rate, gas mixture, plasma temperature, etc., so dynamic impedance adjustment may be desirable.

After the plasma is struck and the impedance adjustor is switched into the plasma maintenance state, the location of an impedance mismatch moves from the distal end of the applicator (the interface between the plasma and the surface to be sterilised) to the interface between distal end of the feed cable (transmission line between the output of the generator) and the input to the applicator or somewhere along the applicator. Microwave energy does not escape out of the applicator since the size of the structure or the arrangement of the structure causes the microwave field to be cut-off, i.e. it cannot propagate outside the applicator wall or cavity. It is desirable to couple microwave power efficiently into the plasma. The impedance adjustor may therefore operate dynamically in the plasma maintenance mode, e.g. based on signals from the strike detector. This arrangement may enable automatic compensation of microwave energy mismatch caused by changing the position of the applicator with respect to the treatment surface or the change in the characteristics of the treatment surface or treatment site or changes in the applicator itself, e.g. due to temperature elevation inside the applicator.

The apparatus of the invention thus permits the magnitude of microwave power delivered to the plasma to be controlled, e.g. through modulation of the microwave signal and control of amplifier gain or control of the level of input signal to an amplifier with fixed gain, as well as the efficiency by which it is delivered, e.g. through dynamic impedance matching. This arrangement may also enable the dosage of plasma energy delivered into the surface to be sterilised (e.g. biological tissue) to be accurately quantified. The impedance adjustor may comprise a dynamic filter network or a tuner. Thus, the tuner may be set up to create automatically an impedance and associated electric field necessary to strike the plasma and then change to the impedance necessary to maintain the plasma. The tuner may also be adjusted during the lower impedance state to allow the microwave power to be matched into the plasma when conditions change, i.e. gas flow rate, gas mix, or changes that may occur within the applicator itself.

The impedance adjustor may be part of, e.g. integrated with, the plasma applicator. For example, the microwave power feed structure may include a feed line, and the impedance adjustor may comprise either (a) a stub tuner having one or more stubs that are adjustably insertable into the feed line; or (b) one or more fixed stubs connected to the feed line that are electronically switchable between an open circuit configuration and a short circuit configuration; or (c) one or more variable capacitors connected in series and/or parallel to the feed line. Options (b) and (c) may be preferred because electronic switching of the impedance may be faster than switching that relies of mechanical movement. Effectively options (b) and (c) may represent controllable switching of fixed impedances into and out of the feed line on demand.

The fixed stubs in option (b) may be microstrip or coaxial lines. Each stub may be connectable to a DC source via power PIN diodes. Blocking inductors and capacitors may be arranged to prevent the microwave frequency energy from flowing into the DC source and the DC power from flowing into the feed line. Having a plurality of selectable fixed stubs of the same or a different electrical length may enable the arrangement to be tuned to a plurality of different loads.

The variable capacitors in option (c) may be one or more power varactor diodes. Changing the bias voltage of the diodes causes the capacitance they exhibit to change. Also, any load can be matched by providing an in-line (series connected) electrical stub capable of introducing a phase variation of up to half a wavelength (i.e. 180°) and a shunt (parallel connected) electrical stub capable of introducing up to a quarter wavelength) (90°) phase variation. These two variables may be introduced either by electromechanical means or electronic means. The variation of capacitance with bias voltage may be non-linear in this arrangement.

However, through the use of a suitable linearization algorithm or look table, a quasi linear effect may be achieved.

The power varactor diode idea may also be used to provide a phase variation

Another possible physical tuning mechanism includes a coaxial trombone, i.e. where the length of the coaxial line can be varied, e.g. using a movable shorted wall.

A plasma applicator with integrated impedance adjustor is another aspect of the invention and is discussed in detail below. Any of the arrangements discussed above may be incorporated into a hand held unit.

In one embodiment, the plasma applicator may be arranged selectively to emit plasma (ionising radiation) and microwave (non-ionising) radiation. The apparatus may thus emit plasma only, microwave energy only, or a mix of the two. In one example, the same microwave radiation generator may be used to create both the plasma and microwave energy, but different microwave antennas or applicators may be used to direct the microwave energy and the plasma into the surface. A tuning mechanism, e.g. the impedance adjustor discussed above, may be used to match (e.g. efficiently couple) the microwave energy and/or the plasma into the surface to be treated.

The ability to emit non-ionising microwave radiation as well as plasma is beneficial for applications such as the sterilisation of mattresses and pillows where bacteria may manifest beneath a surface to be treated as well as on that surface. In this instance, the plasma may be used to destroy the bacteria on the surface and the microwave energy may be used to destroy the bacteria beneath the surface, for example, 2 mm to 20 mm beneath the surface. The microwave frequency used to create the plasma maybe the same as that used to kill the bacteria directly using microwave power or two different microwave frequencies may be used. For example, 2.45 GHz, 3.3 GHz or 5.2 GHz may be used in both modalities or 4.2 GHz may be used to create the plasma and 2.45 GHz maybe used for sterilisation by non ionising radiation.

The apparatus may include a probe for directing the microwave radiation towards a surface to be sterilised, wherein the probe and plasma applicator are selectively connectable to the microwave radiation generator. The probe may include a horn antenna, e.g. a pyramidal horn or a conical horn. Alternatively, the probe may comprise a plurality of patch antennas fabricated onto a surface. Channels formed between the patch antennas may contain a gas feed. When the gas is present, the structure will emit sterilisation plasma, and when the gas is absent, the structure will emit microwave energy. A dielectric layer may be provided between the radiating patches and the surface the array structure makes contact with. It may be preferable to include a shutter arrangement that can be used to open up channels between the radiating patches to allow the plasma to emanate.

The apparatus may include a flow controller arranged to adjustably control gas flow in the gas feed. The gas flow rate may affect the size of the plasma plume or the plasma energy; this may be controlled by the flow controller. The gas feed may be arranged to direct the plasma through the outlet of the plasma generating region, i.e. to ensure that the plasma plume extends outside the plasma generating region to contact the surface to be sterilised.

The gases that are of interest for implementation of the apparatus disclosed herein are: air, helium, argon, nitrogen, compressed air, and carbon dioxide. The system need not be limited to these gases. Gas mixtures may be used, e.g. various concentration of argon, air and helium may be used, i.e. 1% air and 99% helium, or 5% air and 95% helium. To provide directivity to the gas feed, compressed air may be used. The combination of helium and compressed air may produce plasma that is particularly useful for the treatment of contact dermatitis.

As an example, the microwave radiation generator may include a solid state source capable of producing microwave power up to 300 W within a frequency band of 850 MHz to 925 MHz. The source may be arranged to sweep through this frequency band to find the resonant position whereby the maximum electric field is created. The source may be modulatable at frequencies from less than 1 Hz to greater than 100 kHz. In one particular example the modulation frequency may be set to 420 Hz with a 20% duty cycle.

The microwave frequency may be adjusted to enable the microwave energy delivered by the plasma to be optimised. For example, an antenna structure or applicator may be designed to operate at a certain frequency (e.g. 900 MHz), but in use the most efficient frequency may be different (e.g. 866 MHz).

The invention is not limited to using one frequency source. For example, a radiofrequency (RF) or medium frequency or low frequency source may be used to strike the plasma and a microwave source to maintain or sustain the plasma.

Coaxial or waveguide arrangements may be used as the applicators to create the plasma. Quarter wave (or an odd number thereof) impedance transformers may be realised in coaxial or waveguide systems and the specific structure used may be determined by the specific application and the environment in which it is desired to generate the plasma, i.e. over an external surface or inside a body cavity. In one embodiment, the system may comprise a solid state source, a tuner and simple fixed impedance (e.g. 50Ω) applicator structure to create and sustain plasma. In another embodiment, the system may not include a tuner, but may have a voltage transformer in the applicator (created e.g. using a plurality of impedance transformers) to strike the plasma and then keep striking to create a quasi continuous plasma. Repeated plasma strikes may be beneficial to regulating the plasma temperature.

To create the plasma, the plasma applicator may include any of microwave resonant structures, quarter wave voltage transformers, tuning stubs or posts, and an arrangement that uses a voltage transformer with suitable switching devices, e.g. a boost converter, to create a voltage that is high enough to strike the plasma, i.e. a voltage greater than 100 V, or igniters made from ceramic/intermetallic material or piezo-igniters which generate a high voltage spark based on the impact of a spring driven hammer arrangement on the piezoelectric ceramic material. Once the plasma has been struck, or initiated, the microwave energy may then be used to enable the plasma to be sustained or maintained. Tuning elements within the instrument or within the generator may be used to facilitate this.

The plasma applicator may include one or more resonator structures made from tungsten or another material that can withstand high temperatures. For example, the resonant structure may include a tungsten rod or needle coated with a material that is a good conductor, i.e. silver, copper or gold. As an example, silver nitrate may be used to electroplate the needle with silver or copper sulphate used to coat with copper. Other low loss conductors may be used, e.g. copper, aluminium, silver coated stainless steel, etc., which have a small length of tungsten crimped to the distal end where the plasma is to be generated.

Quartz tubes or quartz slices may be used inside the structure for the purpose of intensifying the electric field generated between the inner and outer electrode in a coaxial applicator arrangement by effectively bringing the two conductors closer together. The quartz tube also prevents arcing between the two conductors, which helps to produce a uniform beam of plasma. It is preferable to use a low loss quartz material.

It may be preferable to arrange the applicator in such a manner that the microwave energy and the gas mixture are fed into the structure at the same end, i.e. in the same direction as the applicator itself. This feature will be of particular relevance when the device is inserted into a natural orifice where an overall elongate shape is desirable. In such an arrangement, it may be preferable for the applicator to be flexible and have an overall length in excess of 1 m and a small enough diameter to allow it to be inserted down the instrument channel of a standard surgical endoscope, i.e. less than 2.5 mm.

The plasma applicator may comprise a waveguide cavity in which the plasma generating region is formed, the waveguide cavity having: a coupler located at an input end thereof for delivering microwave energy from the microwave radiation generator to the plasma generating region, and a gas inlet also located at the input end thereof for delivering gas from the gas feed to the plasma generating region. The coupler may be an E-field or H-field coupler, and may correspond to the microwave power feed structure mentioned above.

A dipole antenna may be located in the waveguide cavity to concentrate an electric field in the plasma generating region to promote striking plasma when gas and microwave energy are delivered thereto.

The plasma applicator may comprise a coaxial assembly having an inner conductor surrounded by and separated from an outer conductor, wherein the inner conductor tapers at its distal end to concentrate an electric field in the plasma generating region to promote striking plasma when gas and microwave energy are delivered thereto.

The coaxial assembly may include a plurality of voltage transformers each having different impedance, the plurality of voltage transformers being arranged to concentrate an electric field in the plasma generating region. Each voltage transformer may comprise a section of the coaxial assembly having a length that is a quarter wavelength of the microwave energy carried thereby from the microwave generator and wherein the impedances of the plurality of voltage transformers can be set by selecting the outer diameter of the inner conductor in each section of the coaxial assembly.

The plasma applicator may comprise a waveguide structure, which may be loaded with an electric or magnetic material to reduce the size of the waveguide cavity. The loading material may be porous or contain holes to enable the gas (or mixture of gases) to flow along the applicator. The waveguide applicator structure may contain quarter wave impedance transformer sections to increase the electric field at the distal end of the guide to enable plasma to be struck. In such an arrangement the height or diameter of the waveguide is varied in order to change the characteristic impedance of the particular section, e.g. a first quarter wave section may have a characteristic impedance of 20Ω, followed by a second section with an impedance of 600Ω, if this arrangement was fed by a 50Ω generator then it would produce an overall voltage multiplication of 30, i.e. a generator capable of producing 50 W into an impedance of 50Ω would produce a voltage of 1500 V at the end of the waveguide applicator structure.

The apparatus may include an adjustable stand off arranged to maintain a set minimum distance between the plasma applicator and the surface to be sterilised. The adjustable stand off can be used to vary the position of the plasma plume with respect to the surface to be sterilised, e.g. biological tissue. This may be used to control the temperature of the plasma at the surface.

The plasma applicator may include an additional section located at the distal end of the applicator that acts as a spacer to ensure that all materials or surfaces that the plasma comes into contact with is not heated above a set temperature, i.e. 38° C. The spacer may be adjustable to enable plasma to be produced at a range of temperatures. The distance between the end of the applicator and the spacer may be automatically adjustable. A temperature sensor or an array of sensors, e.g. thermocouples, may be placed at the end of the spacer to enable the plasma temperature to be measured and this information may be used in a closed loop to enable the adjuster to be automatically moved in accordance with the demanded temperature. It may be preferable for the spacer to be made from a thermal plastic or a ceramic material (although this invention is not limited to this being the case). The spacer may be moved by using an electromechanical actuator, e.g. a solenoid valve. In a particular embodiment, a tubular plastic spacer may be coated on the inner wall with a high permeability material and a coil or winding may be placed over the spacer; when the coil is magnetised, the spacer will be moved by a magnetising force set up inside the coil. A second tube may be required to space off the moveable spacer from the static coil. This arrangement may also be used in a control loop that takes into account microwave energy, gas flow and gas mixture, where these parameters may be varied in accordance with the temperature measured using the thermocouples or temperature sensors contained within the spacer. This arrangement may be used with a range of applicators to kill bacteria contained on a number of different surfaces.

The plasma applicator may include sensing means at its distal end which is arranged to provide information concerning the plasma to enable adjustments (if needed) to take place, i.e. spectral content (wavelengths), plasma energy and plasma temperature. For example, the plasma applicator or stand off may include any of a temperature sensor, a calorimeter, one or more photo detectors for monitoring a spectral content of the plasma produced at the distal end of the applicator. The information obtained from these sensors may be used in a feedback loop to control the plasma produced at the output of the system, i.e. control the microwave power level, the duty cycle, the waveform of the microwave power, the gas flow rate, the gas mixture, the gas timing, etc.

Integrated Gas Flow and Microwave Power Feed

The microwave power feed structure may be combined with the gas feed. A plasma system or a plasma applicator having this structure represent independent aspects of the invention.

Expressed generally, this aspect may provide a plasma sterilisation system in which microwave energy and gas are fed to a plasma generating region using a common coaxial structure, e.g. an integrated cable assembly. The integrated cable assembly may be used to transport gas along it in both directions, i.e. towards and away from the plasma applicator.

This aspect makes use of the fact that for effective propagation of electromagnetic fields at microwave frequencies, the wall thicknesses of the conductors involved in the microwave field propagation is limited to a small fraction of the overall conductor thicknesses, i.e. only a small fraction of the outer wall of the inner conductor and the inner wall of the outer are required to enable the microwave fields to propagate unimpaired, thus, the inner of the inner conductor and the outer of the outer conductor may be used for purposes other than to transport the electromagnetic energy.

It is proposed that the inner of the inner conductor be used to transport gas (or a mixture of gases) from the gas cylinder (source) into the plasma applicator. In one embodiment a passageway beyond the outer conductor may be provided for transporting residual gas away from the plasma generating region. The residual gas may be taken back to the gas cylinder or to an external reservoir for recycling or re-circulating back along the cable assembly to produce more plasma.

In order to keep the wall thicknesses to a minimum, it is preferable to use high conductivity conductors when constructing the coaxial assembly, i.e. it is preferable to use silver, copper, or gold when fabricating the inner and outer conductors, thus the transmission line that supports the propagation of the microwave energy may comprise of a flexible tube made form a dielectric material that is coated with a thin layer of metallic material on its inner and outer surface.

Accordingly, this aspect may be expressed as plasma sterilisation apparatus comprising a plasma applicator having an enclosed plasma generating region and an outlet for directing plasma out of the plasma generating region towards a surface to be sterilised; a microwave radiation generator connected to deliver microwave energy into the plasma generating region; and a common coaxial cable assembly arranged to transport simultaneously the microwave energy and gas to the plasma generating region. The cable assembly may be dimensioned so that can be inserted inside a range of natural orifices within the human or animal body or down the instrument channel of a surgical endoscope or other instrument that is used in key hole surgery. The microwave energy may be transported using a coaxial waveguide, that is able to support the propagation of a transverse electromagnetic (TEM) wave, and the gas (or gas mixture) is transported using either a channel formed by the centre of the centre conductor of the coaxial waveguide and/or a channel formed beyond the outer metallic wall of the waveguide and the inner wall of a jacket or protective layer. In this arrangement, the idea of limited conductor thickness required for the microwave field to propagate is used to enable the centre conductor to be used as a conduit for the gas. For example, if a solid conductor to be used was 2 mm diameter then only a fraction of this solid wire or rod is required for the propagation of the microwave field.

This aspect may also be expressed as plasma sterilisation apparatus comprising a plasma applicator having an enclosed plasma generating region and an outlet for directing plasma out of the plasma generating region towards a surface to be sterilised; a microwave radiation generator connected to deliver microwave energy into the plasma generating region; and a coaxial waveguide or transmission line arrangement comprising a tube of flexible low loss dielectric material having a centre section bored out or extruded to form a channel for directing a gas to the plasma generating region, wherein inner and outer walls of the tube are coated with a metallic layer, the thickness of which is related to the skin depth at the frequency of operation, i.e. between 1 to 10 skin depths at the frequency of the microwave energy, to form the metallic walls for the electromagnetic field to propagate thereby to deliver the microwave energy to the plasma generating region. As an example a solid PTFE material may be used as the dielectric, where the loss factor is between 0.0001 and 0.0008 at a frequency of 2.45 GHz. The electrical properties of the dielectric material and the thickness of the ratio between the inner diameter of the outer conductive layer and the outer diameter of the inner conductive layer are chosen such that the characteristic impedance of the transmission line is a commonly used value, for example, 50Ω or 75Ω. It may be desirable for the electrical and mechanical properties of the dielectric material to be homogeneous along the length of the material in order to minimise discontinuities along the transmission line that may lead to reflections and power loss along the cable.

This aspect may also be embodied as a single conductor waveguide, e.g. a flexible or flexible/twistable rectangular or cylindrical waveguide. In this instance, the gas may travel along the open cavity. It may be preferable to separate the cavity into longitudinal sections, where a first section is used to transport the gas from the source to the applicator, and a second section is used to transport the residual gas from the applicator back along the waveguide to the gas source. An alternative to using the centre of the waveguide to transport the gas, is to use a region or channel formed between the outer wall of the waveguide and an insulating jacket. This may be preferable since the gas flow inside the cavity may affect the electromagnetic fields propagating inside the waveguide. Due to the fact that the gas flow will be inconsistent and the gases used may vary, it may be preferable to transport the gas away from regions where the fields are set up inside the cavity as this may cause the propagation medium to be inhomogeneous. If it is chosen to use the centre cavity of a waveguide to transport the gas then it may be preferable to load the waveguide with a dielectric or magnetic material in order to reduce the effect caused by having the cavity filled with gas. In this arrangement, the loading material would need to allow the gas to flow, i.e. it may contain a number of holes or may only partially fill the waveguide cavity. In this arrangement, a number of different modes may be set up in the waveguide, for example, it may be preferable to set up the dominant $TE_{01}$ mode if a rectangular guide is used, or the dominant $TE_{11}$ mode if a circular guide is used. These modes are known as dominant modes due to the fact that they define the lowest frequency that can propagate in the guide. Other higher order modes will be set up inside the guide when higher frequencies are launched into the same guide. Other higher order modes may be used to propagate the microwave energy along the waveguide.

This aspect may also be embodied as a structure that is integrated with the plasma applicator. In this arrangement, the gas is fed directly into the applicator from a channel provided by either the hollow centre conductor and/or the channel formed between the outer wall of the second conductor and the insulating jacket. Either of the two channels may also be used to transport excess gas back from the applicator to the gas supply or reservoir. The applicator may comprise a hollow coaxial or waveguide structure for the gas and the microwave energy to combine. The structure is arranged in such a manner that the microwave energy produces a high enough electric field to enable the gas to be turned into plasma or conducting gas. The integrated structure may contain an instrument having a single or plurality of impedance transformers to enable the voltage at the distal end of the transmission line to be multiplied or increased to a high enough level to enable the plasma to be struck. The impedance transformers may be quarter wave transformers or any odd multiple of a quarter of the wavelength at the frequency of operation. The integrated applicator may be produced such that it has the same physical diameter as the integrated microwave/gas cable assembly (the transmission line). The structure may be arranged in such a manner that the hollow centre conductor carrying the gas feeds straight into the first impedance transformer contained within the applicator. The use of high frequency microwave energy means that the associated quarter wavelengths are small enough to enable a suitable sized instrument to be implemented. It is also advantageous to create the high voltage at the distal end since it means that it is not necessary to set up high voltages along a transmission line that may be close to a number of vital body parts or organs and the arrangement can support the use of small diameter constant impedance transmission lines that do not suffer from the disadvantages of RF systems whereby the fields tend to collapse due to the capacitance between the inner and outer conductor.

In one example of this aspect, the inner conductor of the coaxial assembly discussed with respect to the controllable sterilisation system above may be a hollow tube having a channel therein, and wherein the gas feed is connected to the channel to deliver gas to the distal end of the inner conductor. The thickness of the tube may be less than ten (preferably five or fewer) skin depths of the material at the frequency of the microwave energy carried thereby from the microwave generator.

Alternatively or additionally, the coaxial assembly may be housed in a casing and may include a gas flow channel enclosed by the casing that is located outside the outer surface of the outer conductor. The outer conductor may have a thickness of less than ten (preferably less than five) skin depths of the material at the frequency of the microwave energy carried thereby from the microwave generator and the gas flow channel is an annular channel between the outer surface of the outer conductor and an inner surface of the casing.

In one embodiment there may therefore be two independent gas flow channels in the microwave power feed structure. This may permit gas to be delivered to and extracted from the plasma generating region using a single self-contained unit. As plasma sterilisation system and a plasma applicator having such a structure may be another independent aspect of this invention.

In this aspect, the integrated structures may enable the plasma sterilisation system to be used invasively, i.e. to transport microwave energy and gas into the body (or elsewhere) for generation of biologically useful plasma inside natural orifices (or elsewhere). This aspect introduces instrumentation required to prevent a build up of pressure within the natural orifice (or other region of the body or external to the body that may be of interest) by returning the residual gas that is not used for plasma generation. This feature is also beneficial in terms of enabling unused gas to be recycled and not lost into the atmosphere.

According to one embodiment, there may be provided a first section of a coaxial microwave cable assembly (e.g. transmission line) to enable the gas to be fed into the applicator to enable plasma of appropriate nature to be generated, and a second section of the same coaxial microwave cable assembly to enable the gas to be withdrawn from the structure for the purpose of preventing pressure build up within the cavity or the natural orifice where the applicator is inserted. The first and second sections may include the hollow inner conductor and the channel between the outer conductor and housing discussed above.

It may be desirable to suck the gas back along the applicator and the cable to ensure that pressure cannot build up within the cavity. It may also be desirable to use this arrangement to re-circulate a portion of the gas rather than losing the returned gas into the atmosphere. This may help to preserve valuable sources of natural gases.

The residual gas may be returned to a reservoir which acts as a store for the returned gas to enable it to be effectively used again to create more treatment plasma. It may also be necessary to include a number of one way valves in the system in order to ensure that the gas flow is in the desired direction within the system.

The same channel or one of the channels introduced into the transmission line structure may be used to introduce materials other than gas into the tissue, e.g. it may be beneficial to introduce a liquid or fluid into the region being sterilised prior or subsequent to the sterilisation process. In such an arrangement, the (or one of) the gas channel(s) will be used to transport the gas and the other material in a serial manner.

This aspect may also include a gas control system, which enables excess gas to be returned by sucking it back along the plasma applicator and the cable assembly. The gas control system may also be arranged to control the gas fed into the plasma generating region to create the plasma, e.g. by permitting adjustment of the pressure or flow rate.

The gas control system may contain a reservoir to enable the excess plasma to be stored before being pumped back into the plasma applicator to produce more plasma. The gas control system may also contain a gas combiner or mixer to enable the returned gas to be mixed with the gas supply (from a cylinder or a gas generating system). The gas control system may also contain an arrangement of pumps to enable the gas to be sucked from the plasma applicator, or pumped into the gas combiner, or pumped into the plasma applicator. The gas control system may also contain an arrangement of gas flow valves to ensure that the gas flows in the desired direction only. The gas control system may also contain a flow switch, whose operation may be governed by signals obtained from a microprocessor, DSP unit or other suitable digital or analogue signal processing arrangement. The flow switch may be a solenoid arrangement where an applied magnetic field controls the position of the valve or the level of valve opening. The gas control system may also contain a flow rate adjuster and monitor, whose operation may be governed by signals obtained from a microprocessor, DSP unit or other suitable digital or analogue signal processing arrangement. The gas control system will also contain an arrangement of pipes or tubes that may be made from a plastic or metallic material. The gas control system may contain at least one gas cylinder or a gas generator.

The control system may also responsible for monitoring the remaining level of gas inside the cylinder (s), the amount of gas inside the applicator, the flow rate, and the pressure.

This aspect may also include a means of synchronising the microwave energy with the gas flow to ensure that the microwave energy is only present when the plasma applicator is filled with gas to enable the desired plasma to be struck and maintained. A microprocessor or digital signal processor may be used to perform the timing functions to ensure that the microwave power and the gas are turned ON and OFF at the correct times. Correct synchronisation ensures that gas is not wasted and that the microwave energy produced by the microwave generator is not reflected back from the plasma applicator to the generator. The latter event is undesirable as it will cause applicator and cable heating, and also may lead to unnecessary stress on these and other components within the system. Monitors will be included to indicate when excess microwave power is being reflected back along the cable and/or the gas flow rate varies from the demanded value.

In one embodiment, this aspect may provide plasma sterilisation apparatus having a plasma applicator having an enclosed plasma generating region and an outlet for directing plasma out of the plasma generating region towards a surface to be sterilised; a microwave radiation generator connected to deliver microwave energy into the plasma generating region; and a gas feed connected to deliver gas into the plasma generating region, wherein the plasma applicator comprises a coaxial assembly having an inner conductor surrounded by and separated from an outer conductor, the inner conductor being a hollow tube having a first gas flow channel therein, and wherein the coaxial assembly is housed in a casing and includes a second gas flow channel enclosed by the casing that is located outside the outer surface of the outer conductor, and wherein the gas feed is connected to one of the first and second gas flow channels to deliver gas to the plasma generating region and wherein the apparatus includes a gas extractor connected to the other of the first and second gas flow channels to withdraw residual gas from the plasma generating region.

The apparatus may include a flexible coaxial feed cable connected to the microwave radiation generator to deliver microwave energy to the plasma applicator, wherein the coaxial assembly is integrally formed at a distal end of the feed cable. The feed cable may also include the first and second gas flow channels.

Plasma Applicator with Integral Tuning

As mentioned above, an independent aspect of this invention may be the provision of the impedance adjustor, i.e. the ability to tune the system, within the plasma applicator. This aspect may be expressed as a plasma applicator containing a tuning mechanism (e.g. an automatically controlled tuning mechanism). In use, the distal end of the plasma applicator may be in close contact with the tissue or surface to ensure that the plasma energy is efficiently coupled to the surface being treated to enhance the efficacy of the system. An adjustable spacer as described above may also be use in this aspect. This arrangement may also ensure that the microwave energy is efficiently converted into clinically useful plasma energy.

The tuning mechanism of this aspect may be set up to provide one specific impedance or may be set up to provide automatic impedance adjustment to enable the plasma energy to be matched with the plasma once it has been struck to enable effective sterilisation of the surface of interest (which may be biological tissue, or other material to be sterilised). Tuning in the applicator or hand-piece offers the advantage of overcoming the need to take into account phase changes and insertion losses associated with the transmission line that connects the generator to the applicator, additional interconnects and other components within the microwave line-up when carrying out the tuning necessary to strike and maintain the plasma within the generator.

This aspect may overcome the effect of insertion loss (cable loss) and phase variations associated with a microwave cable assembly, which is a drawback for systems with a tuning network housed with the generator electronics. By incorporating the tuning mechanism in the hand-piece it should be possible to set up a first impedance to strike the plasma and the second impedance to sustain the plasma with relative ease.

This aspect may be expressed as a plasma applicator comprising an enclosed plasma generating region having a gas inlet for receiving gas from a gas feed, an energy inlet for receiving microwave energy, and an outlet for delivering plasma out of the plasma generating region towards a surface to be sterilised, wherein the plasma applicator includes an impedance adjustor (e.g. contained in the plasma generating region) arranged to control the impedance at the plasma generating region when gas and microwave energy are delivered thereto. The impedance adjustor may be arranged to create high impedance at the plasma generating region when gas and microwave energy are delivered thereto thereby to strike non-thermal plasma for delivery out of the applicator. The impedance adjustor may comprise a dynamic tuning mechanism to react more quickly than a tuning mechanism located inside the generator or some other remote location away from the plasma applicator. The tuning mechanism may be an arrangement of variable stubs, fixed stubs that can be changed from open circuit to short circuit state using an arrangement of power PIN diodes, an arrangement of power varactor diodes or the like, as described above.

The impedance adjustor may be automatically adjustable to ensure the plasma can be efficiently struck, maintained, and matched or coupled to the plasma to enable effective sterilisation of the treatment surface (biological tissue or external surface) or the treatment site. The system will adapt to a change in impedance of the applicator due to changes in the gas flow, gas mixture, microwave energy, heating inside the applicator, other causes of phase change within the applicator, physical manipulation of the applicator with respect to the tissue or changes in the characteristics of the site due to the plasma treatment process. In a specific embodiment, the impedance adjustor may comprise: one or more mechanically movable tuning stubs that are insertable into the plasma generating region; an electromechanical actuator arranged to move the stubs; one or more detectors arranged to measure the magnitude of forward and reflected energy inside the applicator; and a controller that takes the sampled forward and reflected signals and provides the necessary control signals to the actuator necessary to allow the tuning stubs to be moved into a position to create the necessary impedance to strike, sustain or match the plasma. All these components may be part of the applicator, although the controller may be provided remotely. DC power cables and signal lines may be used to transport the DC power and the control signals to and from the applicator. The tuning mechanism may also consist of an arrangement of mechanical rods (or stubs), semiconductor power varactor diodes or PIN diodes. In the case of the diodes, a control voltage is used to change the characteristic of the diode, which, in turn, creates or sets up the necessary resonant or tuned condition.

In one embodiment, the impedance adjustor may be implemented as a variable capacitance connected in shunt to the microwave power feed structure. The variable capacitance may be embodied as a plurality of fixed capacitive stubs that are selectively connected to the microwave power feed structure using power PIN diodes, or as one or more variable power varactor diodes. Since the impedance can be adjusted electronically in embodiments using PIN or varactor diodes, it may react faster than the mechanical embodiment discussed above. This may be advantageous in terms of moving from the plasma strike to the plasma sustain state.

The controller for the automatic tuning arrangement may comprise an analogue signal processor consisting of an arrangement of operational amplifiers. This may be particularly useful for an integrated plasma applicator, e.g. a hand-held unit, which contains the controller, actuator and tuning stubs. Alternatively, the controller may include a digital microprocessor arranged to process information obtained from the detectors to control the electromechanical actuator; an 8-bit, 16-bit or 32-bit microprocessor or PIC device may be used, which may also be integrated into the hand-piece. The detectors may be power couplers arranged to sample the forward and reflected power signals. These couplers may be E-field probes, H-field loop couplers, stripline or microstrip couplers.

In another example, the plasma applicator may comprise a waveguide structure. This aspect may thus provide a method of automatically tuning a waveguide plasma applicator firstly to form an antenna having a high impedance condition suitable for striking a low temperature atmospheric plasma and subsequently (e.g. after the plasma is struck) to form an antenna having a low impedance condition suitable for maintaining the plasma. The method may include dynamically adjusting the low impedance condition (e.g. based on measurements by the detector) to form an antenna having a variable impedance condition suitable for substantially matching the antenna into the tissue. The plasma generating region may be formed in a waveguide cavity. The high impedance, low impedance and variable impedance conditions may be set up by automatically varying the position of one or more tuning elements contained within the waveguide cavity. This may overcome the need to use complex applicator or antenna structures since it is not necessary to use resonant structures containing a plurality of quarter wave transformers or the like. The waveguide may be cylindrical or rectangular. The waveguide may be loaded with a dielectric or magnetic, or dielectric and magnetic materials in order to reduce the size of the structure.

Alternatively, the plasma applicator may include a coaxial structure. Here, the automatic tuning mechanism may be arranged to vary the diameter or length of the coaxial structure to provide the tuned condition. Alternatively, it may be possible to introduce tuning stubs inside the coaxial structure by introducing them through the wall of the outer conductor into the dielectric material that separates the inner and outer conductors. It may also be desirable to introduce the tuning stubs into the outer wall of an applicator design that contains a single or plurality of resonator or impedance transformation sections, i.e. quarter wave impedance transformers, and vary the lengths of the stubs inside the coaxial structure to vary the electromagnetic field set up within the structure to assist in obtaining the desired condition necessary to create plasma for sterilisation. A single or a plurality of grooves may be provided in the outer conductor to reduce the distance between the inner and outer conductors. These grooves will form fixed stubs, if separated in a suitable manner, and may provide a relatively simple solution.

Plasma Applicator—Plural Plasma Plumes

The system described above may include a power splitting unit arranged to split the microwave energy between a plurality of plasma generating regions formed in the plasma applicator, wherein the gas feed is connected to deliver gas to each plasma generating region, and the outlets of the plurality of plasma generating regions are spatially arranged to deliver a substantially uniform blanket or line of plasma from a plurality of plasmas generated in each respective plasma generating region.

In one arrangement there may be 10 or more plasma generating regions housed in a frame defining an aperture, the plasma applicator being arranged to direct the plasmas inwards from the frame to provide a blanket of plasma for items passed through the frame.

Alternatively or additionally, the plurality of plasma generating regions may all be housed in a handheld unit.

One or more proximity sensors arranged to detect if a object is within a threshold distance from the plasma applicator, wherein the plurality of plasma generating regions are arranged to provide a blanket of plasma directed at an object detected to be within the threshold distance from the plasma applicator. An arrangement of thermal sensors may also be included and connected in a feedback loop to enable adjustments of gas flow, gas mixture and microwave energy to be made to ensure that the plasma temperature does not exceed a predefined or user set limit.

The plasma applicator may have a disposable outer cover arranged to provide the outlets from the plurality of plasma generating regions. Active elements of the applicator, e.g. the tips of an antenna or conductor where the plasma strike occurs may be integrated into the cover to provide a disposable or easily replaceable unit. The cover may also be used to ensure that the plasma temperature will not damage the tissue or materials (surfaces), i.e. less than 37° C.

The splitting of the microwave power between a plurality of plasma generating regions in the plasma applicator may be another independent aspect of the invention. In one example of this aspect, the plasma applicator may comprise a plasma 'brush' or 'comb' type arrangement that can be used on external environments or the surface of the human or animal body. This aspect may be used with the controllable microwave energy based plasma sterilisation system discussed above.

According to this aspect, the plasma applicator may comprise an elongate structure in which the microwave energy is conveyed and having a plurality of outlets arranged along an outer surface thereof, each outlet being for one of the independent plasma plumes. In one embodiment, the plasma applicator may comprise a coaxial line which consists of an outer conductor and a centre conductor, wherein a plurality of slots are formed in the outer conductor to enable plasma to be emitted. The centres of the slots may be aligned or offset, depending on the clinical application. A gas (or mixture of gases) may also be present inside the coaxial structure. A plurality of high electric fields may be set-up inside the coaxial line at the location of the slots to enable plasma to be struck and emitted from each slot. Microwave energy is fed into the coaxial structure, and this may be used to strike and maintain the plasma or to maintain the plasma only, e.g. the high voltage (high impedance) condition may be set up using an arrangement of impedance transformers or a tuning or matching arrangement to enable the plasma to be struck and, once the plasma has been struck, the tuning arrangement may be adjusted to enable the plasma to be maintained. Without this adjustment, the impedance mismatch created when the conducting gas is formed would cause an excessive level of reflected power to be returned to the generator. Alternatively, the high voltage (high impedance) condition may be set up using one of the following arrangements: piezo-electric igniters or an ignition coil or a transformer with a high turns ratio (e.g. 1:100) or a flyback (or boost) circuit and the plasma may be maintained using the microwave energy fed into the coaxial structure and matched to the low impedance state.

The coaxial line structure may be arranged so that the plurality of nozzles or holes for plasma to be emitted are placed a distance of a half a wavelength at the frequency of operation apart (between the centres of adjacent holes or nozzles). It can then be assured that a high E-field condition is set up at each nozzle by shorting the centre conductor of the coaxial line to the outer conductor of the coaxial line at the distal end of the applicator (coaxial line) and then arranging for the first nozzle to be positioned a quarter wavelength from the shorted end to produce the desired E-field maxima. If the second nozzle is then positioned a half wavelength from the first nozzle (moving away from the distal end), a second maxima will occur in the E-field at the centre of said second nozzle. If subsequent nozzles are positioned a half wavelength from adjacent nozzles, then each nozzle will be located at an E-field maxima. When a gas (or mixture of gases) is/are introduced into the coaxial line, ionisation will take place at the location where E-field maxima occur (the centres of the nozzles) and plasma will be emitted from each nozzle.

The coaxial line may be loaded with a dielectric or magnetic material in order to reduce the overall physical length of the 'brush' or 'comb' or to reduce the spacing between adjacent plasma emitters, e.g. at 10 GHz without loading the half wavelength spacing between adjacent plasma plumes will be approximately: $3\times10^8/(10\times10^9\times2)$ =15 mm, whereas at 10 GHz with a loading material that has a dielectric constant of 49, the half wavelength spacing between adjacent plasma plumes will be approximately: $3\times10^6/(10\times10^9\times2\times\sqrt{49})$=2.14 mm. It may also be possible to increase the frequency of operation in order to reduce the overall physical length of the 'brush' or to reduce the spacing between adjacent plasma emitters, e.g. at 25 GHz without loading the half wavelength spacing between adjacent plasma plumes will be: $3\times10^9/(25\times10^9\times2)$=6.25 mm, this spacing may be sufficient to enable a quasi continuous line of plasma to be formed along the length of the applicator.

In this particular realisation of the device, the distal end of a coaxial tube will have the centre conductor shorted to the outer conductor and the position of the first jet will be a distance of a quarter of the wavelength at the frequency of operation from the short circuit to enable a maxima in the electric field to occur at the centre of the first nozzle, thus the condition for a plasma strike to occur has been set up. All subsequent jets are then placed a distance of half wavelength between centres at the frequency of operation where subsequent maxima in the E-field occur.

It may be preferable to include a variable quarter wave (or an odd multiple thereof) section at the distal end of the 'comb' applicator structure to enable the open circuit condition necessary to strike the plasma to be initially set up and then adjusted or changed to the low impedance condition necessary to sustain the plasma. This adjustment may be implemented using a sliding end section that consists of a movable end cap with a tube at the centre, and arranged in such a manner that the movable section slides over the outer and inner conductors of the coaxial line applicator structure. The movement of the end cap produces a $\lambda/4$ or 90° phase adjustment and the end cap is essentially an air coaxial line with the inner and outer conductors shorted together and the centre and outer conductors of the section slide over the main coaxial line or applicator. The fixed and moving conductors must make good electrical contact with one another. A sprung metal arrangement may be used at the ends of the conductors contained within the moveable to ensure that a good electrical contact is made. It may be preferable to move by a distance of less or more than $\lambda/4$, e.g. a movement of $\lambda/8$ will provide a capacitive or inductive reactance that is equal in magnitude to the characteristic impedance of the coaxial transmission line. It may also be desirable to increase the outside diameter of the movable inner conductor to produce an impedance transformation within the structure, e.g. the overall length of the movable end section may be $3\lambda/4$ in length and the middle section may be a larger diameter to create a lower characteristic impedance section, or all three sections may be of different diameters.

In order to ensure that the end section does not introduce discontinuities within the coaxial transmission line then the differences in height produced by the movable section should be kept as small as possible, i.e. increase in centre conductor diameter should be kept to less than around 0.2 mm.

The mechanism by which the end section can be moved may consist of a solenoid or a plurality of solenoids wound around the end to produce a movement based on a magnetising force set up in the solenoid winding(s) using a current source arrangement.

A single or plurality of tuning stubs may be provided within or along the coaxial structure between the centre conductor and the outer conductor to enable electric field maxima to be set up where the centres of each nozzle occur. The tuning stubs may comprise metallic posts or inserts, dielectric posts or inserts or magnetic posts or inserts or a combination of the three materials. The physical and electric properties of the tuning posts or inserts may be varied along the length of the elongate transmission line structure to ensure that the electric field produced at the centre of each nozzle is the same in order to ensure that the line of plasma produced by the device is uniform.

The structure may contain a plurality of impedance transformers positioned along the coaxial structure and the physical and electrical properties may again be varied to ensure that the line of plasma produced by the device is uniform along the length of the structure.

The plasma applicator may include a means of gas control arranged to control the gas flow rate along the length of the elongate structure to enable the line of plasma produced by the device to be uniform along its length in terms of plasma energy and/or temperature. Flow constrictors or valves may be positioned along the length of the structure to implement this feature. Miniature valves may be located near the centre of each nozzle. Said valves may be set to provide a fixed gas flow at each nozzle or be capable of being automatically adjusted on the basis of measured plasma energy produced at each nozzle. In the latter case, each valve may contain a miniature solenoid valve that can be moved by applying a current to a coil of wire wound around a rod or shaft made from a magnetic material.

An elongate waveguide (rectangular or cylindrical cavity) may be used in place of the coaxial structure. A plurality of tuning posts or stubs may be provided along the length of the cavity to enable electric field maxima to occur at the positions where the outlets (e.g. nozzles or slots) are present and where the plasma is emitted. Gas flow restrictors may also be placed along the length of the waveguide assembly to help ensure that the plasma generated at each nozzle is the same.

The nozzles may be covered with a disposable element (e.g. that will be sterile in use) which may act as a spacer to ensure that the temperature of the plasma is less than or equal to 37° C. to prevent damage to tissue structures or materials being sterilised. This cover may be made from a high temperature plastic or ceramic material.

In another embodiment, the microwave source power is split or divided into a plurality of smaller power sources, each producing the same power level, and a separate applicator arrangement is connected to each source to create a 'brush' or 'comb' type arrangement. Each applicator may contain a means of producing a high voltage for causing the necessary ionisation discharge or breakdown, and a means of sustaining the discharge or plasma. The power divider may be a coaxial divider or coupler, a microstrip divider or coupler or a waveguide divider or coupler. For example, the plasma applicator may include a microstrip or stripline power splitter structure arranged to split the input microwave power to create a plurality of lower power sources, each of which are arranged to produce an electric field which support striking of an independent plasma plume. Each lower power source may thus be connected to deliver microwave energy to a plasma generating region associated with a respective outlet. The outlet may be connected along a common line to enable a line of plasma to be formed.

The elongate structure may include one or more gas feeds for delivering a gas (or a mixture of gases) to each plasma generating region to assist with the production the plasma.

In this arrangement, it is preferable for each source to be arranged to produce the same amount of power to enable the uniform plasma to be produced along the length of the applicator. It is preferable for the distance between adjacent nozzles or plasma sources to be such that plumes produced by each individual source combine together and there are no visible gaps in the plasma line formation. The plasma applicator may include gas control means arranged to control the gas flow rate at or in the region of each nozzle, where individual plasma plumes are produced in order to ensure that a uniform line of plasma is produced along the length of the elongate structure, i.e. the same plasma energy is produced at each nozzle.

This device may be provided as a hand held tool for use in treating the human or animal body. However, for larger scale applications, e.g. relating to sterilisation of hospital wards, it may be preferable to arrange the plasma sterilisation system in such a manner that a large number of jets, for example between 100 and 500, emit plasma around a frame defining an aperture, which may be a door entrance to a hospital ward. The height and the width of the aperture may be adjustable (e.g. automatically using proximity sensors) in accordance with the size of the person that wishes to enter the ward. In this system, the person could be sterilised using the plasma system before entering the hospital ward.

For similar applications an array of plasma jets may be arranged to emit plasma around a frame, and the frame may be automatically moved along surfaces or around a hospital bed to enable the bed or surface to be sterilized. This process may be semi-automated, i.e. a hospital worker may be required to position the frame into position and the system will automatically scan the item or surface of interest.

In a development of this aspect, the plasma sterilisation system may be arranged in such a manner that a single jet of plasma (or a small number of jets, for example, two, or three) are used to scan over a surface of an item or material. One example of this embodiment maybe a box containing two plasma jets that are arranged in such a manner that the jets move around the box on a frame, or gantry, that goes all around the box. Such an arrangement may be used to sterilise hands before a person enters a hospital ward. The plasma applicator may be connected to a scanning arm similar to that used in x-y plotters. A plurality of arms (e.g. five or more) each having their own plasma jet may be used.

A further example of this arrangement may provide a box whereby the scanning arms are adjustable in height and side movement, for example, the hand may be placed nearby one of the side walls and on the base of the box and a first arrangement of proximity sensors may be used to move a single or plurality of plasma jets down from the top to ensure that the top of the hand is covered in plasma, and a second arrangement of proximity sensors may be used to move a single or plurality of plasma jets in from the side to ensure that the side of the hand is covered in plasma. A similar arrangement may also be used to sterilise items that are commonly picked up and used by hospital staff, for example, pens, clipboards, etc.

Invasive Plasma Applicator

In another aspect of the invention, the plasma applicator may comprise a device that may be introduced down the instrument channel of a surgical endoscope (or a bronchoscope or another scoping device) or to be inserted into the body through keyhole or minimally invasive surgery. For example, this type of applicator may be introduced through natural orifices within the body, for example, the nose, ear, anus, mouth, etc. This aspect may be used with the controllable microwave energy based plasma sterilisation system discussed above.

This aspect draws upon miniature applicator or instrument arrangements and feed structure designs that enable microwave energy and the gas (or mixture of gases) to be transported along a single flexible microwave cable assembly that may be delivered down the instrument channel of a surgical endoscope. This type of use may impose constraints on the physical dimensions of the plasma applicator, e.g. it may be required for the overall device to consist of a 2 m long cable assembly (e.g. a semi rigid cable that can be manipulated by a surgeon to guide a distally located plasma plume to a region of interest) with an outer diameter of no more than 2 mm. In an embodiment according to this aspect, the plasma applicator may include an instrument comprising two quarter wave impedance transformers with an overall length of 10 mm or less. The mechanical construction may allow for the applicator or the head to be moved or manipulated independent of the feed cable.

In one embodiment of this aspect, the plasma applicator may comprise a coaxial structure having an overall diameter that is 3 mm or less, and a length of up to 4 metres to enable the structure to be introduced down the instrument channel of a standard surgical endoscope or be used in key-hole or minimally invasive surgery where the tissue (or object) to be sterilised (or treated) is not easily accessible.

The applicator structure may be flexible, e.g. to permit easy manipulation of the distal end of the applicator where the plasma is produced to enable it to be used to sterilise a range of inserts or tissue structures.

It is desirable for the length of the impedance transformers used in this embodiment to be as short as possible. This may be achieved by using a high microwave frequency to create and sustain the plasma or a lower microwave frequency and a dielectric (or magnetic) loading material or a combination of the two, e.g. considering a two stage (or section) transformer. For example, if a microwave frequency of 15 GHz and a material with a dielectric constant of 25 is used, then the length of each quarter wave section is approximately $3\times10^8/(15\times10^9\times4\times\sqrt{25})=1$ mm, and the overall length of the transformer would be 6 mm (assuming that the second section contains no loading material in order to create the desired higher impedance second stage, i.e. $[3\times10^8/(15\times10^9\times4)=5$ mm).

Different loading materials may be used within the transformer structure in order to achieve an optimal compromise between the overall voltage transformation produced by the transformer structure to generate an electric field of sufficient magnitude to create plasma, and an overall physical length that makes it possible for the end-piece containing the transformer to be introduced down the instrument channel of a surgical endoscope and for it to be easily manipulated once positioned inside the body cavity.

In order to keep the wall thicknesses of the inner and outer conductors used in the long flexible coaxial line to a minimum, it is desirable to use high conductivity materials to fabricate the structure, i.e. it is preferable to use silver, copper, or gold when fabricating the inner and outer conductors.

The coaxial line structure may be arranged to permit both microwave power and a suitable gas (or mixture of gases), to be transported simultaneously along an integrated structure that has an outer diameter of less than 3 mm. The microwave power will be transported using a coaxial transmission line, that is able to support the propagation of a transverse electromagnetic (TEM) wave, and the gas (or gas mixture) is transported using either a channel formed within the centre of the centre conductor of the coaxial transmission line and/or a channel formed between the outer metallic wall of the transmission line and the inner wall of a jacket or protective layer. In this arrangement, the idea of limited conductor thickness required for the microwave field to propagate is used to enable the centre conductor to be used as a conduit for the gas. For example, if the solid conductor to be used was 1 mm diameter then only a fraction of this solid wire or rod is required for the propagation of the microwave field. This phenomenon is known as the 'skin effect' and is extremely useful when developing systems similar to the one presented here, where it is advantageous to only require a portion of the inner and/or outer conductor(s) within a waveguide or transmission line to propagate the microwave energy. It should be noted that this invention is not limited to the propagation of TEM waves within the transmission line or waveguide structure, i.e. at higher frequencies of operation or in single conductor waveguides (rectangular or cylindrical) other modes will propagate, e.g. $TE_{10}$, $TE_{11}$ or higher order modes. On the other hand, it may be preferable to ensure that the structure is only able to support a TEM mode of operation in order to ensure that the coaxial structure cannot emit or radiate microwave energy from its end or aperture, i.e. the cylindrical waveguide produced by the coaxial transmission line is cut-off. A section of outer conductor within the structure where no centre conductor may be provide to ensure that the microwave field cannot propagate or radiate out of the end of the structure.

The coaxial transmission line arrangement used here to enable the microwave field to propagate is formed using a tube of flexible low loss dielectric material, where the centre section of the tube is bored out or extruded to form a channel for a gas (or mixture of gases) to flow, and the inner and outer walls of the tube are coated with a metallic layer, the thickness of which is related to the skin depth at the frequency of operation and may preferably be between 4 to 10 'skin depths' at the frequency of operation, to form the metallic walls for the electromagnetic field to propagate. As an example, a solid PTFE material may be used as a dielectric, where the loss factor is between 0.0001 and 0.0008 at a frequency of 2.45 GHz and the material used to form the outer of the inner conductor and the inner of the outer conductor may be copper, where the skin depth at 2.45 GHz is 1.32 µm. The electrical properties of the dielectric material and the thickness of the ratio between the inner diameter of the outer conductive layer and the outer diameter of the inner conductive layer are chosen such that the characteristic impedance of the transmission line is a commonly used value, for example, 50Ω or 75Ω. The electrical and mechanical properties of the dielectric material should be homogeneous along the length of the material in order to minimise any discontinuities along the transmission line which may lead to reflections, standing waves, or power loss along the cable.

BRIEF DESCRIPTION OF THE DRAWINGS

Examples of the various aspects discussed above are described in detail below with reference to the accompanying drawings, in which.

DETAILED DESCRIPTION

Further Options and Preferences

Figure 1:
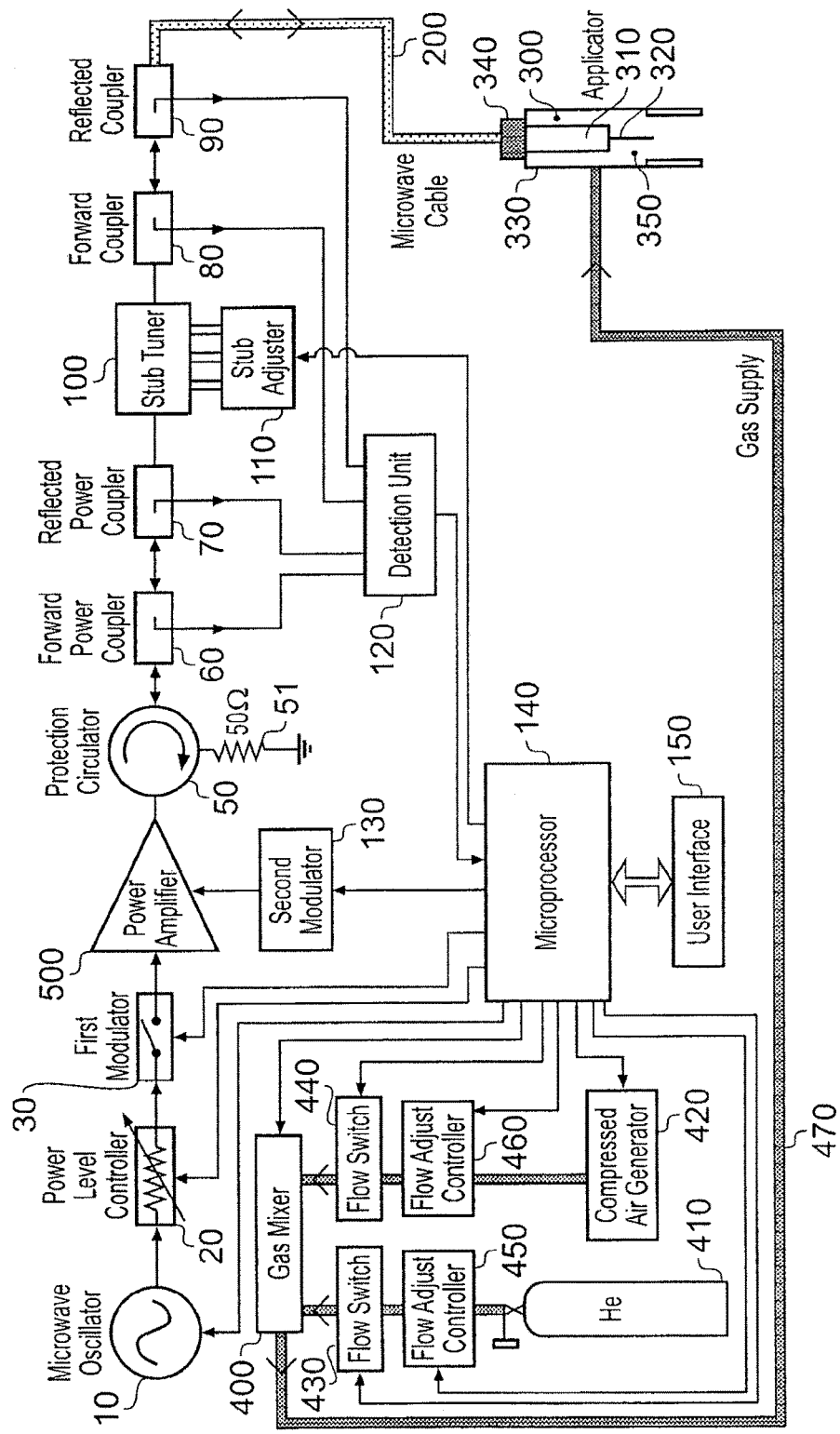
FIG. 1 is a block diagram showing a plasma sterilisation system that is an embodiment of the invention with an impedance adjustor.

FIG. 1 is a block diagram of a plasma sterilisation system that is an embodiment of the invention. The system comprises a microwave energy source 10, e.g. a low power microwave source oscillator. The source 10 is arranged to produce power levels from greater than −10 dBm to less than 20 dBm at a stable single output frequency. The output frequency may be adjustable over a narrow band of frequencies, e.g. a centre frequency of 900 MHz may be adjustable between 850 MHz and 950 MHz. The source 10 may be a voltage controlled oscillator (VCO), a dielectric resonator oscillator (DRO), a Gunn diode oscillator or a similar device that is capable of producing a controllable low power microwave signal. A frequency synthesiser that comprises of a plurality of VCOs or DROs may also be used.

The output from the source 10 is connected to the input port of a power level controller 20, whose function is to enable the power level of the signal from the source 10 to be adjusted over a range that is suitable to enable the plasma to be struck and then enable the plasma energy to be adjusted. The power level controller 20 may be a PIN diode attenuator that may be a reflective or absorptive type. The output from the power level controller 20 is connected to the input of a first modulator 30, whose function to switch the microwave power produced at the output of power controller 20 on and off using a signal produced by a controller 140 (e.g. a microprocessor) to enable the output microwave power produced at the output of power amplifier 500 to be in a pulsed format rather than a continuous wave format. The ability to control the switching action of first modulator 30 enables the pulse on time, the pulse off time and the pulse format to be controlled. This enables the ratio between the on and off times (the duty cycle) and the frequency (the inverse of the sum of the on time and the off time) to be determined. The modulation may not necessarily be periodic, i.e. it may consist of a train of pulses with various duty cycles and frequencies. The ability to control the pulse on and off times in this manner provides an additional means of controlling the energy produced by the plasma.

The output from first modulator 30 is fed into the input of the power amplifier 500. Power amplifier 500 is preferably a semiconductor based amplifier whose function is to amplify the power level at the output of first modulator 30 to a level that is sufficient to enable a plasma to be struck and to enable enough energy to be delivered into the plasma for the plasma to produce a useful clinical effect in terms of reducing or killing bacteria or viruses. Power amplifier 500 may comprise of a plurality of stages, i.e. driver stage, pre-amplifier stage and high power stage. The amplifier may use any of the following semiconductor devices: high frequency bipolar junction transistors (BJTs), heterostructure bipolar transistors (HBTs), metal oxide semiconductor field effect transistors (MOSFETs), or metal semiconductor transistors (MOSFETs). In terms of the semiconductor materials that may be used, of particular interest is gallium arsenide (GaAs) and gallium nitride (GaN).

GaN FETs offer a higher efficiency (microwave power/DC power) over GaAs FETs. This feature is of particular interest when developing a plasma system that is capable of providing high power microwave energy since the heating effects caused by the DC power loss are reduced, which increases the portability of the system and minimises the thermal design issues that need to be overcome when developing the system.

For applications relating to hospital ward sterilisation or other applications where a patient is not directly involved with the plasma treatment, it may be required to create a large amount of plasma. For example, to cover a section of the floor of a hospital ward, or to sterilise a mattress of a hospital bed, that may be infected with the MRSA virus. In such embodiments of the invention, it may be desirable to use an array of plasma plumes generated using coaxial transformer arrangements similar to those use for treating other clinical applications identified above, but the source of microwave power may be derived from a higher power microwave energy generating device such as a magnetron or a klystron, travelling wave tube (TWT), twystron (hybrid combination of a klystron driver and TWT output section in tandem in the same envelope), or a gyrotron. It is more difficult to control the level of power produced by these devices than it is when using semiconductor devices, but this may not be a problem when the plasma produced by the device is not in direct contact with patient tissue. For example, pulsed power levels in excess of 10 mega watts (MW) have been obtained using the twystron and multicavity klystrons.

It is desirable to be able to switch the main device power supplies (drain supply in FETs and the collector supply in BJTs) off during periods when it is not required to produce microwave power, i.e. when the switch contact of first modulator 30 is in the off position. A second modulator 130 may be employed to perform this function. Said second modulator 130 may comprise of a plurality of lower frequency power MOSFET or BJT switches that enable the DC power supplies to be connected to the high frequency power BJTs or FETs when it is required to generate microwave power to produce the plasma. The operation of the lower frequency power devices that form second modulator 130 can be controlled by varying the gate voltage or base current of the power FETS or power BJTs respectively. The control signals are provided by microprocessor 140 and the signals used to control the operation of second modulator 130 may be synchronised to the control signal used to control the operation of first modulator 30. Second modulator 130 will have a slower response time than that of first modulator 30, therefore, it may be desirable to modulate or pulse using first modulator 30 inside a window when second modulator 130 is enabled or switched on. For example, second modulator 130 may be switched on for a time slot of 100 ms and off for a time slot of 1 second; during the on period, first modulator 30 may produce 50 pulses with an on time of 1 ms and an off time of 1 ms. First modulator 30 and second modulator 130 enable the energy produced by the plasma to be controlled to ensure that the temperature of the plasma and the plasma energy is controlled to enable optimal clinical effects in terms of killing or the reduction of bacteria and/or viruses to be achieved.

The output from microwave power amplifier 500 is fed into the input port of microwave power circulator or power isolator 50, whose function is to ensure that high levels of reflected microwave power, due to impedance mismatches at antenna 300 or anywhere else in the path between the antenna 300 and the input port to first forward power coupler 60, i.e. 200, 90, 80, 100, and 70, cannot damage the output stage of power amplifier 500. In the arrangement shown in FIG. 1, a 50Ω power dump load 51 is shown connected to the third port of microwave power circulator 50. Any power that does get reflected back along the aforementioned path between antenna 300 and first coupler 60 will be absorbed by said power dump load 51.

The output port of the microwave power circulator 50 is connected to the main line input port of first forward power directional coupler 60, whose function is to sample a portion of the forward going power produced by power amplifier 500. This information may be used to control the level of microwave power produced by power amplifier 500 to ensure that the demanded power level is the same as the delivered (actual) power level, i.e. this information may be used in a feedback control loop to automatically adjust the input power going into the amplifier to compensate for output power drift caused by heating or ageing of microwave components used in the line-up. The information provided by first forward going directional coupler 60 may also be used to control the position of the stubs used in the stub tuning network (or tuning filter) 100.

The main line output from first forward power directional coupler 60 is connected to the main line input port of first reflected power directional coupler 70, whose function is to sample a portion of the reflected power that comes back from the input port of tuning filter 100 due to an impedance mismatch caused either by the position of the tuning elements or the impedance set-up inside the tuning filter or the impedance set up by antenna 300 in accordance with the state of the plasma, and the impedance transformations set up inside the applicator. The information provided by first reflected power directional coupler 70 may also be used to control the position of the stubs used in the stub tuning network (or tuning filter) 100. This information may also be used to as a part of a safety mechanism to detect the condition of the microwave components used in the line-up. In an alternative arrangement, the first forward power directional coupler 60 may be provided before the circulator and the first reflected power directional coupler 70 may be provided between the third port of the circulator 50 and the power dump load 51. This arrangement is advantageous because each of the sampled signals has only one component (forward or reflected).

The main line output from first reflected power directional coupler 70 is connect to the input port of tuning filter (impedance adjustor) 100, whose function is to set-up a condition that will enable the impedance of applicator 300 to be such that the plasma can be struck and then maintained. The condition for the plasma to be struck is a high voltage (high impedance) condition and that for it to be maintained is a high current (high current) condition. The tuning filter 100 may be a stub tuner that contains a single or a plurality of tuning rods or stubs, or may be an arrangement of power varactor or PIN diodes, where the bias voltage is changed to enable the capacitance to be varied. This capacitance variation is used to enable the tuned conditions to be set up based on the plasma state requirements. In the system shown in FIG. 1, a stub adjuster unit 110 is included; this is for a mechanical tuning mechanism where tuning rods are moved in and out of a cavity, for example, a waveguide cavity. Three tuning stubs are shown here, but this invention is not limited to the use of three, i.e. one, two, or four may be used. Three stubs may be preferable due to the fact that this arrangement will enable any impedance from an open circuit to a short circuit to be set-up inside the tuning cavity. The signals used to control the stub adjuster comes from microprocessor 140, and these signals may be based on the signals produced by detection unit 120 in accordance with the information available at the coupled ports of directional couplers 60, 70, 80, and 90. The control signals provided to stub adjuster 110 may also be in the form of two fixed signal formats; a first to create a known high impedance condition that is used to strike the plasma, and a second to create a known low impedance condition to maintain the plasma. The dynamic adjustment of the tuning stubs may also be used to optimise and control the plasma energy.

It should be noted that a PID controller could be used between microprocessor 140 and stub adjuster 110 to control the response of the electromechanical stub adjuster 110. Alternatively, the PID control functions may be handled by microprocessor 140. A further alternative is to replace the mechanical tuning system with a power PIN or varactor diode arrangement, whereby the bias voltage applied to the diodes is used to adjust the depletion layer within the diodes to produce a capacitance variation. A further alternative is to connect a variable capacitance in shunt to the power line.

The output port of the tuning filter is connected to the main line input of second forward power directional coupler 80, whose function is to sample a portion of the forward going power coming out of tuning filter 100. This information may be combined with the information produced by the coupled port of first forward power coupler 60 (or used independently) to control the level of microwave power produced by power amplifier 500 to ensure that the demanded power level is the same as the delivered (actual) power level, i.e. this information may be used in a feedback control loop to automatically adjust the input power going into the amplifier to compensate for output power drift caused by heating, ageing of microwave components used in the line-up, or changes in the characteristics of tuning filter 100. The information provided by second forward going directional coupler 80 may also be used in the tuning algorithm to control the position of the stubs used in the stub tuning network (or tuning filter) 100.

The main line output from second forward power directional coupler 80 is connected to the main line input port of second reflected power directional coupler 90, whose function is to sample a portion of the reflected power that comes back from microwave cable assembly 200 due to an impedance mismatch caused the impedance of plasma applicator 300, which varies in accordance with the state of the plasma. The information provided by second reflected power directional coupler 90 may also be used to control the position of the stubs used in the stub tuning network (or tuning filter) 100. This information may also be used as a part of a safety mechanism to detect the condition of the microwave components used in the line-up, i.e. used to detect a break in the line-up or another defect.

The main line output from second reflected power directional coupler 90 is connected to the proximal end of microwave cable assembly 200, whose function is to transport microwave energy used to strike and maintain the plasma from the controllable microwave generator to plasma applicator 300. Microwave assembly 200 may take the form of a coaxial cable designed to support propagation of microwave energy at the frequency of interest, or any other low loss structure, for example, flexible or flexible/twistable waveguide.

The distal end of microwave cable assembly 200 is connected to the proximal end of plasma applicator 300, whose function is to take in the microwave energy and the gas (or gas mixture) into the device to produce plasma that is suitable for reducing or destroying bacteria or a range of viruses at the proximal end. The plasma applicator shown in FIG. 1 comprises a first impedance transformer 310-330, a second impedance transformer 320-330, a microwave input connector 340, a means of coupling the pipe or tube that supplies the gas mixture 470 into plasma applicator 300, and a plasma generation region 350.

The sampled forward and reflected power levels (or signals) available at the coupled ports of directional couplers 60, 70, 80, and 90 are fed into detection unit 120, whose function is to enable either amplitude or amplitude/phase information to be available at microprocessor 140, where this amplitude or amplitude/phase information is extracted and used to control tuning filter 100. The information from the coupled ports of directional couplers 60, 70, 80, and 90 may be routed to detection unit 120 using a four pole single throw PIN switch or a coaxial switch controlled by signals produced by microprocessor 140 to enable one detector to be used to process the information produced by the four couplers.

The detection unit 120 may take the form of a diode detector, a homodyne detector or a heterodyne detector. The diode detector may take the form of a tunnel diode, a Schottky diode or any other diode that can be operated as a rectifier at the frequency of interest to provide amplitude or magnitude information relating to the forward and reflected power levels at the directional couplers 60, 70, 80, 90. The homodyne detector may take the form of a microwave mixer and a local oscillator that operates at the same frequency as the signal produced by microwave oscillator 10 to enable base band information to be extracted. The heterodyne detector may take the form of at least one microwave frequency mixer and at least one local oscillator. In this configuration the local oscillator frequency or frequencies may be different from that of microwave oscillator 10. This arrangement may also contain band pass and low pass filters to filter out signals at unwanted frequencies contained within the intermediate frequency signal (IF) produced at the output of the microwave frequency mixer and to remove signals produced at the local oscillator frequency or at the main microwave oscillator frequency 10 when they occur within the microwave line-up in locations where they are unwanted.

Controller 140 (e.g. microprocessor) is used to control the operation of the plasma generation system. It is responsible for controlling the operation of the following components used in the system: power level controller 20, first modulator 30, second modulator 130, gas mixer 400, flow switches 430-440, flow adjust controllers 450-460, compressed air generator 420, stub adjuster 110, and the user interface 150. It also reads the signals produced by detection unit 120 and uses this information to calculate the adjustments required by the tuning stubs via stub adjuster 110. Microprocessor unit 140 also determines when the mixture of gas required and the flow rate based on the required application. It is necessary to determine when to introduce the gas mixture into the plasma applicator in relation to the microwave energy. It is desirable to ensure that the applicator is filled with gas prior to introducing the microwave energy in order to ensure that the plasma is struck as soon as the microwave source is activated. It is also desirable to ensure that the correct or optimal conditions are set up inside the stub tuner prior to the microwave source being activated.

Operation of the system may be as follows:
  set stubs into a position where a known high impedance will be produced at the distal end of second conductor of second impedance transformer 320;
  determine the gas flow rate, the gas mixture, and the pulsing sequence required to produce optimal plasma for the particular application;
  determine the level of microwave power and the modulation format required to produce optimal plasma for the particular application;
  introduce the gas mixture into the applicator;
  after a period of time when it is assured that the applicator is full of gas introduce the microwave energy into the applicator.

When the system is being operated in pulse mode, it may be desirable to stop the gas flow during the time that the microwave source is in the 'off' state and start it again just before switching the microwave energy back on again. For example, the microwave power may be delivered using a 10% duty cycle where the on time is 10 ms and the off time is 90 ms. In this instance, it may be desirable to start the gas flow 5 ms before the start of the microwave pulse and turn it off 5 ms after the microwave pulse has been switched off, thus for each 10 ms of microwave energy the gas will flow for 20 ms, thus for a 10% duty cycle of microwave power, the duty cycle for the gas supply will be 20%.

It may be desirable to stop the gas flow at the same time as turning the microwave power off since it will take a finite time for the gas to cease flowing.

It may also be necessary to initially start the gas flow for a longer period of time in order to be sure that the gas has reached the applicator and has had enough time to enable it to fill the inside of the applicator.

A further function of controller 140 may be to activate alarms and handle safety features and system shut down procedures in the instance when a fault occurs. It may be necessary to use a second microprocessor unit or a similar device that can be used as a watchdog for handling safety critical features.

Controller 140 may take the form of a single board computer, a microcontroller (or PIC device) a single board computer and a PIC device (used as a watch dog), more than one single board computer, more than one PIC device, a digital signal processor, or any combination of these devices.

The user interface 150 provides a means of allowing the user to control the system and to provide information to the uses regarding the status and operation of the system. The user interface may be in the form of a touch screen display, a flat LCD display and a set of membrane keys, or any other means of outputting and inputting user control information.

The sub-system responsible for the control of the gas mixture comprises of at least one gas cylinder 410 and/or a compressed air generator 420, a means of controlling the rate of flow of the gases 430, 450, 440, 460, and a means of mixing the gases together. The rate of gas flow may be controlled using a flow valve with a flow controller in combination with a suitable flow switch, which may be a solenoid switch. In specific embodiments of the invention the flow switches 430, 440 may not be implemented and the flow adjustment may be implemented only flow adjust controllers 450, 460. On the other hand, flow adjust controllers 450, 460 may be omitted and flow control may be implemented by mechanical adjustment of the valve connected to the particular gas cylinder 410 combined with electrical control of flow switch 430, 440. In the instance when a compressed air generator 420 is used, it may be possible to operate the system using only flow switch 440. Gas mixer 400 may be required where more than one type of gas is used and it is necessary to optimise the mixture or vary the mixture during operation.

Gas mixer 400 may take the form of a pneumatic device which works by balancing pressures from the input gas supplies to ensure that the component gases are mixed at the same pressure regardless of their individual inlet pressures and flow rate. The gases may be combined in a chamber fed by variable orifices, which are set by the mixing control. The mixers may be factory set for the gases specified. For example, in a two gas system the mix control can be calibrated directly in proportionality 0-100%—gas1/gas2. This single control sets up the required mix. In a three gas mixer, where there are two proportional regulators, the proportionality may be set with two controls to set the total mix.

Where the flow is intermittent, i.e. for pulsed operation, a special control valve may be required to ensure accurate feeding of a ballast tank. Built in alarms and sensors may be added to monitor the pressure conditions in the mixer to ensure correct mixing conditions.

The operation of the gas mixer 400, the flow switches 430, 440, the flow adjust controllers 450, 460, and the compressed air generator 420 is controlled using microprocessor 140, and adjustment of these devices may take place using a closed loop feedback system where the adjustments are based on the feedback signals from detection unit 120.

Clinically useful plasma can be produced using a mixture of helium and compressed air and so this arrangement is given in FIG. 1. It is believed that the useful component of the compressed air is oxygen and that the mix of helium and oxygen can be used to reduce or kill certain types of bacteria or viruses.

Figure 2:
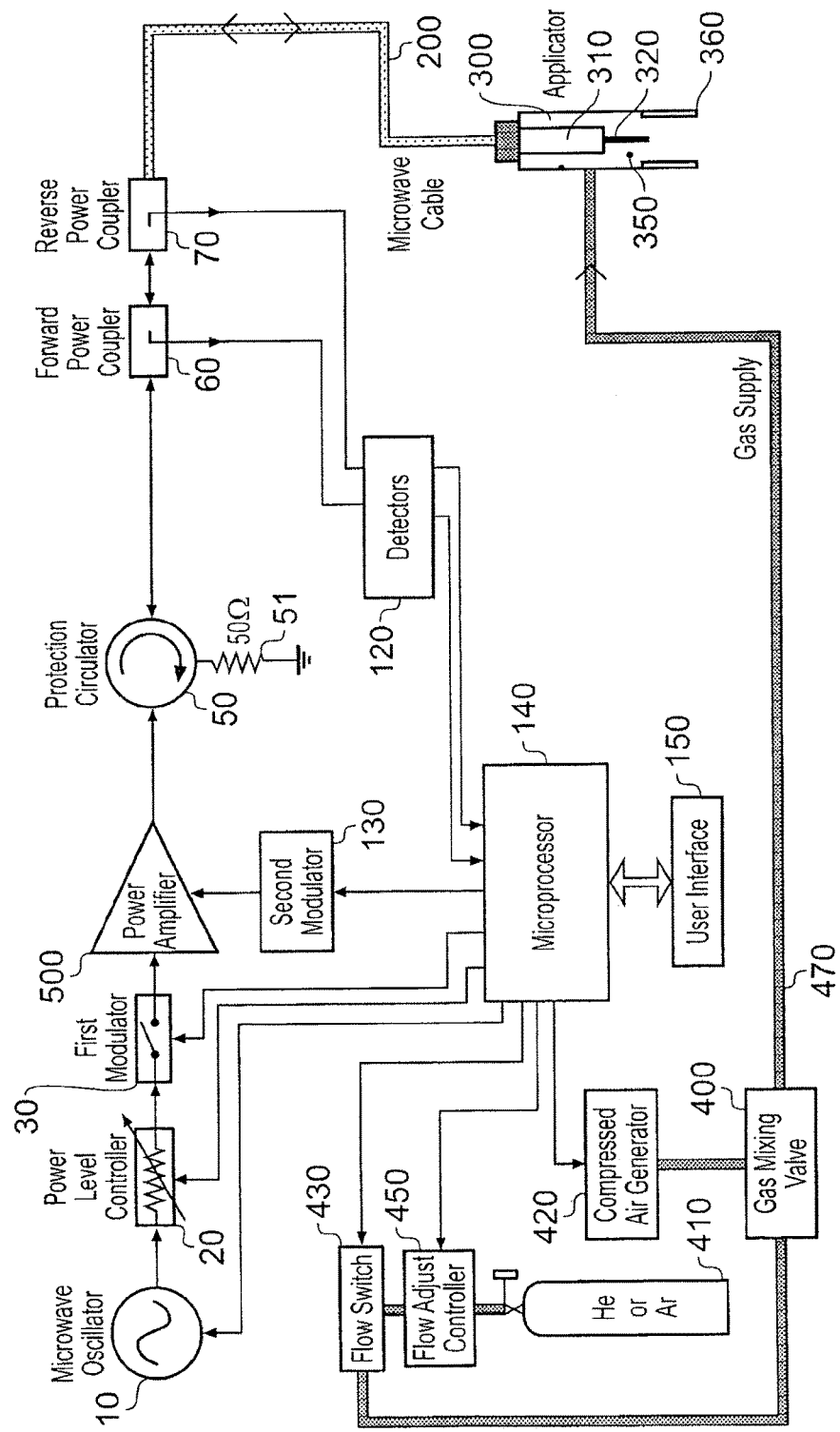
FIG. 2 is a block diagram showing a plasma sterilisation system that is an embodiment of the invention without an impedance adjustor.

FIG. 2 shows an arrangement for the plasma system where the plasma is struck and maintained without the use of tuning filter 100, and stub adjuster 110. In this instance, applicator 300 may be arranged to produce a high enough electric field to enable the plasma to be struck. The microwave energy is then delivered as a train of pulses, where each pulse produces a plasma strike to enable a quasi continuous plume of plasma to be generated. The pulse repetition rate and the pulse length may be used to determine the plasma energy and this may be optimised to enable the desired amount of bacteria to be destroyed. Due to the need to only monitor the forward and reflected power between the output of power circulator 50 and the input to microwave cable assembly 200, only two couplers 60, 70 are required. A quartz tube 360 at the outlet of the plasma application 300 is also shown in FIG. 2.

Figure 3:
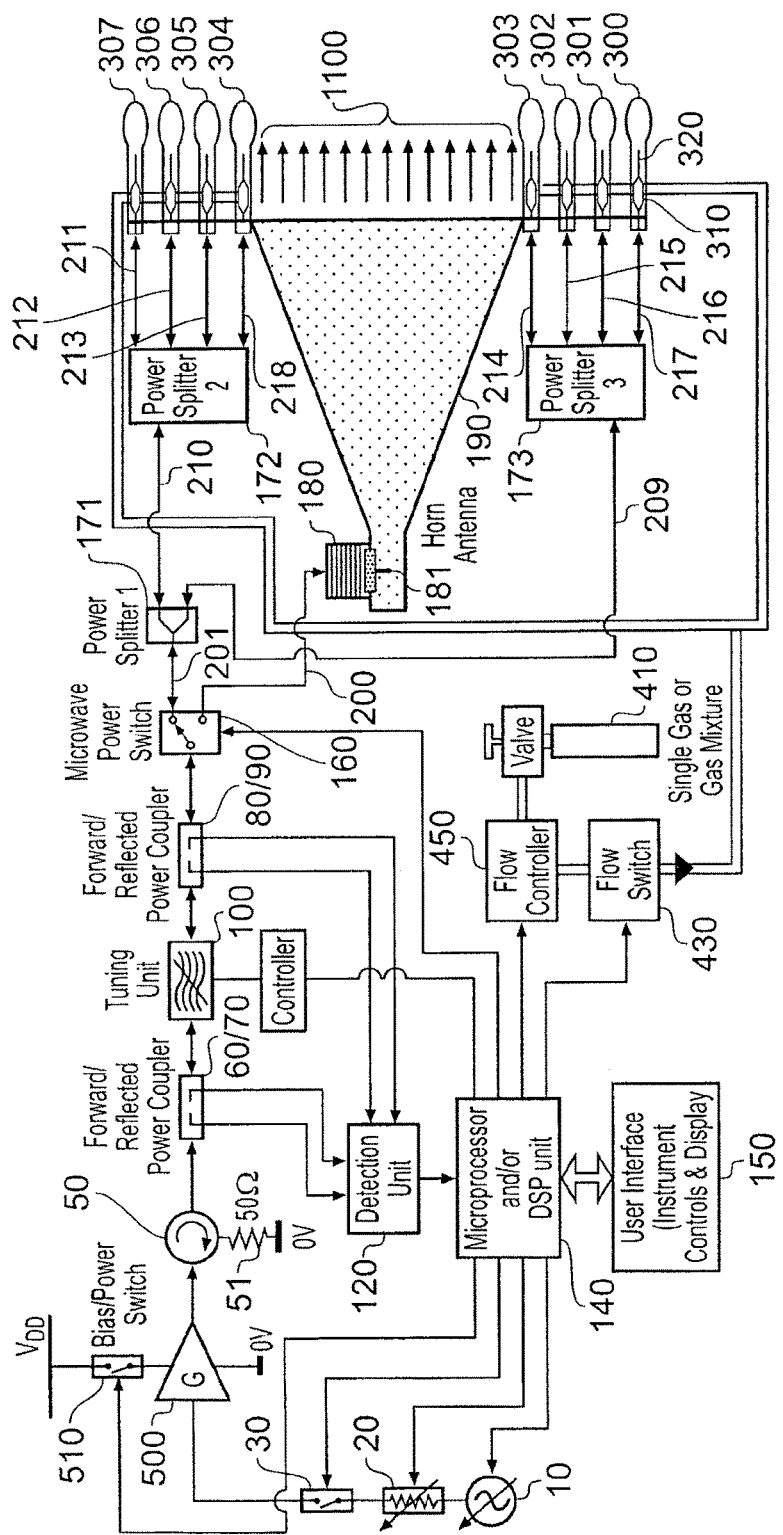
FIG. 3 is a block diagram of a plasma sterilisation system that is an embodiment of the invention that is also arranged to emit non-ionising radiation.

FIG. 3 shows a block diagram of a plasma sterilisation system that is another embodiment of the invention. Elements in common with FIGS. 1 and 2 are given the same reference number and insofar as they perform the same function are not described further. The embodiment in FIG. 3 is arranged to selectively emit either plasma (produced in a similar way to the embodiments shown in FIGS. 1 and 2) or non-ionising microwave energy.

In FIG. 3, the second modulator is embodied as a power switch 510 arranged to connect a DC power source as an activation signal to the amplifier 500.

To permit the selection of plasma emission or microwave energy emission, the output of the microwave generator, which in this arrangement is the output of the tuning unit 100 that passed through forward and reverse couplers 80/90, is connected to a microwave power switch 160, which may be a conventional two-pole-single-throw switch. In the configuration shown in FIG. 3, the switch 160 conveys the microwave energy to a power splitting arrangement 171, 172, 173, whose function is to split the input microwave energy into a plurality of feed lines 211, 212, 213, 214, 215, 216, 217, 218 each of which deliver microwave energy to a respective plasma applicator 300, 301, 302, 303, 304, 305, 306, 307.

In this embodiment the output 201 from the first terminal of the switch 160 is input to a first power splitter 171, which may be a conventional 3 dB power splitter, which divides into two intermediate signals 209, 210. Each intermediate signal 209, 210 is connected to a respective four way power splitter 172, 173 which divides it into four input signals, one for each plasma applicator. Each plasma applicator may have a configuration similar to that described above or as described below with reference to FIG. 5.

If it is desirable to emit microwave radiation, e.g. to enable the sterilising energy to penetrate a surface to sterilise the region underneath it, the switch 160 may adopt a second configuration in which the microwave energy is directed to output 200. Output 200 is connected to the input port of a horn antenna 190 which is shaped to direct a beam 1100 of microwave energy out of the apparatus. The output 200 may be connected to a dipole antenna 181 located in the base of the horn antenna 190 via an SMA connector 180 or the like.

Figure 4A:
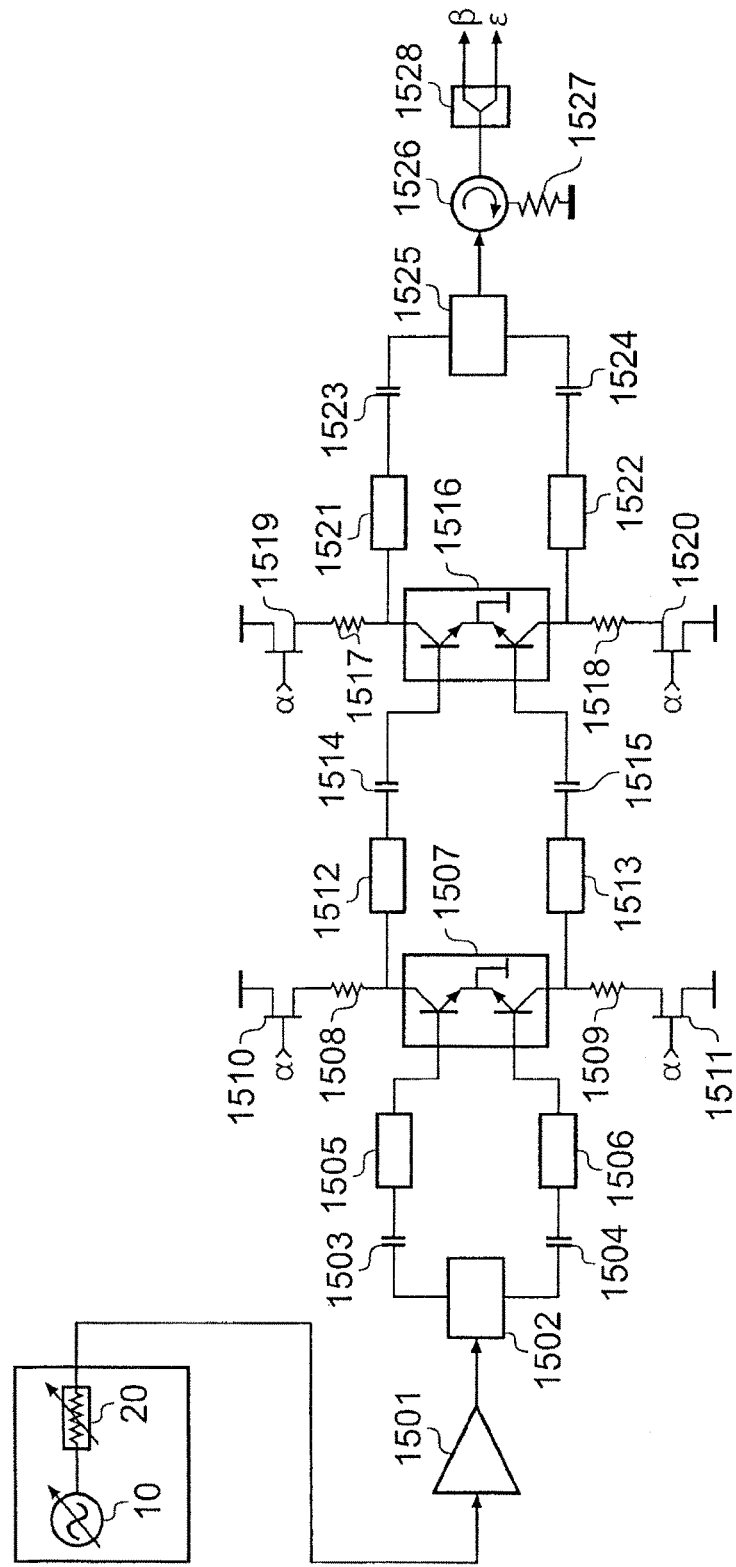
FIGS. 4a, 4b and 4c are block circuit diagrams showing the amplifier control circuitry.
Figure 4B:
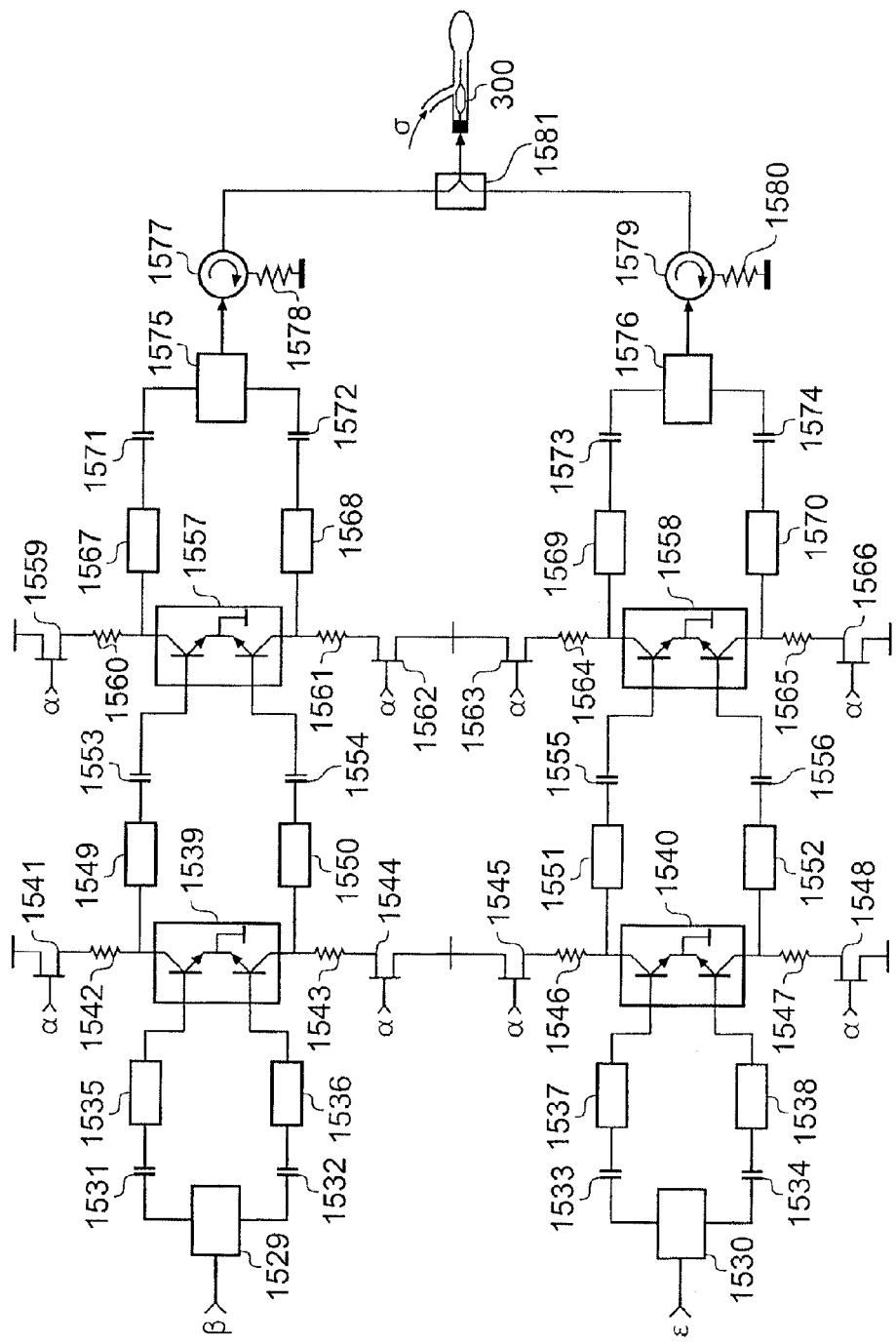
Figure 4C:
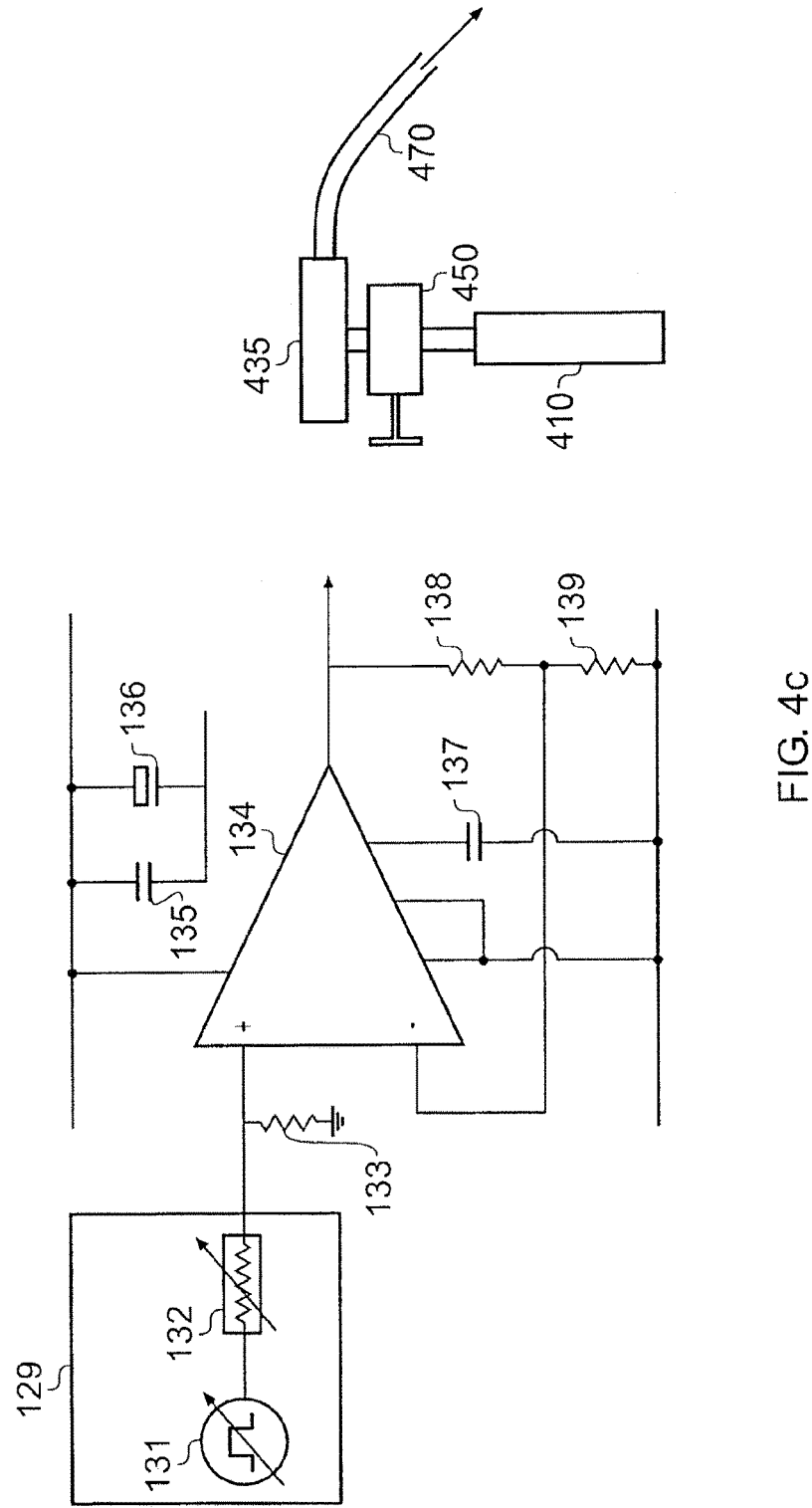

FIGS. 4a, 4b, and 4c provide details of a component line of a specific embodiment of the invention. This embodiment may enable up to 300 W of adjustable and controllable microwave power to be produced. This microwave power can be pulsed or modulated within the frequency range of between DC and 100 kHz, and enables the duty cycle to be varied from between 1% and 99%. The embodiment described here also offers the flexibility of being able to manually adjust the microwave frequency within the range of between 850 MHz and 950 MHz.

FIGS. 4a and 4b in particular illustrate a specific implementation of the amplifier 500 using power transistors, e.g. Motorola bipolar NPN power transistors MRF988 and MRF897. To generate 300 W of microwave power using these devices, two MRF899 power transistors were driven using two of the MRF897 power devices. The collector voltages used on the MRF899 devices was limited to 26 V DC maximum, and the collector voltages used on the MRF897 devices was limited to 24 V DC maximum.

In detail, FIG. 4a shown the source 10 and power control attenuator 20, which may be provided together by an Agilent E8247C 250 kHz to 20 GHz PSG CW signal generator (whose maximum output power level is 16 dBm). The signal from this generator is amplified to provide a maximum drive signal of 32 dBm at 866 MHz using an HMC4535T89 Hittite MMIC 1501 that has a gain of 20 dB at the frequencies of interest here. The output from MMIC 1501 is fed into the first stage of the power amplifier. The first component in the power amplifier line-up is balanced to unbalanced converter (balun) 1502, which is fabricated onto microstrip and enables the unbalanced signal from MMIC 1501 to be converted into two balanced signals used to drive first power transistor 1507. The first output from balun 1502 is connected to first DC blocking capacitor 1503 and the second output from balun 1502 is connected to second DC blocking capacitor 1504. The function of blocking capacitors 1503, 1504 is to block any DC signals that maybe present at the output terminals of balun 1502. The outputs from DC blocking capacitors 1503, 1504 are fed into first and second impedance transformers 1505, 1506 respectively. The function of these impedance transformers is to provide impedance matching between the two outputs from balun 1502 and the two base inputs to power transistor 1507. The impedance matching transformer may be a quarter wave matching transformer realised in microstrip or a quarter wave transformer together with a stub. The latter is used to provide a conjugate match between the source impedance (outputs from balun 1502) and the load impedance (base inputs). Power transistor 1507 comprises of two NPN power transistors connected in a push-pull configuration where the bases are driven in anti-phase to provide a balanced output with twice the voltage of a single stage, which leads to four times the power from that of a single stage. In the configuration shown in FIG. 4a, the two emitters are connected together and held at ground potential, and the two collector supplies have series inductors 1508, 1509 connected to them to block any high frequency signals (i.e. 866 MHz) from getting back into the DC power supply. The two collector terminals are connected to MOSFET power switches 1510, 1511, which are used to control the DC power applied to the power devices. The input gate signal ($\alpha$) switches on the power MOSFETs 1510, 1511 only when it is necessary to generate microwave power. The arrangement of gate switches and the control circuitry forms second modulator 130. The power transistor used in this first stage is the MRF897 30 W part described above.

The second stage comprises of a similar arrangement where the two output collectors from power transistor 1507 are connected to impedance transformers 1512, 1513 and DC blocking capacitors 1514, 1515 and the two output signals from DC blocking capacitors 1514, 1515 are used to drive the two bases of second microwave power transistor 1516. The power transistor used in this second stage is the MRF899 150 W part described above. The second stage operates as above, with the series inductors 1517, 1518 and MOSFET power switches 1519, 1520 performing functions similar to the series inductors 1508, 1509 and MOSFET power switches 1510, 1511 of the first stage.

The outputs taken from the two collector terminals of second microwave power transistor 1516 are connected to impedance transformers 1521 and 1522, whose function is to transform the low impedance collector outputs to the impedance of standard microwave components and transmission line structures, i.e. 50Ω. The output from impedance transformers 1521 and 1522 is fed into DC blocking capacitors 1523 and 1524, which are used to remove any DC voltage level or DC bias from the signal. The outputs from DC blocking capacitors 1523, 1524 are fed into a second balun 1525, whose function is to convert the balanced signals produced by the two collector outputs of power transistor 1516 into an unbalanced single ended signal. The output from second balun 1525 is fed into the input port of power circulator 1527, whose function is to protect the collector outputs of power transistor 1516 from damage due to high levels of reflected power coming back into the device due to an impedance mismatch produced somewhere along the microwave line-up. A 50Ω power dump load 1527 is connected to the third port of power circulator 1526. This load is used to dissipate the reflected power and so must be able to withstand the maximum level of reflected power without overheating. The dump load 1527 may be connected to a solid thermal mass, i.e. a block of aluminium or brass where the power can be dissipated. A fan may be provided to cool dump load 1526. The output port of power circulator 1526 is connected to the input of first power splitter 1528, whose function is to split the power emerging from the output port of power circulator 1526 into two parts. The power splitter 1528 may split the power level into two equal parts.

The two outputs from power splitter 1528, denoted as $\beta$ and $\in$, are each connected to a third stage of the power amplifier, as shown in FIG. 4*b*. The third stage corresponds to the first stage, i.e. includes two 30 W MRF897 devices 1539, 1540 separately driven using signals $\beta$ and $\in$ generated at the previous stage. Accordingly, first input $\beta$ is connected to a third stage comprising balun 1529, DC block capacitors 1531, 1532, impedance transformers 1535, 1536, power transistor 1539, series inductors 1542, 1543 and MOSFET power switches 1541, 1544 which operate according to the same principles as corresponding components described above with respect to the first stage. Similarly, second input $\in$ is connected to a third stage comprising balun 1530, DC block capacitors 1533, 1534, impedance transformers 1537, 1538, power transistor 1540, series inductors 1546, 1547 and MOSFET power switches 1545, 1548.

The pair of collector outputs from each of the two third stages mentioned above are connected to a respective fourth stage having a power transistor comprising two of the 150 W MRF899 devices. The fourth stage for the pair of collector outputs derived from the first input $\beta$ comprises impedance transformers 1549, 1550, DC blocking capacitors 1553, 1554, power transistor 1557, series inductors 1560, 1561 and MOSFET power switches 1559, 1562 which operate according to the same principles as corresponding components described above with respect to the second stage. Similarly the fourth stage for the pair of collector outputs derived from the second input $\in$ comprises impedance transformers 1551, 1552, DC blocking capacitors 1555, 1556, power transistor 1558, series inductors 1564, 1565 and MOSFET power switches 1563, 1566.

The outputs taken from the two collector terminals of the power transistor 1557 are connected to impedance transformers 1567 and 1568, whose function is to transform the low impedance collector outputs to the impedance of standard microwave components and transmission line structures, i.e. 50Ω. The output from impedance transformers 1567 and 1568 is fed into DC blocking capacitors 1571 and 1572, which are used to remove any DC voltage level or DC bias from the signal. The outputs from DC blocking capacitors 1571, 1572 are fed into a balun 1575, whose function is to convert the balanced signals produced by the two collector outputs of power transistor 1557 into an unbalanced single ended signal. The output from balun 1575 is fed into the input port of power circulator 1577, whose third port is connected to 50Ω power dump load 1578 to enable it to perform a similar function to circulator 1526 discussed above.

Similarly, the balanced signals output from the two collector terminals of the power transistor 1558 are converted into an unbalanced single ended signal by using impedance transformers 1569, 1570, DC blocking capacitors 1573, 1574 and balun 1576. The output from balun 1576 is fed into the input port of power circulator 1579, whose third port is connected to 50Ω power dump load 1580 to enable it to perform a similar function to circulator 1526 discussed above.

The two outputs from power circulators 1577 and 1579 are connected to the inputs of power combiner 1581, whose function is to add the powers emerging from the two outputs of power circulators 1577 and 1579 to produce the sum of the two powers at one single output port. For this arrangement, the maximum output power monitored at the output port of power combiner 1581 may be 300 W. The output port of microwave power combiner 1581 is connected to plasma applicator 300 via a low loss microwave cable assembly (not shown here) and this power is used to strike and maintain the plasma.

FIG. 4*c* shows the arrangement used to implement second modulator 130 that provides the gate control signal ($\alpha$) to the power MOSFET switches discussed above. The second modulator comprises a waveform generator 129, e.g. an Agilent 33220A DC to 20 MHz waveform generator, which provides a variable frequency/wave shape source 131, and a means of controlling the amplitude and offset of the signal 132, and an amplifier/driver circuit. The amplifier/driver circuit amplifies the voltage level produced by the generator 129 to enable MOSFET devices to be turned hard on act as switches and to provide enough current to charge the gate capacitances to allow the devices to be turned on as fast as possible, i.e. the switching time dt=CdV/I, where C is the gate-source capacitance, dV is the change in gate voltage required to switch the device hard on, and I is the current available to charge the gate-source capacitance. It will be apparent that the only parameter that can be adjusted or changes is the current available to charge up the gate-source capacitance, for example, if the gate-source capacitance is 1000 pF and the required voltage excursion is 15 V, then with a current of 5 A is available, the device will be switched on in approximately 3 ns seconds, whereas if the current available was only 100 mA then the switching time would be 150 ns. This simple analysis does not take into account Miller effect capacitance, which will also slow down the switching time, but this decrease will occur in both cases. The driver circuit uses an OPA548T power operational amplifier 134, which is manufactured by Burr Brown. The operational amplifier 134 is configured as a non-inverting amplifier where the gain is determined by the values of resistors 138, 139. In this case, the gain of the circuit is 8.5 (i.e. 1+15/2). Capacitors 135 and 136 are used for decoupling the DC power supply and capacitor 137 is used to prevent any noise getting into the device through pin 7. Input resistor 133 sets the input impedance seen by the output of the waveform generator 129 to 1 kΩ. In the arrangement shown here, the waveform generator 129 and the driver circuit can modulate the microwave energy at a frequency of up to 100 kHz. It was found that the plasma plume changed with frequency, for example, using a 20% duty cycle, the plasma was found to be hotter when the modulation frequency was 5 kHz than it was at 500 Hz. In this arrangement, first modulator 30 was not used.

The second drawing shown in FIG. 4c is an arrangement used for enabling the gas mixture to be introduced into the plasma applicator. The arrangement includes a gas cylinder 410, which may be one of the inert gases Ni, $CO_2$, Ar, or He in compressed form, a flow adjuster 450 (valve), and a flow controller 435. The output from flow controller 435 is connected to feed pipe 470, which is connected to plasma applicator 300 (not shown). In one embodiment, feed tube 470 may be cut and a 4 mm pneumatic push-in union 'Y' fitting inserted with a first input connected to the compressed gas cylinder 410 via valve 450 and a second input connected to compressed air generator 420. This arrangement enabled the compressed air to be mixed with the helium and for the mixture to be fed into plasma applicator 300.

Figure 5:
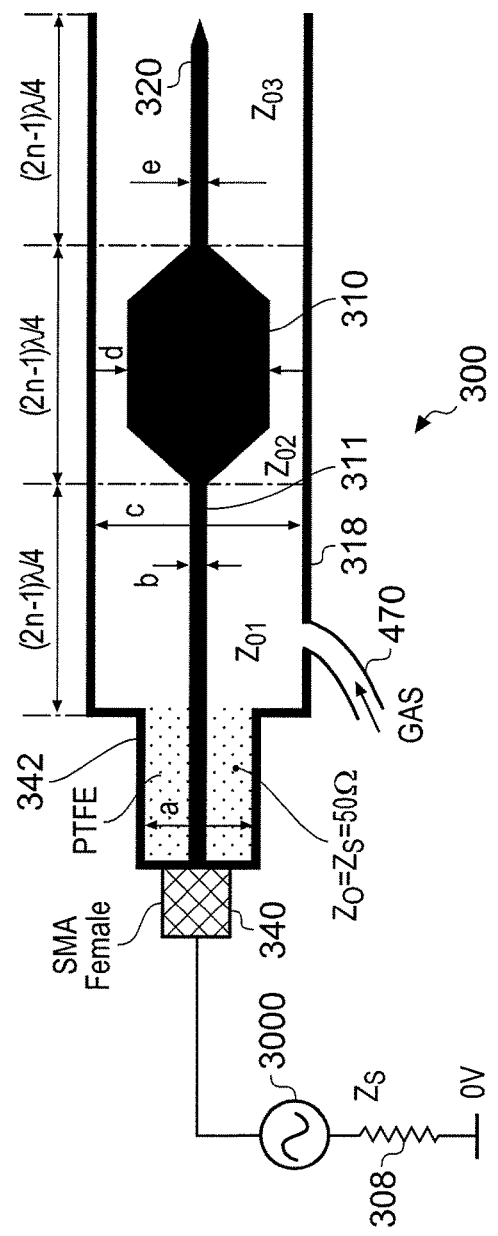
FIG. 5 is a schematic cross-sectional view of a coaxial plasma applicator suitable for use in the invention.

FIG. 5 is a longitudinal cross-sectional view through a coaxial plasma applicator that can be used with the invention. The plasma sterilisation apparatus need not be limited to use with this type of structure. Indeed this example is provided to explain the theory behind the use of voltage transformers (or impedance transformers) in the generation of plasma in the applicator. In fact it may be possible to generate the plasma without voltage transformers, especially if an impedance adjustor is present.

The plasma applicator 300 shown in FIG. 5 is a coaxial structure comprising three quarter wave impedance transformers, where the diameter of the centre conductor is changed to produce three sections with different characteristic impedances. The impedances are chosen such that the voltage at the distal end of the structure is much higher than the voltage at the proximal (generator) end of the structure.

If the physical length of each section is equal to an odd multiple of the quarter electrical wavelength, i.e.

$$L = \frac{(2n-1)\lambda}{4},$$

where L is length in metres, n any integer, and λ is wavelength at frequency of interest in metres, then the following equation applies $$Z_0 = \sqrt{Z_L Z_S},$$

where $Z_0$ is the characteristic impedance of the coaxial line in Ω, $Z_L$ is the load impedance seen at the distal end of the section in Ω, and $Z_S$ is the source impedance seen at the proximal end of the section in Ω. By algebraic manipulation of this equation, the load impedance can be expressed as $$Z_L = \frac{Z_0^2}{Z_S}.$$

It can therefore be seen that if the characteristic impedance of the transformer section is high and the source impedance is low then the load impedance can be transformed to a very high value.

Since the power level at the generator end of the antenna should theoretically be the same as that at the load end, the following can be stated $$P_{in} = P_{out} \Rightarrow P_{in} = \frac{V_L^2}{Z_L},$$

which means the voltage at the distal end can be expressed as $V_L = \sqrt{P_{in} Z_L}$. Thus it can be seen that if $Z_L$ can be made as large as possible then the value of the voltage at the distal end of the antenna structure $V_L$ will also be very large, which implies that the electric field will also be high. Since it is required to set up a high electric field in order to strike the plasma, it may be seen that this structure can be used to set-up the correct conditions to strike the plasma.

Considering the structure shown in FIG. 5, the microwave generator 3000 is indicated schematically as having a source impedance ($Z_S$) 308. The power from the generator 3000 enters the applicator 300 via microwave cable assembly (not shown) using microwave connector 340. Connector 340 may be any microwave connector that is capable of operating at the preferred frequency of operation and can handle the power level available at the output of power generator 3000, e.g. N-type or SMA type connectors may be used. Microwave connector 340 is used to launch the microwave power into the plasma generating region, which includes an antenna structure described below.

The first stage of the antenna structure is a 50Ω coaxial section that consists of a centre inner conductor with an outside diameter b and an outer conductor with an inside diameter a. The space between the inner and outer conductors contained within the first section is filled with a dielectric material 342, which is labelled here as PTFE. The characteristic impedance of the first section of the antenna is shown here to be the same as that of the generator, i.e. 50Ω, and can be described as follows $$Z_0 = Z_S = \frac{138}{\sqrt{\varepsilon_r}} \log_{10} \frac{a}{b} = 50 \text{ Ω},$$

where $\in_r$ is the relative permittivity of the filler material, $Z_0$ is the characteristic impedance of the first section and $Z_S$ is the source impedance (or the generator impedance).

The second section is the first quarter wave impedance transformer 311 whose characteristic impedance $Z_{01}$ is higher than that of the first section and can be calculated using $$Z_{01} = 138 \log_{10} \frac{c}{b},$$

where c is the inside diameter of the outer conductor 318. Since the second section is filled with air (or at least the gas from gas feed 470), the relative permittivity c, is equal to unity and so the square root term disappears from the equation that describes the impedance of a coaxial transmission line. A practical example of the impedance of the second section may be b=1.63 mm and c=13.4 mm. With such dimensions, $Z_{0l}$ would be 126.258Ω.

The third section is the second quarter wave impedance transformer 310, whose characteristic impedance $Z_{02}$ is lower than that of the first section and second sections, and can be calculated using $$Z_{02} = 138 \log_{10} \frac{c}{d},$$

where d is the outer diameter of the inner conductor. It is desirable to taper the input and output ends of the centre conductor in order to make the step from the high impedance condition to the low impedance condition more gradual in order to minimise mismatches occurring at the junctions between the two impedances. A suitable angle for the taper is 45°. A practical example of the impedance for the third section may be d=7.89 mm and c=13.4 mm. With such dimensions, $Z_{02}$ would be 31.744Ω.

The fourth section is the final section and consists of a third quarter wave impedance transformer 320, whose characteristic impedance $Z_{03}$ is higher than that of the third section, and can be calculated using $$Z_{03} = 138 \log_{10} \frac{c}{e},$$

where e is the outer diameter of the inner conductor. It is desirable for the distal end of the inner conductor to be sharp and pointed in order to maximise the magnitude of the electric field produced at this point. A practical example of the characteristic impedance for the fourth section may be e=1.06 mm and c=13.4 mm. With such dimensions, $Z_{03}$ would be 152.048Ω.

For the arrangement using three quarter wave transformers as shown in FIG. 5, the load impedance $Z_L$ seen at the distal end of the antenna may be expressed as $$Z_L = \frac{Z_{03}^2 Z_{01}^2}{Z_{02}^2 Z_S}.$$

Using the values of characteristic impedance calculated above for the three transformers, $Z_L$ would be 7,314.5Ω.

If the input power is 300 W, then the voltage at the output will be $V_L = \sqrt{P_{in} Z_L} = 1,481.33$ V. The electric field generated at the end of this structure will thus be $$E = \frac{2V_L}{c} = 221,094.03 \ Vm^{-1}.$$

This large electric field may enable the plasma to be set up using any one of a number of gases and gas mixtures.

The inner conductor may be a single conductor whose diameter changes from b to d to e from the proximal end to the distal end. The outer conductor has the same inner diameter c for the length of the three impedance transformer sections and is reduced to a at the first section. The material used for the inner and outer conductors may be any material or composite that has a high value of conductivity, for example, copper, brass, aluminium, or silver coated stainless steel may be used.

The gas or mixture of gases is fed into the structure using feed tube 470 and the gas fills the inside of the coaxial assembly.

Figure 6:
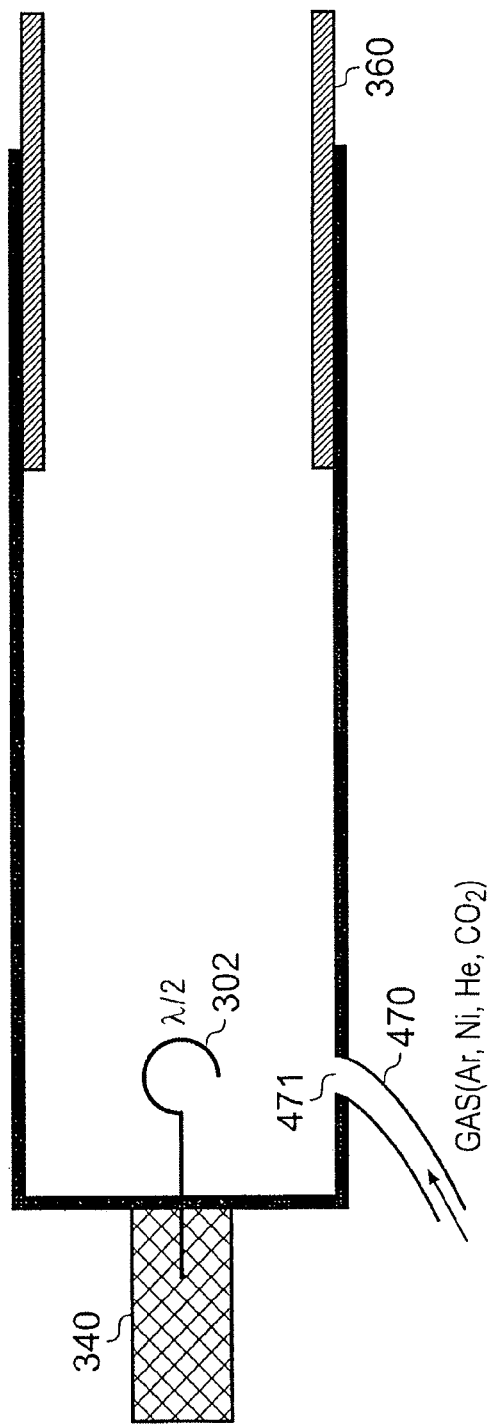
FIG. 6 is a schematic cross-sectional view of a waveguide plasma applicator suitable for use in the invention.

FIG. 6 shows a plasma applicator 300 in which a waveguide cavity is used to create the field to generate the plasma. In this particular embodiment, an H-field loop 302 is used to transfer the microwave energy from the microwave generator into the waveguide antenna, and the gas mixture is introduced into the structure via gas feed 471, which is connected to feed tube 470. It may be preferable for H-field loop to have a physical length that is equal to half the wavelength at the frequency of interest or operation, and for the distal end of said loop to be connected to the inside wall of outer conductor. The connection may be made using a weld or solder joint.

Although not illustrated in FIG. 6, impedance transformers may also be introduced into the waveguide embodiment to generate high electric fields at the distal end of the applicator in a similar manner to those introduced using the coaxial arrangements described above. In other words, the waveguide antenna may comprise of a plurality of sections that have a length equal to an odd multiple of the quarter loaded or unloaded wavelength at the frequency of interest, i.e.

$$L = \frac{(2n-1)\lambda}{4}.$$

In order to reduce the dimensions of the waveguide (length, width, or diameter) the waveguide may be filled with a dielectric, or magnetic, or composite material where the wavelength is reduced by a function of the inverse of the square root of the relative permittivity, or the relative permittivity, or the product of the two. A number of impedance transformers may be introduced by loading one or a plurality of the sections that form the transformer. In the instance whereby the waveguide structure is loaded with a dielectric or magnetic material (or combination of the two), it may be preferable for the loading material to be porous or have a plurality of holes drilled into it to enable the gas or gas mixture to flow inside the waveguide sections.

In order to change the impedance of the waveguide to produce the desired quarter wavelength transformations within the structure, it is necessary to make adjustments to the geometry of the structure or change the loading material.

For a rectangular waveguide, the characteristic impedance of the waveguide cavity may be expressed as $$Z_0 = 377 \frac{b}{a} \sqrt{\frac{\mu_r}{\varepsilon_r} \frac{\lambda_g}{\lambda}},$$

where $$\frac{\lambda_g}{\lambda}$$

is $$\frac{1}{\sqrt{1 - fc/2f}},$$

b is the height of the guide (or the length of the short wall), a is the width of the guide (or the length of the long wall), $\mu_r$ is the relative permeability of the magnetic loading material, $\varepsilon_r$ is the relative permittivity of the dielectric loading material, $f_c$ is the cut off frequency of the guide, and f is the frequency of operation.

In FIG. 6, an additional material 360 added at the distal end of the waveguide. The additional material 360 may be a quartz tube used to increase the electric field at the distal end of the antenna structure.

Figure 7:
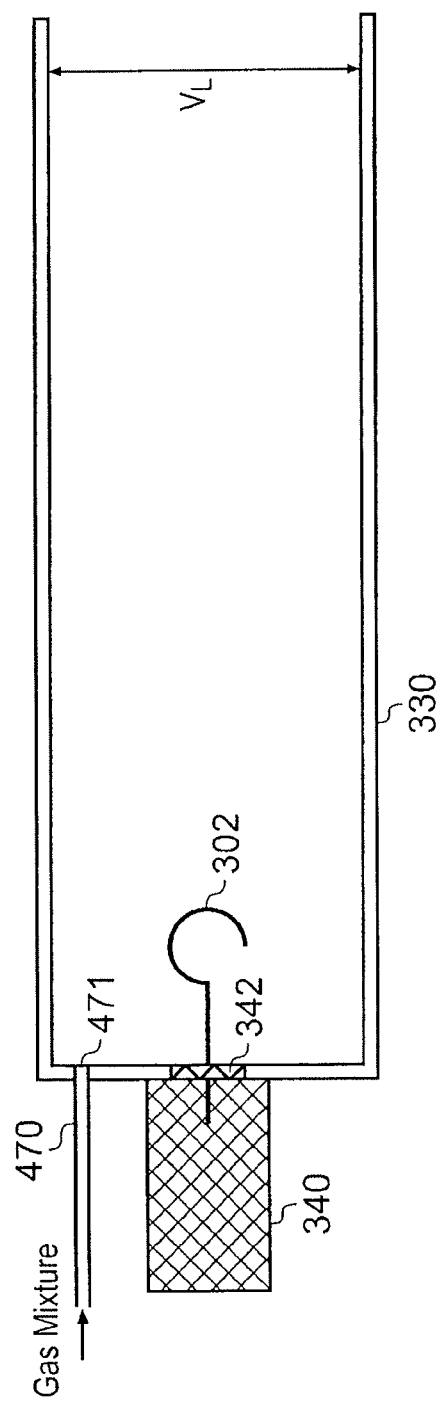
FIG. 7 is a schematic cross-sectional view of a waveguide plasma applicator suitable for use in the invention in which microwave energy and gas are input at a common end.

FIG. 7 shows a similar arrangement, but with the inlet 471 being in the same surface of the waveguide as the microwave connection. This arrangement is advantageous when the device is used to deliver plasma directly into a natural orifice within the body or through an endoscope or another tube that is inserted into to body to perform key-hole surgery or the like.

Figure 8:
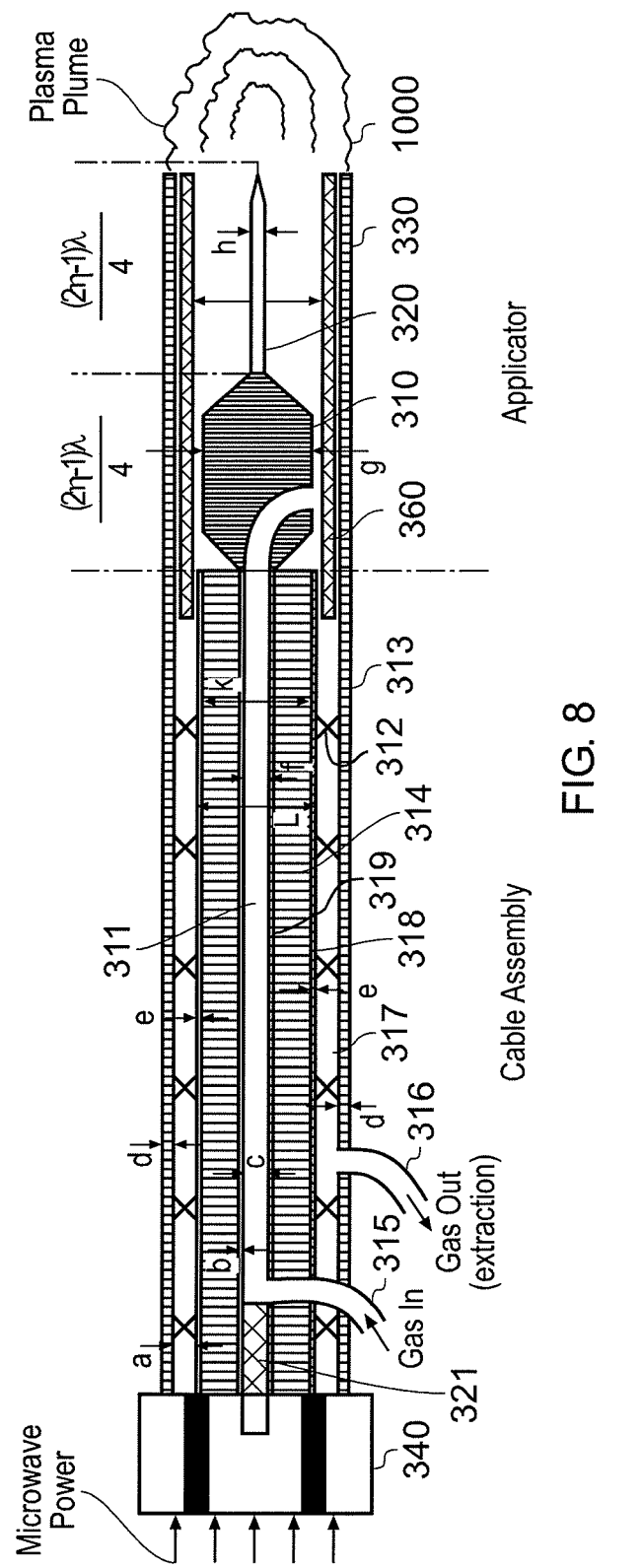
FIG. 8 is a schematic cross-sectional view of a coaxial plasma applicator having integrated gas flow channels that is suitable for use in the invention.

FIG. 8 provides a detailed diagram of an integrated microwave cable assembly and plasma applicator. In this arrangement, the integrated gas and microwave cable assembly comprises a coaxial waveguide arrangement formed using two tubes. The first tube 314 is a relatively thick walled tube made from a flexible dielectric material and is coated with a layer of metal (e.g. a metallization layer of high conductivity, e.g. made from silver, copper or gold) on both the inner wall 319 and outer wall 318,thereof. The second tube 313 is a protective jacket formed from a relatively thin walled tube made from a flexible material. The first tube 314 is suspended inside the second tube 313 using spacers 312 that may be made from a metallic or dielectric material and must allow gas to flow within and along the channel formed between the outer wall 318 of first tube and the inner wall of second tube 313. The plasma applicator comprises two impedance transformers 310, 320, a gas feed passage 315 from centre channel of first tube 314 into applicator, and a gas extraction passage 316 from the applicator along a channel formed between the outer wall of first tube and the inner wall of second tube.

A first section 321 of the inner channel used to feed gas into the applicator is solid to enable the centre pin within microwave connector 340 to be electrically connected to the new microwave cable assembly. The input microwave connector may be any connector suitable for carrying microwave power up to 600 W CW at the frequency of interest, e.g. SMA or N-type connectors may be used.

The centre 311 of the inner conductor 319 used to form the coaxial microwave cable assembly is hollow due to the fact that the microwave field produced at the frequency of interest only requires a small amount of wall thickness to enable the field to efficiently propagate along the cable or waveguide, thus the centre portion 311 of inner conductor 319 may be transparent to the microwave field. Similar criteria apply to the thickness of the outer conductor 318, i.e. it is only a thin layer 318 on the outer surface of the first tube 314 that plays an important part in the microwave field or wave propagation along the waveguiding channel.

The first tube 314 should preferably be made from a low loss dielectric material, e.g. low density PTFE, in order to ensure that the power loss along the structure (the insertion loss) is minimised. The integrated applicator or antenna is formed inside second tube 313 and forms an integral part of the cable assembly. This feature is particularly useful when the applicator is to be inserted inside a natural orifice of small diameter, i.e. less than 6 mm, or where the device is to be inserted down an endoscope.

The plasma applicator shown in FIG. 8 consists of two quarter wave impedance transformer sections 310, 320. The first section is a low impedance section whose impedance is determined by the ratio of the diameter of inner conductor (g) and the diameter of outer conductor (i) as described above. The outer conductor may be an extension of outer conductor 318 within the integrated microwave cable assembly used to transport the microwave energy from the generator to the applicator. The gas from within channel 311 is fed into the applicator through a hole, groove, or channel made in inner conductor 311.

The second transformer section is a high impedance section whose impedance is determined by the ratio of the diameter of inner conductor (h) and the diameter of outer conductor (i). The material used to form inner conductor may be a material that is able to withstand high temperature without change of physical form or characteristic, e.g. tungsten.

A quartz tube 360 is located at the distal end of the applicator between the inner and outer conductors. The quartz tube reduces the likelihood of arcing and promotes plasma striking in the plasma generating region. Here the plasma plume 1000 is directed out of the open end of the applicator by the flow of gas from the centre channel 311. An annular gap between the quartz tube and outer conductor leads to the outer channel 316. As explained below, this channel may be connected to a pump for extracting excess or residual gas from the treatment site.

Figure 9:
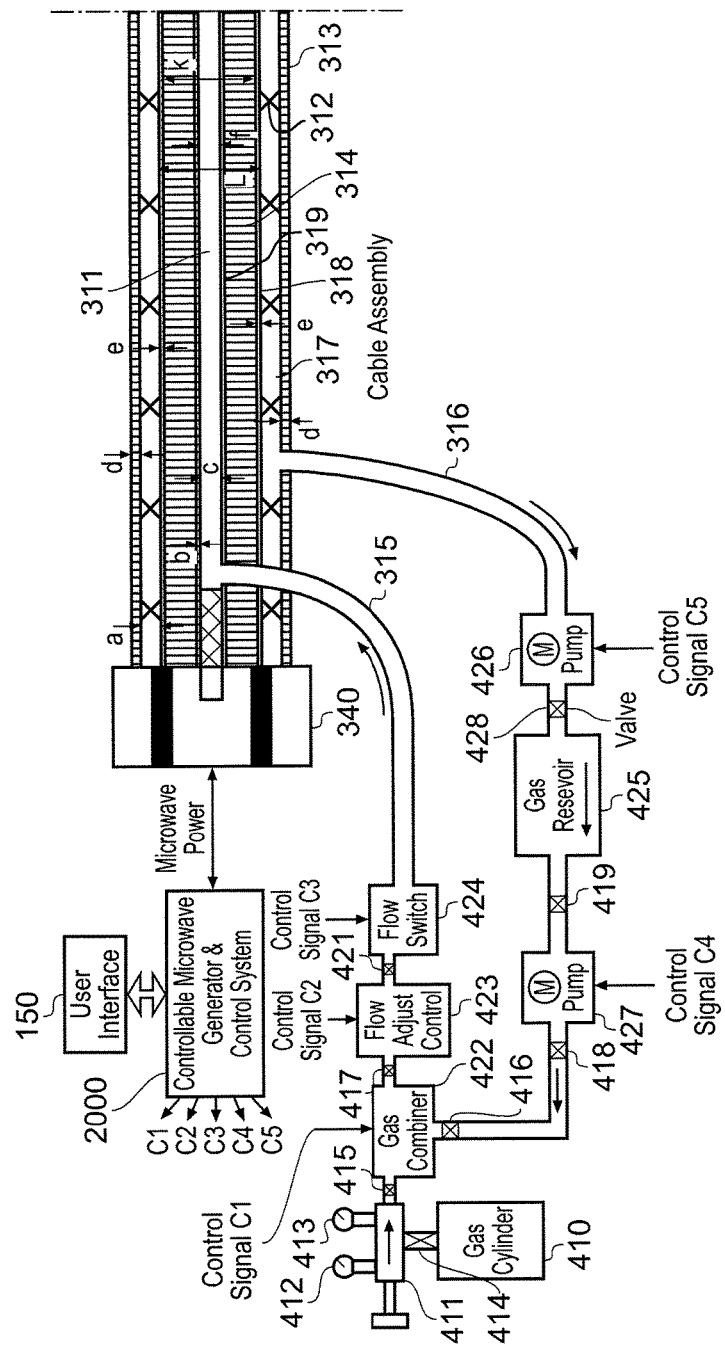
FIG. 9 is a block diagram of a residual gas return system that is suitable for use with the invention.

FIG. 9 shows an arrangement for a gas flow control system connected to the integrated cable assembly shown in FIG. 8. The integrated cable assembly shown here enables forward going microwave power to be transferred to the applicator and any reflected returned microwave power to be transferred back along same cable to the generator where measurements may be taken. The integrated cable assembly also enables the same cable to be used to enable the gas to be introduced into the applicator along a first channel and for excess gas to be returned along a second channel to prevent pressure build up when the applicator is inserted inside a closed system or a natural orifice, and also to enable the unused gas to be recycled. In the arrangement shown in FIG. 9, any excess gas is returned from applicator (not shown), along an annular channel 317 formed between the inner wall of outer jacket 313 (this may be made from an insulating or conducting material) and the outer wall of outer conductor 318. The extracted gas is fed into a transfer tube and transferred back into the gas control system. A plurality of spacers 312 (e.g. made from an insulating material, for example, nylon, PTFE or Teflon) are inserted along the length of the cable assembly between outer jacket 313 and the outer wall of outer conductor 318 to ensure that the channel is kept opened along its length in order to allow gas to flow.

This invention is not limited to using the hollow section of the inner conductor to transfer gas from the gas supply to the applicator and the channel formed between outer jacket 313 and the outer wall of outer conductor 318 to transfer gas back to the gas supply, i.e. the two feed pipes or transfer tubes may be interchanged.

The impedance of the microwave cable assembly formed by this structure is described formally below, where an analysis of the dimensions associated with the overall integrated assembly is also given.

The gas control system consists of gas extraction pipe 316, which is used to transport the excess gas back into the system. The distal end of pipe 316 is connected to an inlet to pump 426, whose purpose is to enable the excess gas to be sucked back from applicator along channel 317 and pipe 316 into reservoir 425. The flow or pumping rate at which pump 426 operates is determined by a control signal provided from a microprocessor or DSP unit within the controllable microwave generator and control system 2000. The control signal controls the speed of the motor within the pump, which determines amount of gas that can be sucked back into gas reservoir 425.

The outlet from pump 426 is connected to a one way valve 428, whose purpose is to ensure that the gas flows in one direction only, i.e. it flows into gas reservoir 425. The purpose of gas reservoir 425 is to store or hold the excess gas that has been collected from the applicator.

The outlet from reservoir 425 is connected to second one way valve 419, whose purpose is to ensure that gas only flows in one direction; in this case, it flows from the reservoir into the inlet port of second pump 427. The purpose of second pump 427 is to suck gas from reservoir 425 to enable it to be transported back into the applicator to enable more plasma to be produced.

The flow or pumping rate at which pump 427 operates is determined by a control signal provided from a microprocessor or DSP unit within the controllable microwave generator and control system 2000. The control signal controls the speed of the motor within the pump, which determines amount of gas that can be sucked out of gas reservoir 425 back into the plasma producing applicator.

The outlet from pump 427 is connected to third and fourth one way valves 418, 416 whose purpose is to ensure that gas only flows in one direction; in this case, to ensure that it flows from the outlet port of pump 427 to the inlet port of gas combiner 422. The purpose of gas combiner 422 is to combine the recycled gas with the gas provided from gas cylinder 410. The gas flow from cylinder 410 is controlled using an adjustable valve 411, which may be controlled either by mechanical or electrical means; in this arrangement, a mechanical means is chosen. Gauges 412 and 413 are shown connected to valve 411. The purpose of these gauges is to provide a means of indicating the gas pressure. One way valve 414 is connected between the output of gas cylinder 410 and the input of adjustable valve 411 to ensure that the gas flow is in one direction. A further one way valve 415 is inserted between the output of one way valve 411 and one of the inlet ports of gas combiner 422 for the purpose of ensuring that gas is not directed back into the gas cylinder 410 via adjustable valve 411.

The outlet port from gas combiner 422 is connected to a further one way valve 417, whose purpose is to ensure that the gas flows in one direction, i.e. towards the applicator. The operation of gas combiner 422 may be controlled by a control signal provided from a microprocessor or DSP unit within the controllable microwave generator and control system 2000.

The outlet from one way valve 417 is connected to the inlet port of flow adjust controller 423, whose purpose is to enable the rate of flow of the gas into the applicator to be controlled by electronic means. The operation of the flow adjust controller 423 is determined by a control signal provided from a microprocessor or DSP unit within the controllable microwave generator and control system 2000.

The output from flow adjust controller 423 is connected to a further one way valve 421, whose purpose is to ensure that the gas flows in one direction only, i.e. towards the applicator.

The outlet from one way valve 421 is connected to the inlet port of flow switch 424, whose purpose is to control the gas flow going towards the applicator. It may be possible to use flow adjust controller 421 to perform this operation as well as to adjust the amount of gas flowing in the system. If this is the case, then flow switch 424 may be omitted from the system without loss in functionality. Some or all of the one way valves may also be omitted without loss in functionality. The operation of the flow switch 424 is determined by a control signal provided by a microprocessor or DSP unit within the controllable microwave generator and control system 2000.

The outlet port from flow switch 424 is connected to gas feed pipe 315, whose function is to transfer the gas from the gas controlling system contained within the instrumentation into the applicator or cable assembly.

There now follows an analysis of the physical considerations for forming an integrated gas flow and microwave energy transfer device.

For a solid conductor, the current concentrates on the outer surface. For this reason, when skin depth is shallow, the solid conductor can be replaced by a hollow tube with no loss in performance. Skin depth can be calculated using $$\delta s = \sqrt{\frac{2}{\omega\mu\sigma}}, \text{ or}$$

$$\delta s = \sqrt{\frac{\rho}{\pi f \mu}},$$

where $\delta s$ is skin depth (m), $\omega$ is radian frequency (Hz), $\sigma$ is conductivity (S), $\rho$ is resistivity ($\Omega$m), f is frequency (Hz), $\mu$ is permeability of free space (H/m), i.e. $4\pi \times 10^{-7}$ H/m, and $\pi$ is 3.1415927.

Table 4 provides values of skin depth at spot frequencies of 1 GHz and 10 GHz for commonly used conductive materials. This table illustrates the benefit of using high microwave frequencies when it is desirable to keep the metallization thickness to a minimum, for example, in coaxial arrangements where a hollow centre conductor and an outer conductor with minimal wall thickness are desirable to enable these regions of the assemblies to be used for purposes other than transporting microwave energy to produce the sterilisation or treatment plasma.

TABLE 4

Skin depth for a range of materials at 1 GHz and 10 GHz

| Material | Bulk Resistivity | Skin Depth at 1 GHz (μm) | Skin Depth at 10 GHz (μm) |
| --- | --- | --- | --- |
| Aluminium | 2.65 | 2.59 | 0.819 |
| Beryllium | 3.3 | 2.89 | 0.914 |
| Brass | 7 | 4.21 | 1.33 |
| Bronze | 15 | 6.16 | 1.95 |
| Copper | 1.69 | 2.07 | 0.654 |
| Gold | 2.2 | 2.36 | 0.747 |
| Graphite | 783.7 | 44.6 | 14.1 |
| Nickel | 6.9 | 4.18 | 1.32 |
| Silver | 1.63 | 2.03 | 0.643 |

The percentage of power transferred as a function of material thickness can be expressed as $$\% P = \frac{1 - e^{-x}}{\delta s} \times 100,$$

where x is the thickness of the layer of metallization (m), and % P is the percentage of the power flowing in given thickness of metallization (W). This equation predicts that for a thickness of metallization of six skin depths, 99.75% of the power will be transported. For structures considered to be useful here, three materials that may be used are silver (Ag), copper (Cu), and aluminium (Al).

If the frequency of choice for generating microwave plasma is 2.45 GHz, the skin depth where 67% of the microwave field is concentrated, and the thickness of material required for 99.75% of the microwave field to be transported for three materials that have been considered for this work is given if Table 5.

TABLE 5

Depths of Penetration at 2.45 GHz for three considered materials

| Material | Depth for 67% of Field to Propagate (μm) | Depth for 99.75% of Field to Propagate (μm) |
| --- | --- | --- |
| Silver (Ag) | 1.30 | 7.80 |
| Copper (Cu) | 1.32 | 7.92 |
| Aluminium (Al) | 1.66 | 9.96 |

It can be seen from Table 5 that the required thickness for the walls of the centre and outer conductors is less than 10 μm for the three materials of choice, therefore, taking into account the need to provide a level of rigidity for the conductors, it is feasible to use a thickness of around ten times this value, i.e. 0.1 mm.

The characteristic impedance ($Z_0$) of the microwave cable assembly can be expressed as (see FIG. 9)

$$Z_0 = \frac{138}{\varepsilon_{r1}} \log_{10} \frac{k}{f},$$

where $\varepsilon_{r1}$ is the relative permittivity of the dielectric material 314, k is the inner diameter of the outer conductor 318 and f is the outer diameter of the inner conductor 319.

If one assumes that the characteristic impedance of the microwave cable assembly of interest is 50Ω, and the maximum outside diameter of the integrated cable assemble that can be tolerated to enable the assembly to be inserted inside a natural orifice is 10 mm, then a practical cable assembly design may take the following steps:

assume that the coaxial transmission line is formed by coating a first tube of low loss dielectric material with a first layer of metallization on the inside wall, and a second layer of metallization on the outer wall;

also assume that a second tube is used to provide the second channel for the gas to flow along and that the first tube is suspended inside said second tube using a plurality of thin disks containing holes or perforations placed at regular intervals along the length of the transmission line structure;

also assume that the metallization thickness on the inner surface and the outer surface of the tube is 0.1 mm (dimensions b and e in FIG. 9);

also assume that the diameter of the hole inside the first tube is 2 mm (dimension f in FIG. 9);

it then follow that the channel available for gas to flow along has a diameter of 1.8 mm (dimension c in FIG. 9);

assuming that the outer diameter of the first tube is 6 mm, the dielectric constant of the material used to form the 50Ω transmission line using the tube may then be calculated as follows:

$$\varepsilon_r = \left( \frac{138}{50} \log_{10} \frac{6}{2} \right)^2 = 1.317.$$

The material of choice for the dielectric material may be a low loss PTFE or Nylon.

Since the layer of metallization attached to the outside of the tube is 0.1 mm, the overall diameter of the coaxial structure is 6.2 mm (dimension L in FIG. 9). If the wall thickness of the second tube is 0.3 mm and the outside diameter of the second tube is 10 mm (overall outside diameter), then the channel available for the gas to be returned along is 1.6 mm (dimension a in FIG. 9).

FIGS. 10a to 10e illustrate axial cross-sectional views through a number of possible arrangements that make use of the hollow centre conductor and/or the passageway outside outer conductor for feeding the gas into the applicator and returning the gas from the applicator.

Figure 10B:
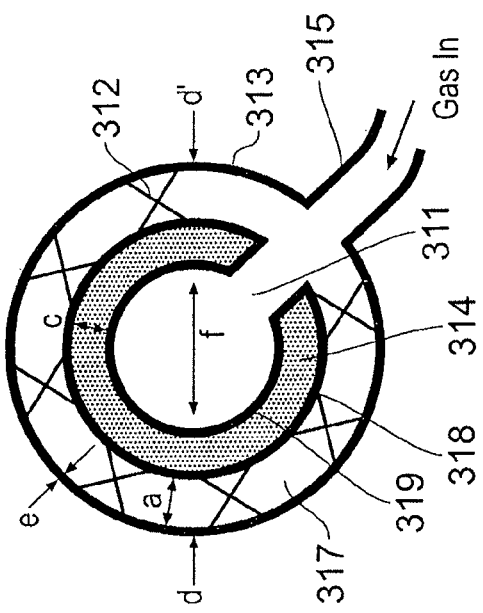
FIGS. 10a, 10b, 10c, 10d and 10e are schematic axial cross-sectional views of coaxial plasma applicators having integrated gas flow channels that are suitable for use in the invention.
Figure 10A:
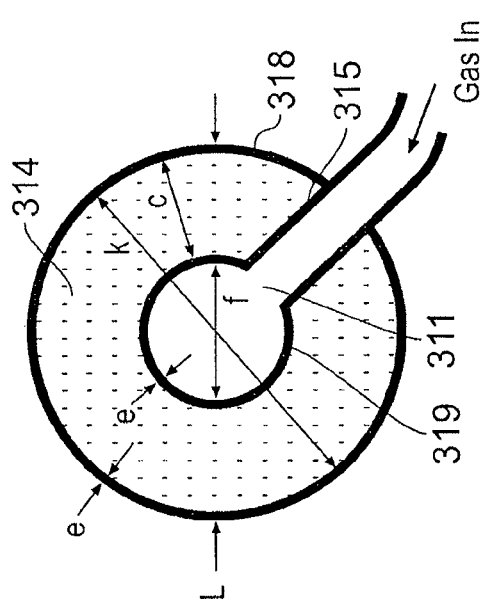
Figure 10D:
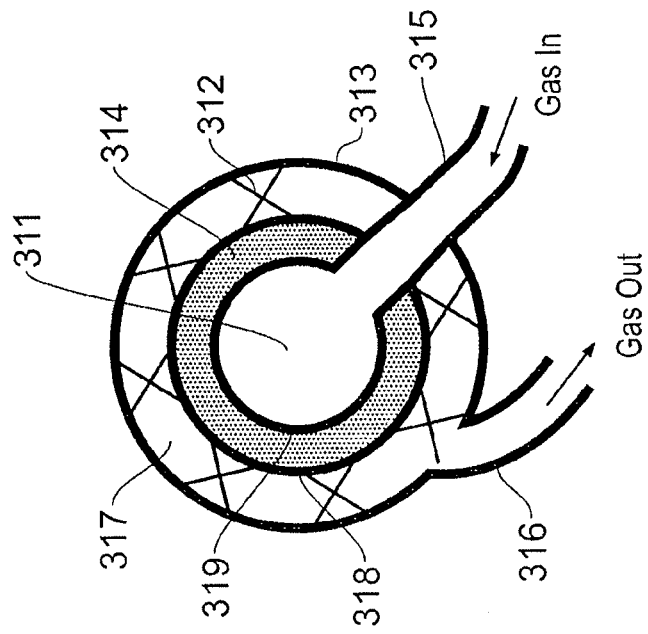
Figure 10C:
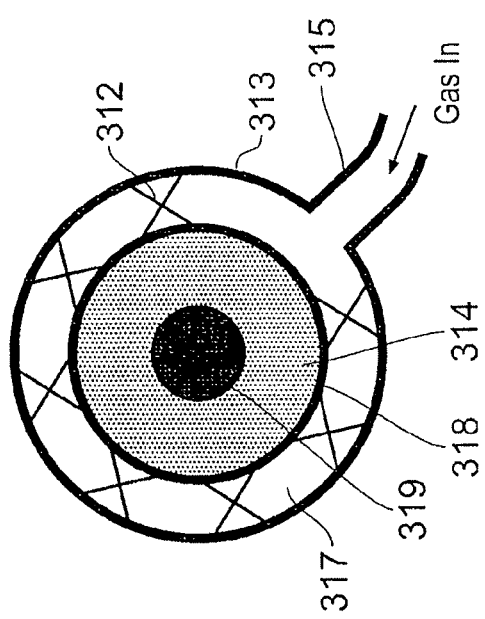
Figure 10E:
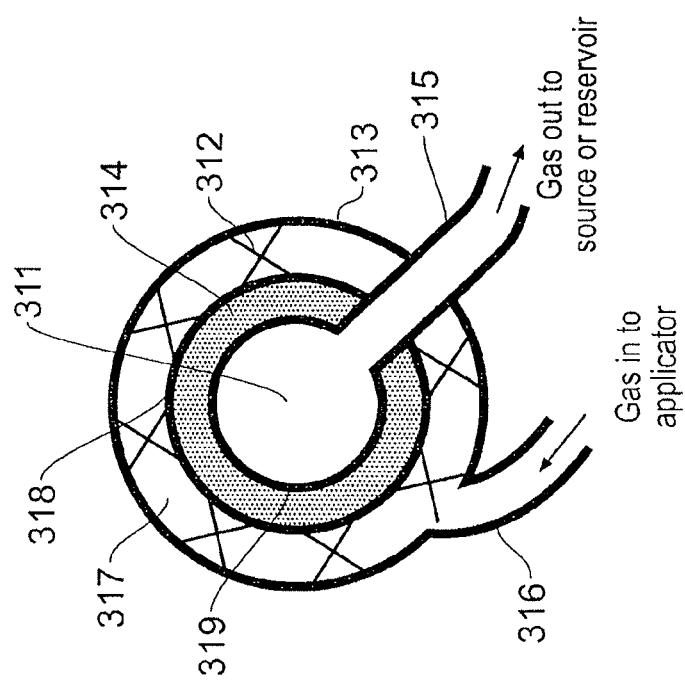

FIG. 10a shows gas fed through a hollow section 311 of centre conductor 319 only, FIG. 10b shows gas fed through a hollow section 311 of the centre conductor 319 and a passageway 317 outside outer conductor 318, FIG. 10c shows gas fed through a passageway 317 outside outer conductor 318 only, FIG. 10d shows gas fed through a hollow section 311 of centre conductor 319 and returned through a passageway 317 outside outer conductor 318, and FIG. 10e shows gas fed through a passageway 317 outside outer conductor 318 and returned through a hollow section 311 of centre conductor 319.

In FIGS. 10a to 10e, feed pipes 315, 316 are preferably made from the same or a similar dielectric material as that used to separate inner conductor 319 from outer conductor 318 in order to minimise discontinuities or reflections caused by use of a dissimilar material. The dielectric material 314 should be a low loss material at the frequency of operation and should provide a level of flexibility for the cable assembly, e.g. low density PTFE or polyurethane. The passage or channel 317 formed between outer wall of the outer conductor 318 and the inner wall of sheath 313 is supported using a plurality of spacers 312, which are preferably made from a material that will support the channel without it collapsing or closing to prevent gas flow when bent or twisted. Spacers 312 must enable gas to flow along channel 317, thus said spacers should contain a plurality of suitable holes or perforations. The material used to form outer sheath 313 may be a metallic or non-metallic material. It is preferable for said material to be a plastic or rubber material in order to help ensure the overall flexibility of the assembly to enable it to be manipulated by clinicians or other users.

Figure 11:
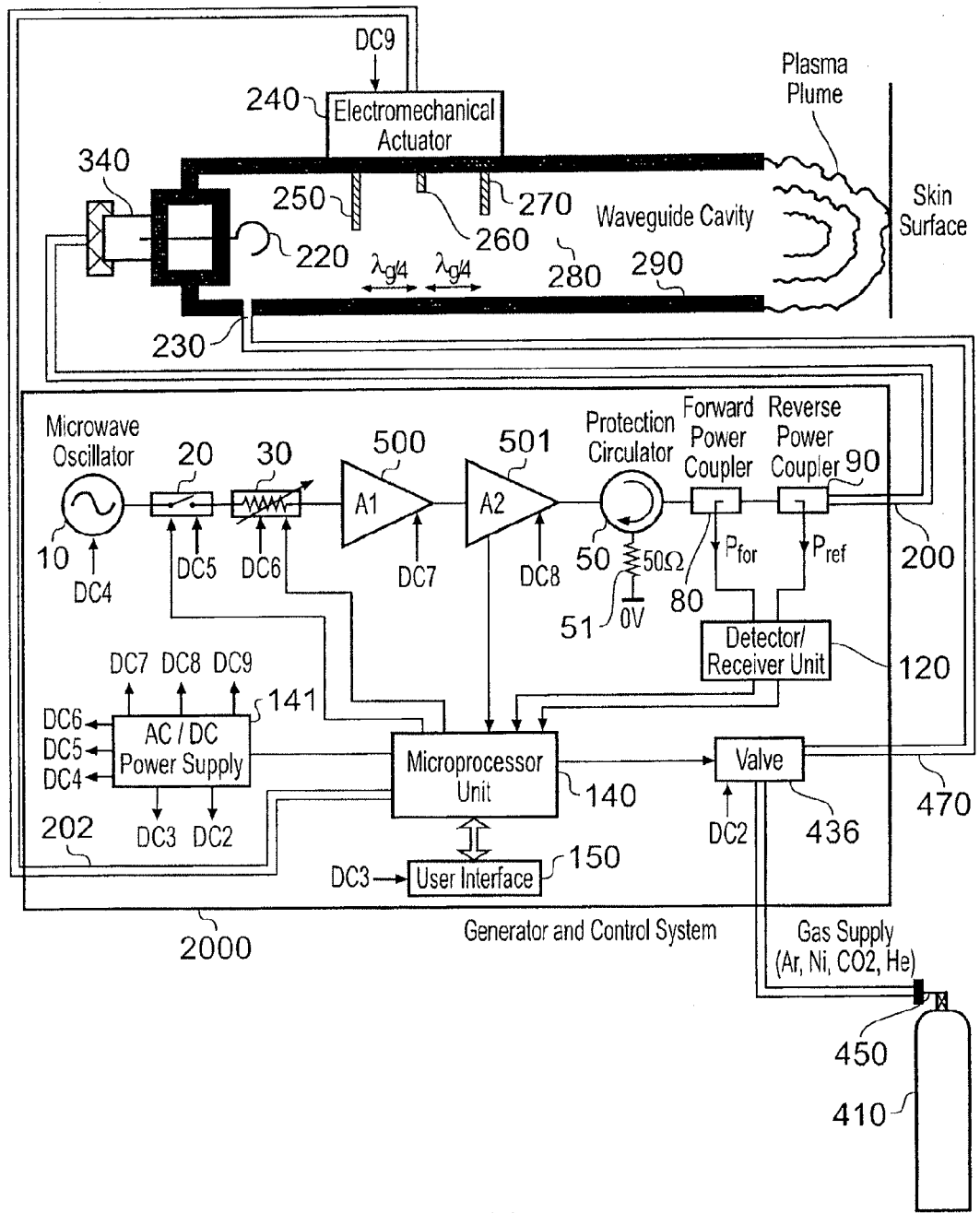
FIG. 11 is a block diagram showing a plasma sterilisation system that is an embodiment of the invention with an three stub impedance adjustor integrated with the plasma applicator.

FIG. 11 is a block diagram of a plasma sterilisation system in which automatic tuning to strike, maintain and match the plasma occurs in the plasma applicator. In the illustrated embodiment three tuning stubs and a means of adjusting the tuning stubs are contained within the plasma applicator (which is a hand-held unit).

In the embodiment, an electromechanical actuator 240 is used to move the position of three tuning stubs 250, 260, 270 within a waveguide cavity 280 in the plasma applicator. The length of the three stubs is determined by control signals produced by controller 140 contained within the microwave generator 2000. The control signal sent to electromechanical actuator 240 is based on the manipulation of signals measured at the coupled ports of forward and reflected powers couplers 80 and 90 respectively. In practice, only the reflected power need be measured in order to establish the condition required to produce the high electric field within the cavity that is necessary to strike the plasma, to determine the condition to sustain the plasma, and to match it to the varying state of the surface or tissue of which the plasma is coupled. The signals from reflected power coupler 90 and forward power coupler 80 are fed into a detector (or receiver) 120 whose function is to convert the microwave signal into a format that is acceptable for the controller 140 to use. This signal may be a DC voltage, or a lower frequency signal that contains phase and magnitude information. The DC voltage or the phase and magnitude signals are processed using the controller 140 to determine the signals that need to be sent to the electromechanical actuator 240 to move the three tuning stubs 250, 260, 270 to the position necessary to strike or maintain the plasma. The detector 120 may take the form of a diode detector with a low pass filter (for example, a tunnel diode, or a Schottky diode and a simple single pole C-R filter), or a heterodyne detector (or a homodyne detector) using a microwave frequency mixer and local oscillator signal. It may be preferable to implement the heterodyne detector (or a homodyne detector) using more than one frequency mixing down stage, i.e. a double IF heterodyne receiver may be employed that uses two microwave frequency mixers and two local oscillators.

The microwave components in the generator 2000 that are arranged to deliver microwave energy to the plasma applicator are similar to the arrangements discussed above. The same reference numbers are used to describe like components. In this arrangements there are two amplifiers 500, 501. In this embodiment, the plasma may be delivered under footswitch control, whereby a jet of plasma is produced when a user depresses a footswitch pedal connected to the instrument. The footswitch may form part of user interface 150.

The sampled signals produced by forward and reflected power couplers 80, 90 may also be used to ensure that potentially high levels of microwave power are not radiated from the distal end of the waveguide applicator in the instance where a plume or jet of plasma has not been struck due to the gas supply having run out or it has been turned off. A safety sequence may involve shutting off the microwave generator if the impedance of the waveguide cavity has not reduced from the high impedance strike state to a lower impedance conducting gas state within 10 milliseconds or 100 milliseconds after the microwave energy has been applied. The capability of being able to continuously measure the impedance of the waveguide cavity may also be used to shut-off the microwave source in a timely manner when the gas cylinder becomes empty.

It is desirable for the three tuning stubs 250, 260, 270 to be set to an initial state where it is guaranteed that a resonant cavity will be set-up in order to produce a high enough electric field to strike the plasma as soon as the microwave energy is delivered. Once the plasma has been initiated, the three tuning stubs 250, 260, 270 will be moved to a position to enable the microwave energy to be matched to the impedance of the waveguide cavity 280 containing plasma 300, hence a null or a minima should be detected at the coupled port of the reflected power coupler 90.

A PID controller could be used between controller 140 and electromechanical actuator 240 to control the adjustment of stubs 250, 260, 270. Alternatively, the PID control functions may be handled by controller 140. A further alternative is to replace the mechanical tuning system with a power PIN or varactor diode arrangement, whereby the bias voltage applied to the diodes is used to adjust the depletion layer within the diodes to produce a capacitance variation.

The power transistors used in the output stage of microwave power amplifier 501 are protected from damage caused by excessive levels of reflected power going back into the amplifier, caused by either an impedance mismatch at the applicator where the plasma is generated, damage to microwave cable assembly 200, or the applicator or cable assembly becoming disconnected, using microwave circulator 50 and power dump load 51 as discussed above.

The controller 140 also controls an electrically controlled valve 436, which is opened to allow gas to enter the waveguide cavity 280. It is preferable to ensure that the gas enters the cavity before the microwave energy is applied or input into the cavity in order to ensure that non-ionised microwave radiation is not emitted from the distal end of the waveguide into the skin or other biological tissue.

It may also be desirable to control the rate of gas flow using an electrically controlled flow meter (not shown here). By knowing the initial volume of gas contained within gas cylinder 410 and the flow rate and time, it is possible to determine the volume of gas left in the cylinder at any one time. This information may be used to ensure that the microwave energy source is turned off before the gas cylinder becomes empty.

The system shown in FIG. 11 shows three inputs entering the plasma applicator: the control signal line 202 to the electromechanical actuator, the microwave cable assembly 200 that connects the microwave energy generator to the applicator, and the gas feed tube 470 to carry the gas supply from gas cylinder into the waveguide cavity. It may be desirable to house the three inputs inside a single jacket in order to facilitate ease of use or manipulation of the applicator. The gas enters the plasma applicator through a opening in the wall 230 of waveguide 290.

The input microwave connector 340 shown here uses an H-field probe 220 to couple the microwave power into waveguide 290. This invention is not limited to this arrangement, i.e. an E-field probe may be used to couple the microwave energy into the structure.

The user interface 150 provides an interface between the user (clinician or surgeon) and the treatment system (manmachine-interface). For example, it may be required to enter the type of gas (or types of gases) used (He, $CO_2$, Ar, Ne, $O_2$ etc), the duration of the treatment and the power level, the flow rate. The dosage of plasma energy can be calculated from this information and may be displayed. User interface 150 may also indicate error or fault conditions. The user interface may take the form of a LED/LCD display and a keypad, a touch screen display, or the like.

A power mains voltage to DC voltage power supply 141 is used to provide the voltage/current required by the electrical components within the system. It is preferable for power supply 141 to be a switched mode power supply in order to obtain optimal AC mains to DC voltage efficiency. Power factor correction may be included within the unit to optimise this efficiency.

Figure 12:
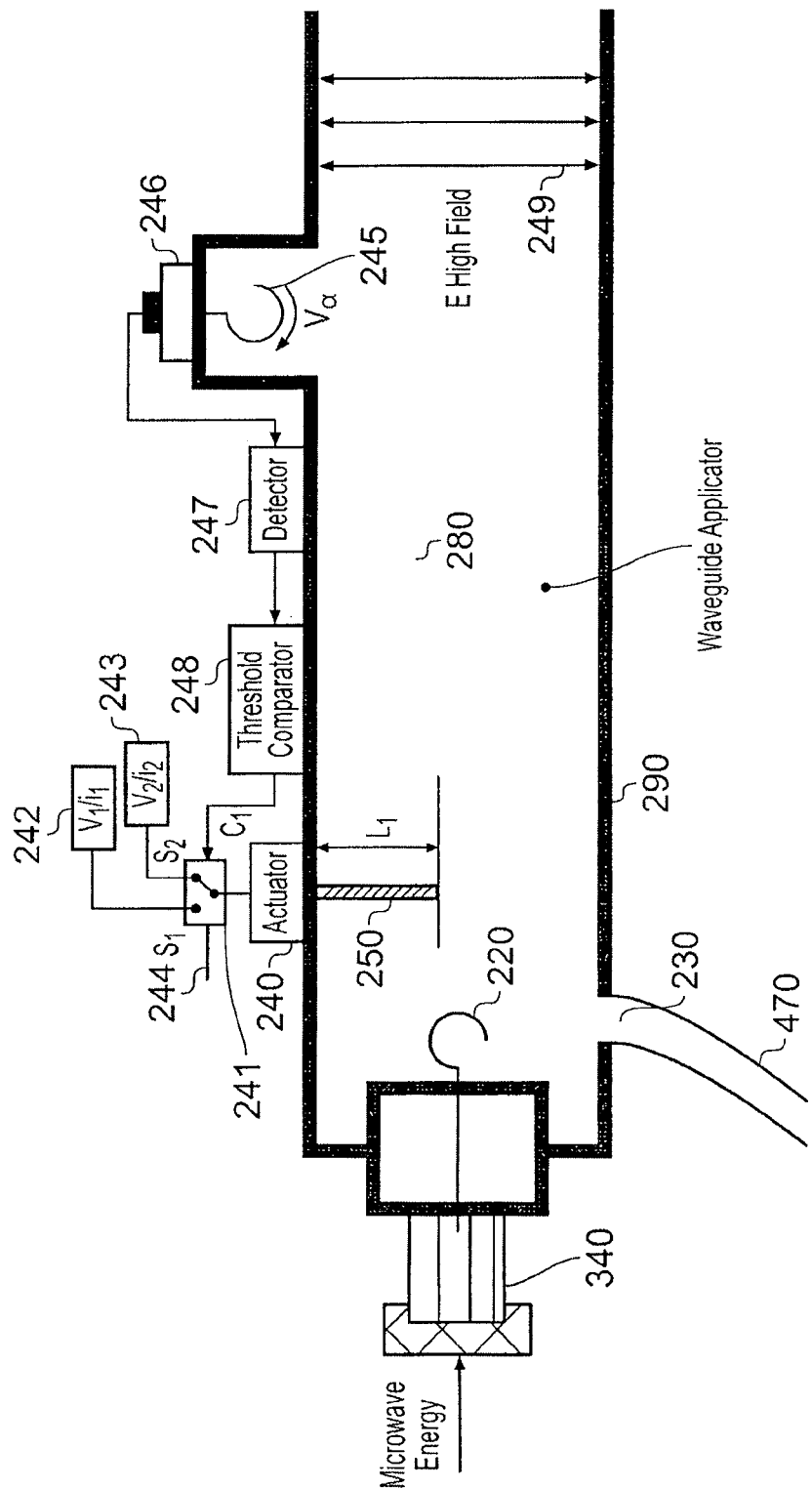
FIG. 12 is a block diagram showing a plasma sterilisation system that is an embodiment of the invention with a one stub impedance adjustor integrated with the plasma applicator.

FIG. 12 shows another plasma applicator where the automatic tuning system is contained therein. The arrangement shown uses only one tuning stub 250 for convenience, but it may be preferable to use two, three, or more stubs in practice.

The automatic tuning mechanism works by setting the distance stub 250 protrudes inside the cavity 290 to a length $L_1$ determined by drive signals 242, 243 (represented as $V_1/i_1$ and $V_2/i_2$ in this embodiment) at the input to the electromechanical actuator 240 used to move the tuning stub 250 inside waveguide cavity 290. A single pole two throw switch 241 is used to select one of the drive signals 242, 243 for transferring to the actuator 240. The switch position $S_1$ or $S_2$ is determined by control line signal $C_1$ and reset signal 244. A MOSFET device or a relay may be used to implement the switch 241. In the instance where switch 241 has only one control signal input, the reset and control functions may be supplied using a logic gate arrangement, for example, a D-type flip flop or an arrangement of logic gates. FIG. 12 shows the switch as a block with two inputs and does not show the additional glue logic that may be required.

In order to sense the magnitude of the electric field set-up inside the waveguide cavity, an H-field loop coupler 245 is located near the distal end (i.e. the outlet) of the applicator. A connector 246 (e.g. an SMA or N-type connector) is used to connect the output signal from the H-loop coupler 245 to the rest of the circuit. In order to be able to successfully detect a portion of either the forward going or reflected signal, a non-coupled port (not shown) may also be provided. An E-field probe may be used to sense the magnitude of the electric field. The coupler 245 senses a portion of the field set-up inside the waveguide cavity 280. The coupled signal is fed into detector 247, which may be a magnitude detector, a phase and magnitude detector, or a phase detector. The detector 247 produces a DC or low frequency AC voltage signal which is fed into the input of threshold comparator 248, whose function is to provide a control signal to switch 241 to change the pole position in accordance with the value of the electric field set-up inside the waveguide cavity 280 and determine whether or not the microwave source is switched on (this can be also be determined by the status of the reset signal).

FIG. 12 shows an arrangement where stub 250 is set to a position to produce a maximum electric field inside the waveguide cavity 280 in order to enable the plasma to be struck when a suitable gas is supplied to the waveguide cavity and the microwave source is switched on. Once the plasma has been struck, the electric field 249 will be reduced and this will be detected by a change in the voltage $V_\alpha$ picked up using H-field sensing coupler 245. The change in the magnitude of the electric field 249 may be used to change the state of the output of the threshold comparator 248 to cause the switch position to change to S1 to enable the drive signal 242 ($V_1/i_1$) to be seen at the input to the electromechanical actuator 240 to cause the length L1 of stub 250 protruding inside the waveguide cavity 280 to change. The new condition will enable the microwave energy to be impedance matched into the waveguide cavity 280 to sustain the plasma and provide efficient energy delivery with a minimum level of reflected microwave energy being returned back to the microwave source.

For the practical realisation of this arrangement, it may be desirable to use the high voltage detected when the high electric field 249 is present to trigger the threshold comparator 248 to move the stub 250 to the second position necessary to sustain the plasma. If it is assumed that plasma will definitely be struck once a high enough electric field 249 has been established then the threshold comparator 248 may be triggered at a predetermined time after the high electric field 249 has been detected (or has been established) using H-field coupler 245. A time delay may be introduced into the system using a repeatably triggerable monostable circuit or a L-C, C-R delay circuit to enable this sequence of events to occur.

In a practical embodiment, it may be desirable to locate the physical position of the tuning stub 250 closer to the distal end of the plasma applicator.

Figure 13:
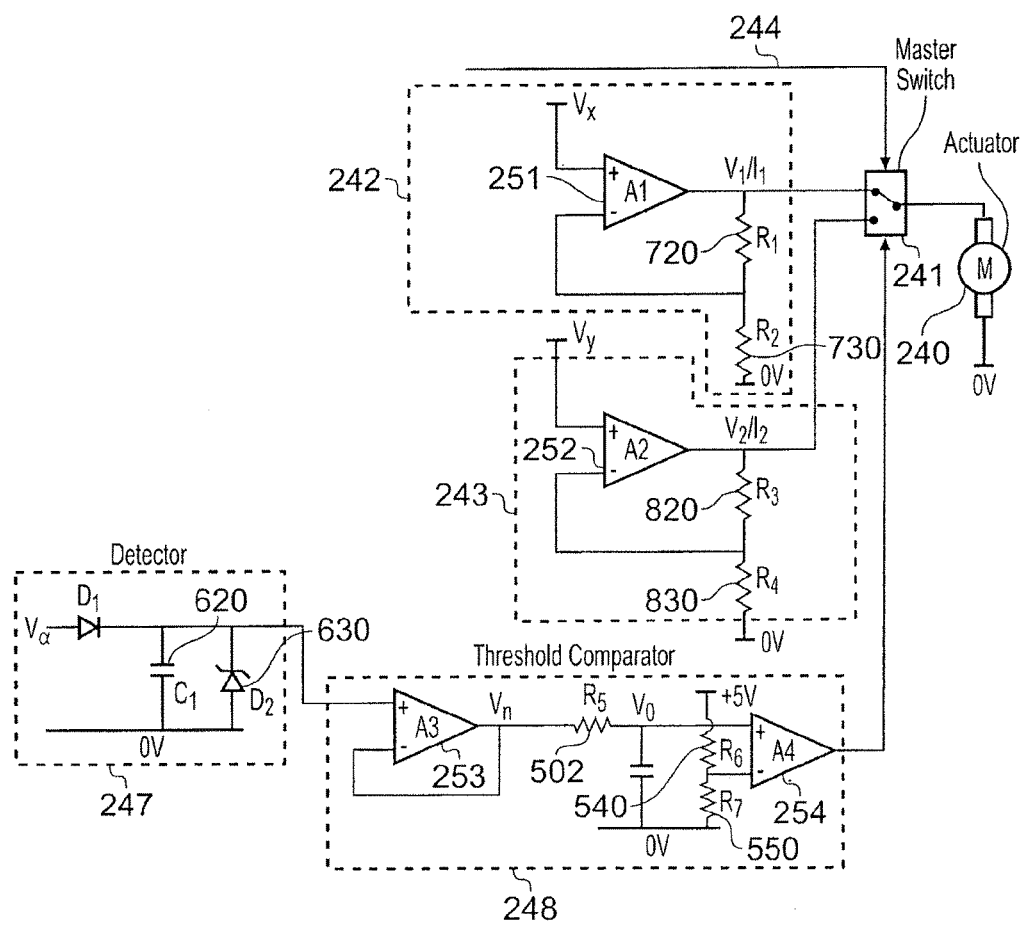
FIG. 13 is a block circuit diagram showing the stub actuator control circuitry.

FIG. 13 is a diagram showing a specific embodiment of the actuator control arrangement described above. The implementation shown here uses analogue signal processing for speed of operation, ease of implementation, and simplicity. It saves the need to implement a PIC or microprocessor and associated peripheral components. The two actuator drive signals 242, 243 are derived using respective operational amplifiers 251, 252 configured as non-inverting amplifiers. The voltage/current ($V_1$) applied to the electromechanical actuator 240 to cause the stub 250 to be moved to enable it to protrude inside the cavity 280 to a desired length L1 to enable a high electric field 249 to be set-up to initiate or strike the plasma can be expressed as $$V_1 = V_x\left(1 + \frac{R_1}{R_2}\right),$$

where $V_x$ is the voltage applied to the non-inverting input terminal of first operational amplifier 251, $R_1$ is the resistance of first feedback resistor 720 connected between the output of first operational amplifier 251 and the inverting input to first operational amplifier 251, and $R_2$ is the resistance of a resistor 730 connected between the inverting input to first operational amplifier 251 and ground.

Similarly, the voltage/current $V_2$ applied to cause the stub 250 to be moved by the electromechanical actuator 240 to enable it to protrude inside the cavity 280 to a length L2 to enable the plasma to be maintained may be expressed as $$V_2 = V_y\left(1 + \frac{R_3}{R_4}\right),$$

where $V_y$ is the voltage applied to the non-inverting input terminal of second operational amplifier 252, $R_3$ is the resistance of second feedback resistor 820 connected between the output of second operational amplifier 252 and the inverting input to second operational amplifier 252, and R₄ is the resistance of a resistor 830 connected between the inverting input to second operational amplifier 252 and ground.

The first and second operational amplifiers 251, 252 may be contained in a single packaged integrated circuit and may come in the form of a small surface mount device.

In this embodiment, the detector 247 comprises a RF or microwave diode D1 610, filter capacitor C1 620 and zener clamp diode D2 630. The input signal to detector 247 is the voltage $V_\alpha$ picked up from H-field coupler 245 contained within the waveguide cavity 280. The diode 610 may be a zero bias Schottky diode or a tunnel diode, the capacitor 620 may be a low loss capacitor, for example a 0.1 µF COG, and the diode 630 may be a 4.7 V zener diode. The zener diode 630 is used to ensure that the input voltage going into the non-inverting terminal of buffer amplifier 253) does not exceed 4.7 V, thus this component protects the rest of the circuit following detector unit 247.

In this embodiment, the threshold comparator 248 comprises a buffer amplifier 253 and an operational amplifier 254. Buffer amplifier 253 is an operational amplifier configured as a unity gain buffer. Operational amplifier 254 is configured as a voltage comparator. The buffered signal produced at the output of the buffer amplifier $V_n$ is delayed using a single pole low-pass filter arrangement comprising a series connected resistor 520 and a shunt connected capacitor 530. The voltage $V_O$ at the non-inverting input to operational amplifier 254 can be expressed as $$V_0 = V_n(1 - e^{-t/\tau}),$$

where $\tau$ is the time constant of the circuit.

The voltage applied to the inverting input of operational amplifier 254 is given by the output from the potential divider formed by the series connected resistor chain 540, 550. The reference voltage applied to the inverting input terminal can be expressed as $$+5 \text{ V}\left(\frac{R_7}{R_6 + R_7}\right).$$

where $R_6$ is the resistance of a first resistor 540 connected between a +5V supply and the inverting input terminal of operational amplifier 254, and $R_7$ is the resistance of a second resistor 550 connected between the inverting input terminal of operational amplifier 254 and ground.

Once the voltage applied to the non-inverting terminal of operational amplifier 254 reaches the threshold voltage (determined by the reference voltage discussed above), the output from operational amplifier 254 will change the pole position of MOSFET switch from S1 to S2 to enable the stub 250 to be moved into a second position to enable a low impedance condition to be set-up inside the waveguide cavity 280 to sustain the plasma. When a reset signal 244 is present, the pole position will move back to S1. The electromechanical actuator 240 is shown here as a motor. The electromechanical actuator 240 could also take the form of a linear motor, or a linear actuator, for example, a magnetostrictive material based linear actuator arrangement.

A sequence of events representing the operation of the system shown in FIGS. 11-13 may be as follows:

reset system using the reset signal 244 to ensure that the switch 241 is in position to ensure stub 250 adopts a position that will create a high electric field 249 within the waveguide cavity 280 to enable the plasma to be struck, turn on gas supply using regulator 450 and valve 436 (using controller 140) to ensure that gas has entered waveguide cavity 280, after a predetermined delay (to ensure that the cavity 280 is filled with the gas) turn on microwave energy source using control signals produced by controller 140, the high electric field 249 set-up in waveguide cavity 280 filled with appropriate gas causes a plasma to be initiated or struck, after a short time delay switch pole position of switch 241 to enable the plasma to be maintained by creating a low impedance condition inside waveguide cavity 280 to enable the output power from microwave energy source to be impedance matched with the conducting gas (the plasma) to enable clinically useful plasma to be set up and maintained.

Practical implementation of the circuit given in FIG. 13 may be carried out using surface mount components, for example 0201 and 0603 devices, in order to keep the physical size of the circuits to a minimum to enable a compact hand-piece design to be manufactured. Both active and passive devices are now available in these small packages and so it is feasible to implement the circuits in this manner to enable the circuit to be contained within the hand-piece in a non-obtrusive manner.

It may be desirable to spring load the tuning stubs 250, 260, 270 and use a ratchet mechanism to enable the three stubs to be set in two positions only. The first position will enable the plasma to be struck and a second position will enable the plasma to be maintained (level of reflection is minimised) as described above. In this particular arrangement an automated tuning mechanism may not be required. The distance between the centres of the three stubs is preferably a quarter or three quarters of the guide wavelength (more details are provided on this particular aspect below), but the invention is not limited to using this spacing, i.e. one eighth or half wavelength may also be used.

In another embodiment, the condition of the plasma being struck may be detected using a suitable sensor, for example, a directional coupler 80, 90 and a detector, or a voltage measuring device. The stubs may be movable based on this measurement. Using this method of control, the lengths of the three stubs inside the cavity may also be varied in accordance with the changing impedance of the surface or tissue that the plasma is being coupled into, i.e. the magnitude and/or phase of the signal produced by reflected power coupler 90 will change in accordance with the impedance match between plasma plume and the surface, and this signal can be used to vary the position of the stubs to minimise the change or set up a conjugate match condition, e.g. by using an associated optimisation routine to ensure that the position of the tuning stubs coincide with a null or minima in the reflected signal.

A particular advantage of the embodiment discussed with respect to FIGS. 11-13 is that the resonant cavity may not suffer from the reduction in Q caused by the insertion loss of the cable assembly inserted between the generator and the applicator; this reduction in Q may cause the electric field generated inside the cavity to be reduced, which could limit the ability of the system to sustain the plasma.

Figure 14:
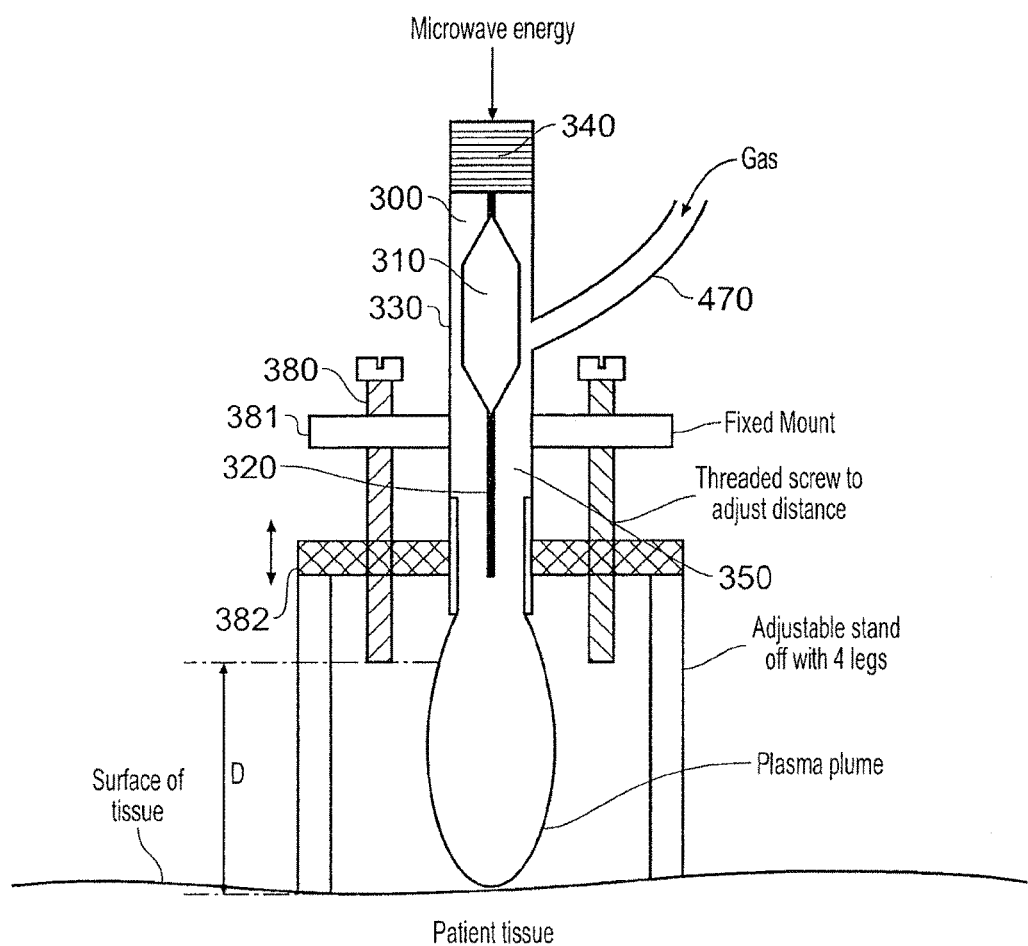
FIG. 14 is a schematic cross-section view of a plasma applicator with an adjustable stand off that is suitable for use in the invention.

FIG. 14 shows a mechanical arrangement that may be used to ensure that the plasma temperature does not exceed a safe limit when it comes into contact with patient tissue. The safe limit may be defined as being around 10° C. above room temperature or a temperature that cannot cause burning or heat damage to the patient tissue. The arrangement shown in FIG. 14 comprises of a fixed mount 381, which is permanently connected to the outer body 330 of plasma applicator 300, and a movable section 382, which can move freely along the outer body 330, and whose position is adjusted using threaded screws 380. Locking nuts may also be included to ensure that the position of the stand-off is fixed and cannot change. At least two legs are connected to movable section 382 and the distal end of these legs is in contact with the patient tissue to prevent the plasma plume to be in direct contact with patient tissue. This arrangement may be used to control the temperature of the plasma to ensure that the plume cannot cause any tissue damage. Other parameters, such as microwave power level, pulse on/off time, modulation frequencies, gas mix, and gas flow rates also determine the temperature of the plasma with respect to the surface of the patient skin, therefore, the stand-off arrangement given here may be used as a secondary measure to ensure that a safe temperature cannot ever be exceeded. Apart from temperature control, the adjustable stand-off may also be used as another means of controlling the amount of plasma energy that is delivered into patient tissue. For example, in instances where it is required not to totally destroy certain bacteria, the required plasma energy to be delivered into patient tissue may be less than that required to totally destroy the bacteria.

Figure 15:
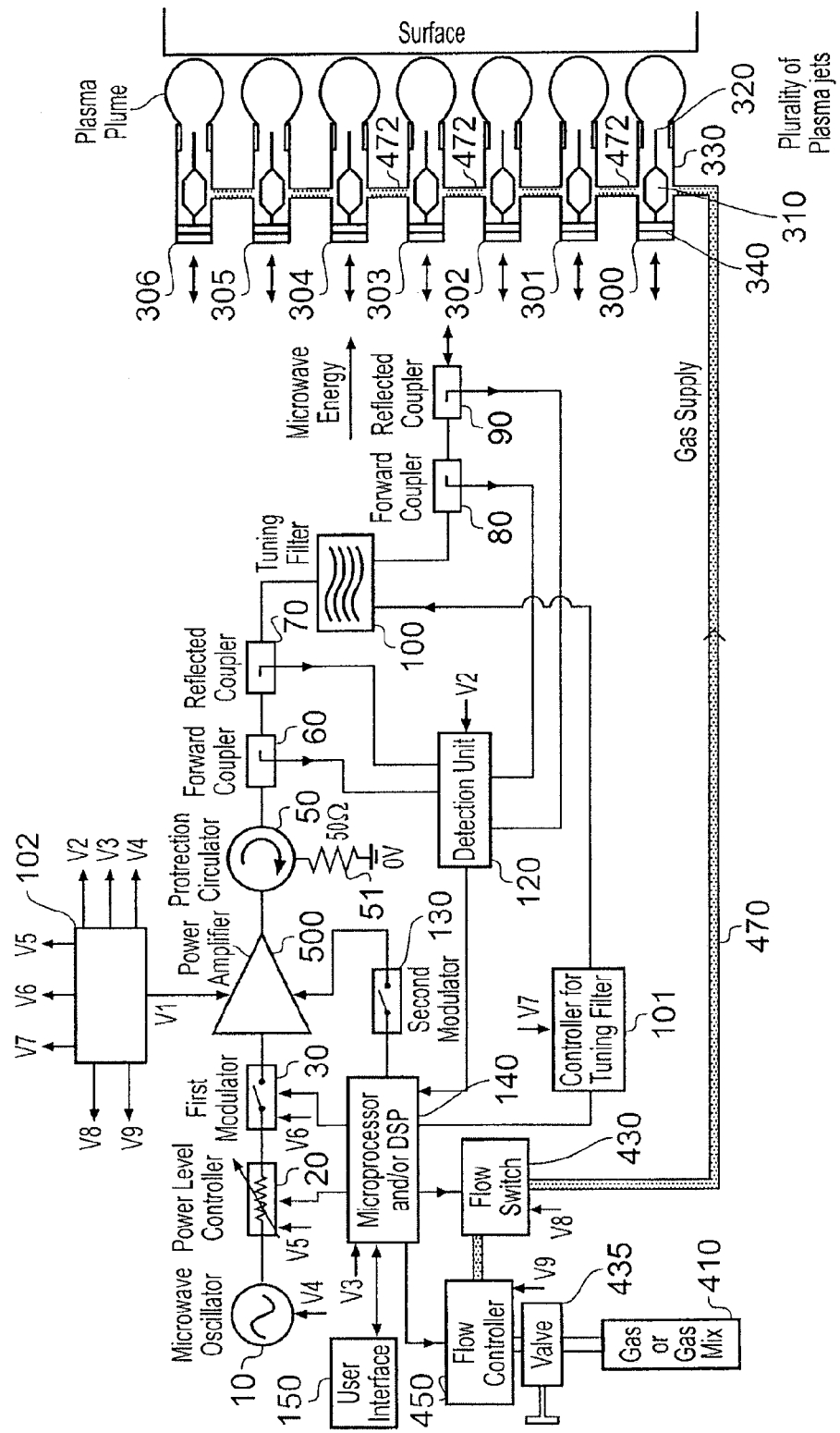
FIG. 15 is a block diagram showing a plasma sterilisation system having a power splitting arrangement and a plurality of plasma generating regions that is an embodiment of the invention.

FIG. 15 is a block diagram showing a plasma sterilisation system having a plasma applicator comprising a plurality of plasma generating regions. In FIG. 15 the plasma applicator comprises seven plasma jets 300-306, each of which have a configuration similar to the plasma applicators shown in FIG. 3. The system is arranged to produce a plurality of plasma plumes simultaneously in a controlled manner that permits a blanket of plasma to be emitted. The arrangement may be useful for treating an area (e.g. a large area) in a uniform manner. The system shown in FIG. 15 operates in a similar manner to that shown in FIG. 1. Components which perform the same or a similar function are given the same reference numbers and are not described again.

In this embodiment the impedance adjustor 100 is a tuning filter, e.g. comprising one or more variable capacitors or the like, controlled by a filter controller 101 which receives information from the controller 140. FIG. 15 also shows a power source 102 for providing power supplies $V_1$-$V_9$ to components in the generator.

The main difference between the embodiments shown in FIGS. 1 and 15 is the power splitting arrangement that enables the plurality of plasma beams to be controllably generated in a substantially simultaneously. The seven plasma jets 300-306 are connected in parallel by a power splitting unit (not shown) to the output power from the reflected coupler 90. In this embodiment the plasma jets 300-306 are connected in series to the gas feed 470, i.e. the plasma generating regions in each plasma jet are connected by gas flow pipes 472. It is also possible to connect the plasma generating regions in parallel, but the illustrated arrangement is more efficient and saves space.

Figure 16:
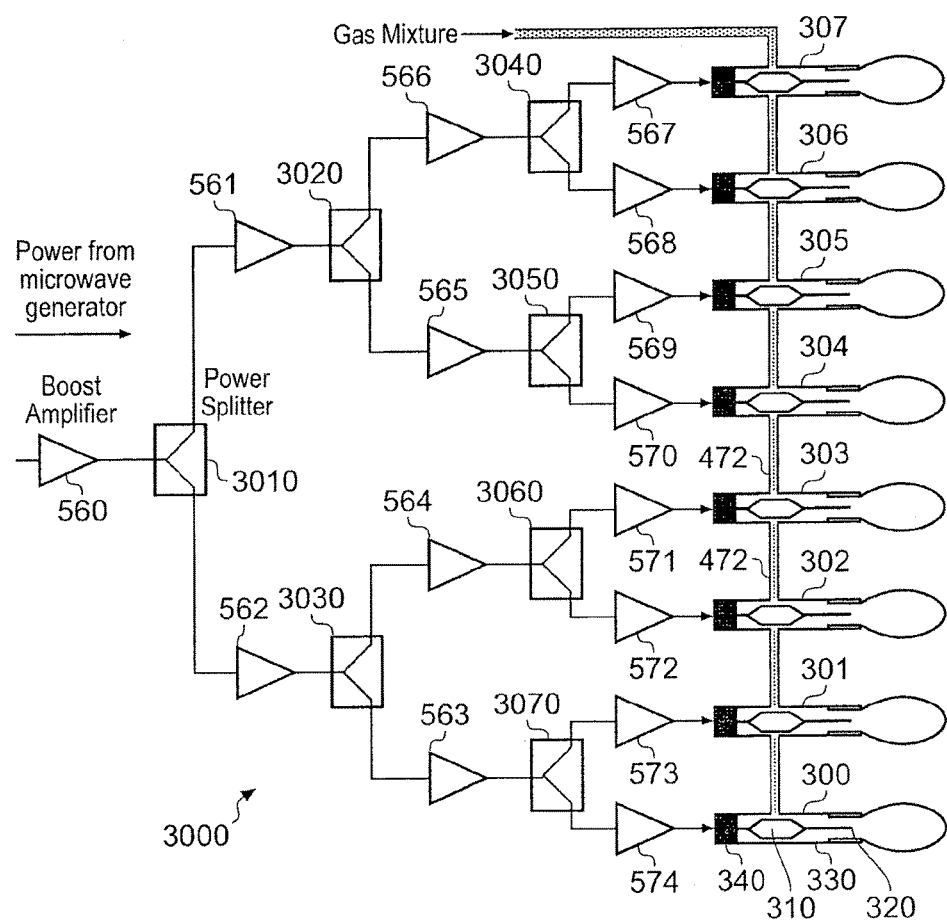
FIG. 16 is a block diagram showing a power splitting arrangement suitable for use with the system of FIG. 15.

FIG. 16 illustrates schematically a possible arrangement for the power splitting unit 3000 in an example where there are eight plasma jets 300-307 connected in series to the gas feed but in parallel to the microwave energy. The power splitting unit 3000 comprises a plurality of boost amplifiers and power splitters. The microwave power from generator (i.e. from output port of reflected coupler 90) is input to first boost amplifier 560. The purpose of the boost amplifiers is to maintain the signal at a power level whereby a high enough voltage can be created in each plasma jet to enable a plasma to be struck. FIG. 16 shows a boost amplifier located before each splitter. In practice this need not be essential.

The output of first boost amplifier 560 is input to first power splitter 3010 (e.g. a conventional 3 dB power splitter) which splits the input signal into two balanced outputs. The two outputs from the first power splitter are input to second and third boost amplifiers 561, 562 respectively. The outputs of the second and third boost amplifiers 561, 562 are input to second and third power splitters 3020, 3030 respectively. The four outputs of the second and third power splitters 3020, 3030 are input to fourth to seventh boost amplifiers 563-566, whose outputs are input to fourth to seventh power splitters 3040-3070. The fourth to seventh power splitters 3040-3070 provide eight outputs, one for each plasma jet 300-307. Before being input to the plasma jet, each output from the fourth to seventh power splitters 3040-3070 is input to a respective boost amplifier 567-574.

Figure 17:
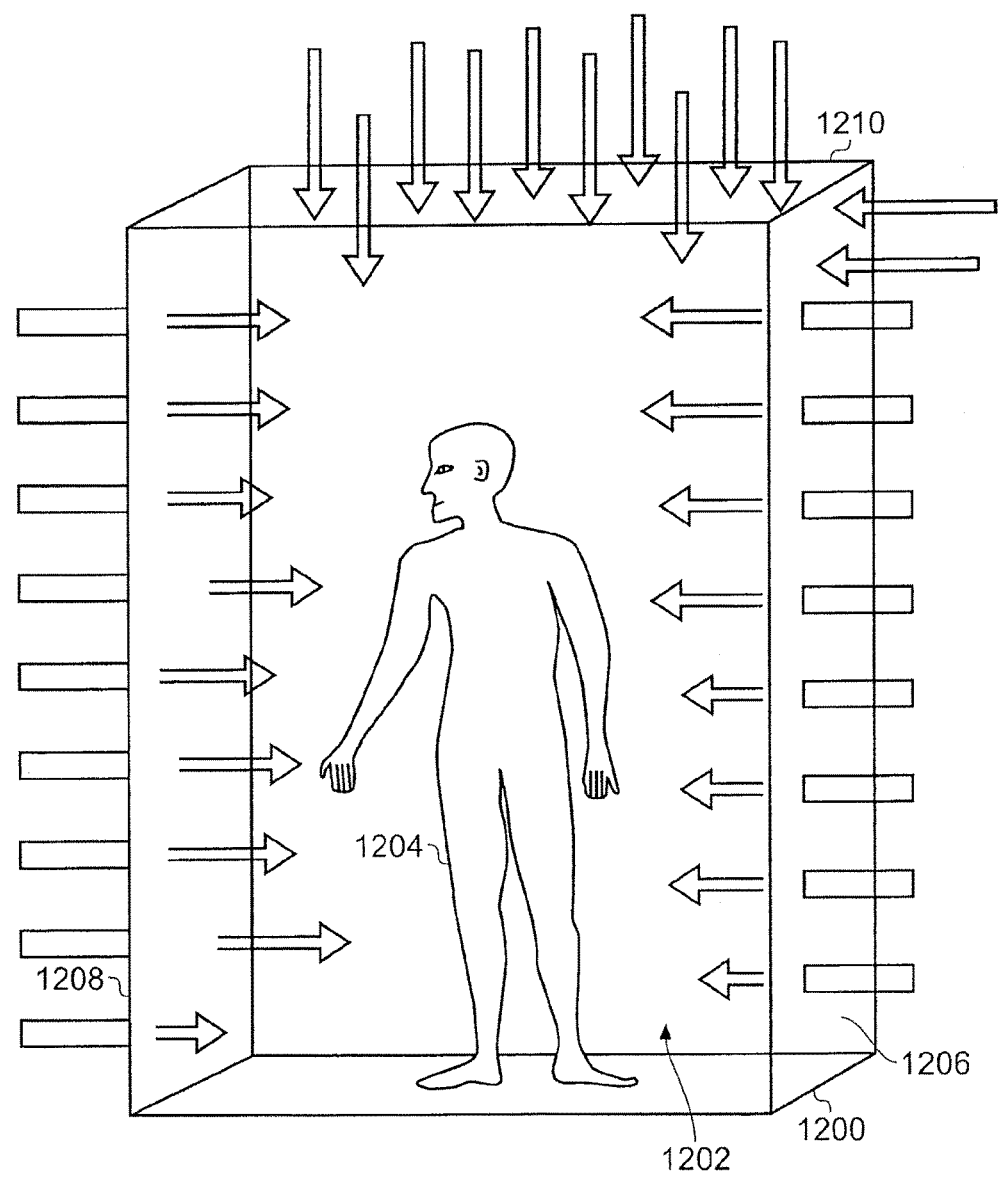
FIG. 17 is a schematic diagram illustrating a plasma applicator which defines an aperture.

FIG. 17 is a schematic diagram illustrating how a system capable of producing a plurality of plasma plumes may be used. The diagram shows a rectangular frame 1200 defining an aperture 1202 suitable for a person 1204 to pass through. The frame may be a doorframe or the like. The frame 1200 may be made from two upright panels 1206, 1208 and an cover panel 1210, each of which house a plurality of plasma jets (shown schematically as block arrows). The plasma jets may correspond to the plasma jets of plasma applicator shown in FIGS. 15 and 16. The plasma jets are arranged to direct the plasma plumes inwards, i.e. into the aperture, so that an object (e.g. person, furniture or the like) passing through the aperture is exposed to sterilising plasma. The panels may be movable e.g. to alter the size of the aperture for different sizes of object.

Figure 18:
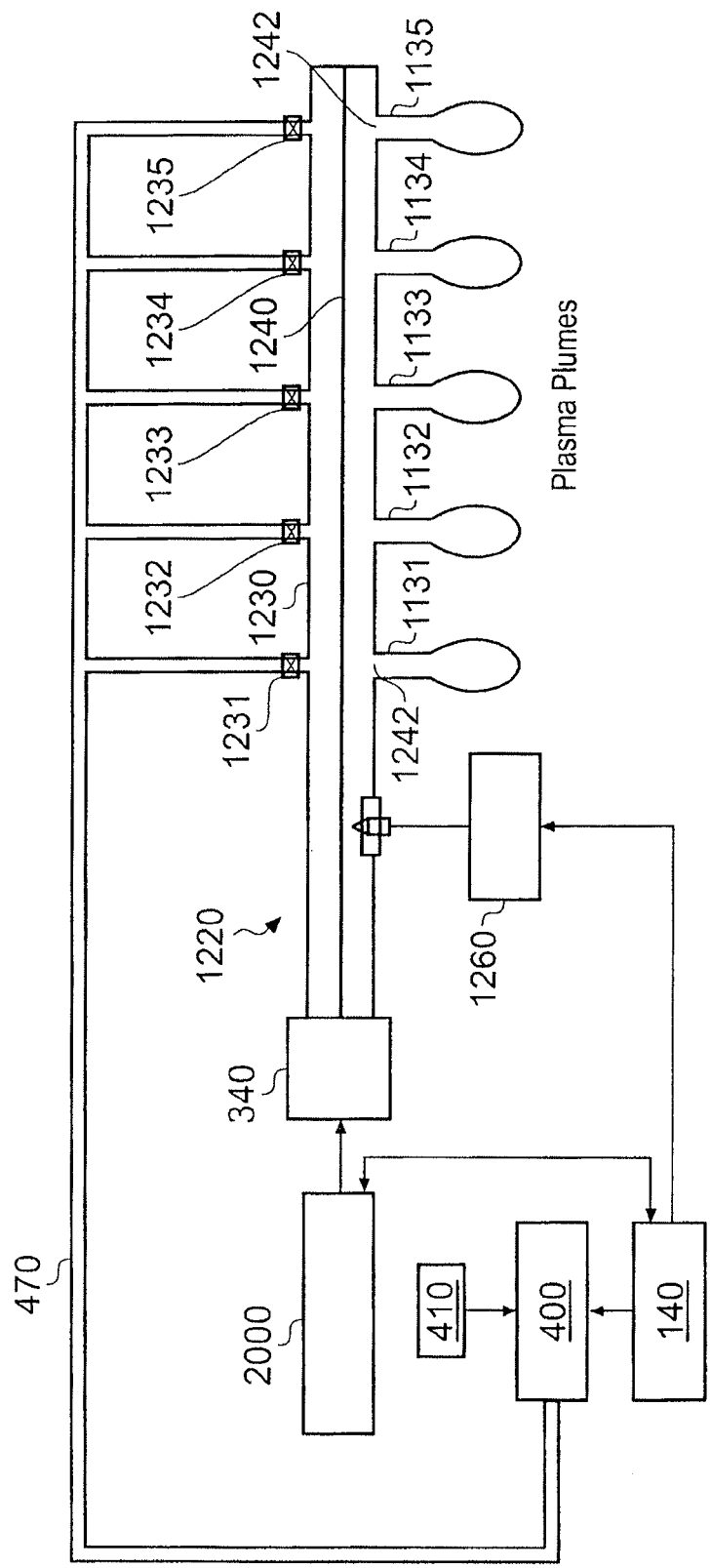
FIG. 18 is a schematic diagram of a handheld coaxial plasma applicator having a plurality of plasma generating regions.

FIG. 18 shows another example of a plasma sterilisation system having a plurality of plasma generating regions. This example is on a much smaller scale than that of FIG. 17 in that the plurality of plasma generating regions are all contained within a hand-held unit, e.g. a plasma 'brush' or 'comb' applicator. Here the plasma applicator has a plurality of nozzles arranged to emit plasma. The spacing between the nozzles is such that the plasma appears to be a continuous line of plasma.

The applicator takes the form of a coaxial transmission line 1220 comprising of outer conductor 1230 and inner conductor 1240. Microwave energy is introduced into the structure using a microwave connector 340. The inner conductor 1230 and outer conductor 1240 are preferable materials that have a high conductivity. The outer conductor 1240 may also provide a level of mechanical strength necessary to support the applicator structure.

In the arrangement shown in FIG. 18, inner conductor 1240 is connected or shorted to outer conductor 1230 at the distal end of the device and a plurality of holes 1242 (or slots) are made in outer conductor 1230. A plurality of nozzles 1131-1135 are provided, each connected to a respective hole 1242. In use a plasma plume is emitted from each nozzle 1131-1135.

Gas is introduced into the coaxial structure 1220 via gas feed 470, which is split into a plurality of supplies, each feeding a miniature valves 1231-1235 located opposite a respective nozzles 1131-1135. Each valve 1231-1235 may be manually or automatically adjustable to enable the flow of gas in the vicinity of each nozzle to be different and be such that plasma energy plumes are the same, i.e. the plasma energy produced by each plume is the same. For example, the valves 1231-1235 may be solenoid valves that are controlled using signals produced by controller 140. Alternatively, the valves 1231-1235 may also be manually adjusted using a screw or tap type mechanism.

The high voltage condition required to cause ionisation breakdown of gas supplied through valves 1231-1235 is provided by high voltage generator 1260, which produces high voltage pulses or spikes based on control signals provided by controller 140. High voltage generator 1260 may take the form of a low voltage generator with a voltage transformer that has a large turns ratio (e.g. 1:100, whereby a primary voltage of 10 V will produce a secondary voltage of 1 kV), a boost converter, a piezo-electric igniter, or the like.

Once the ionisation breakdown has occurred, the plasma will be maintained using the microwave energy produced by controllable microwave generator 2000. The microwave power from the generator sets up a microwave field inside the applicator to ensure plasma is emitted from each of the five nozzles.

Figure 19A:
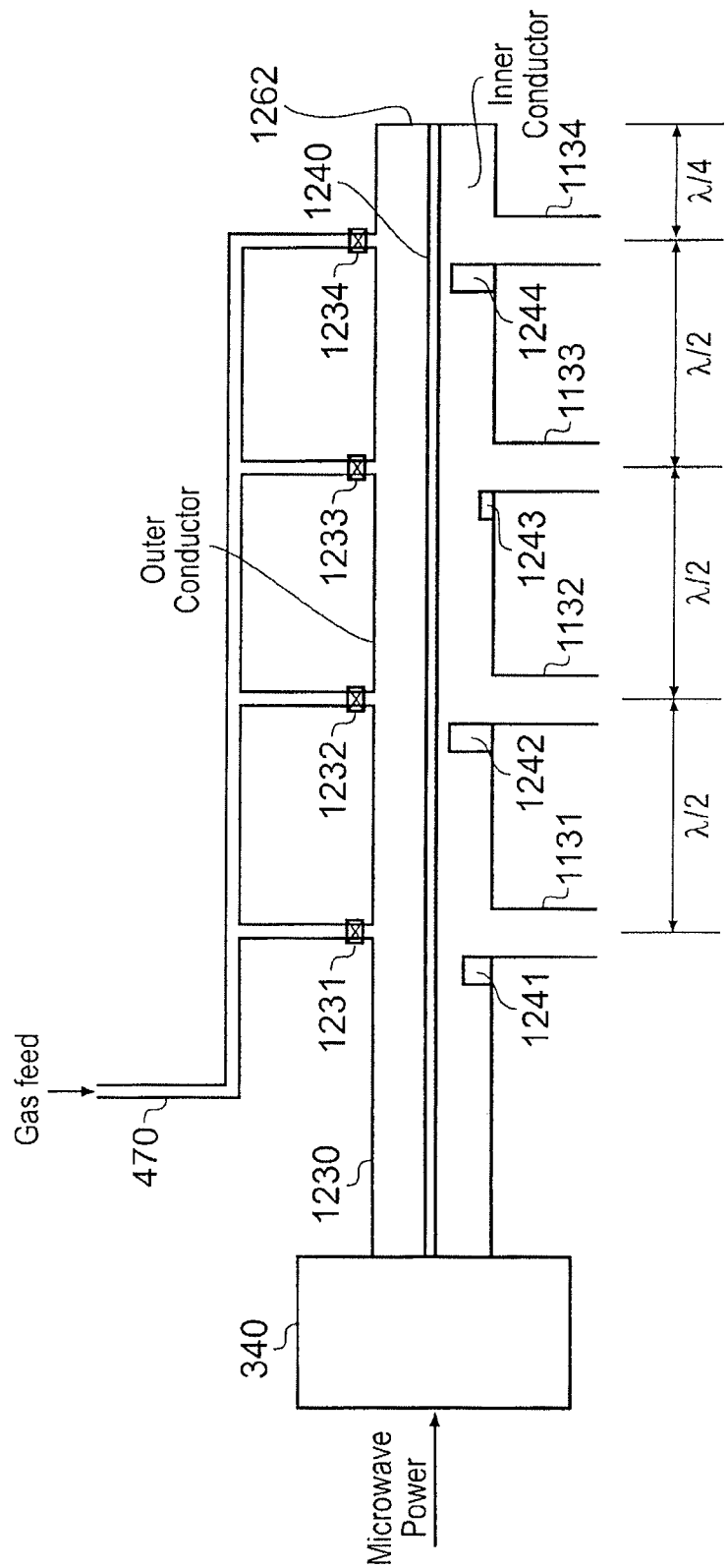
FIGS. 19a, 19b and 19c are schematic diagrams of a handheld coaxial plasma applicator with and without a dynamic tuning mechanism.
Figure 19B:
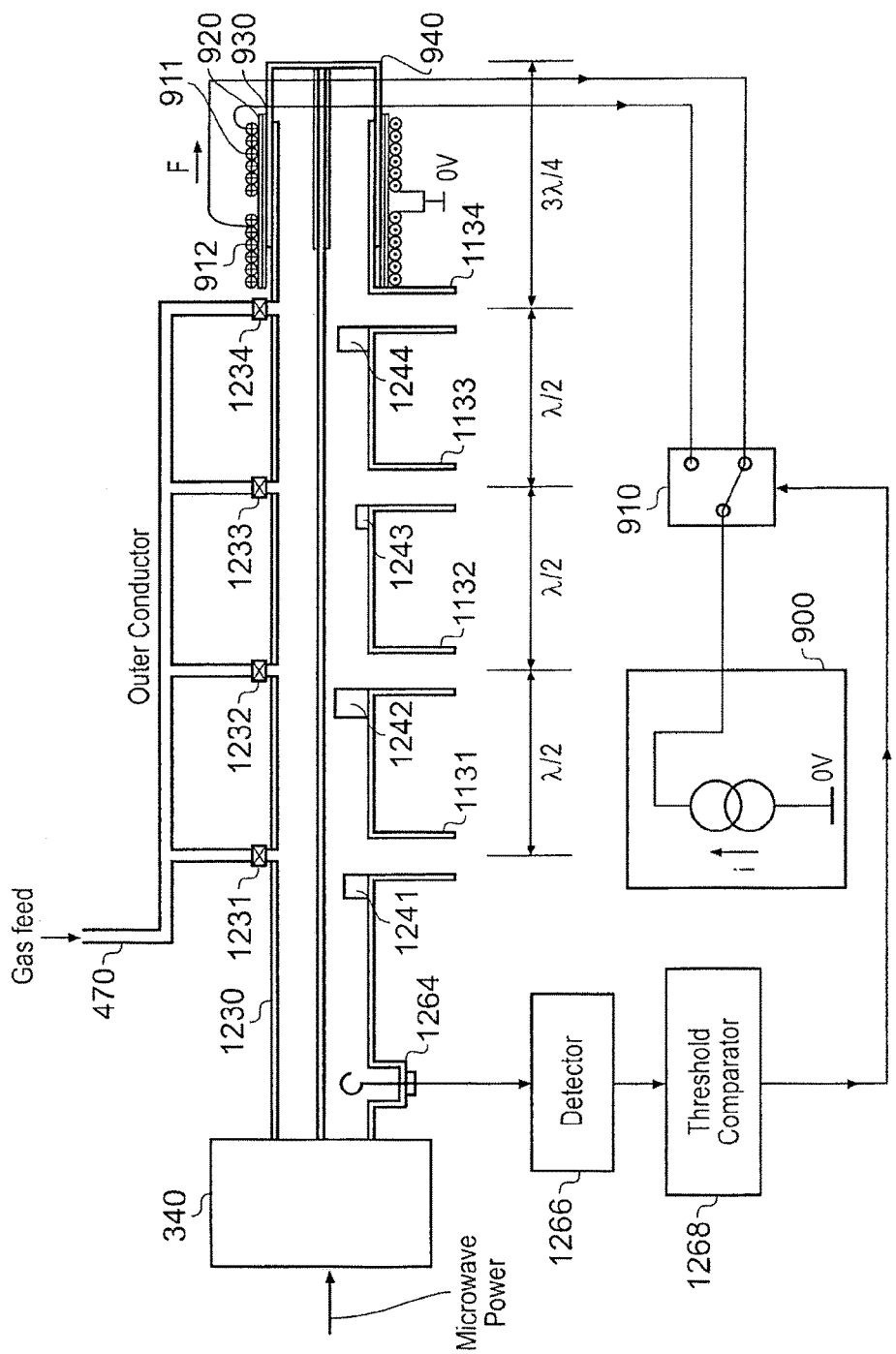
Figure 19C:
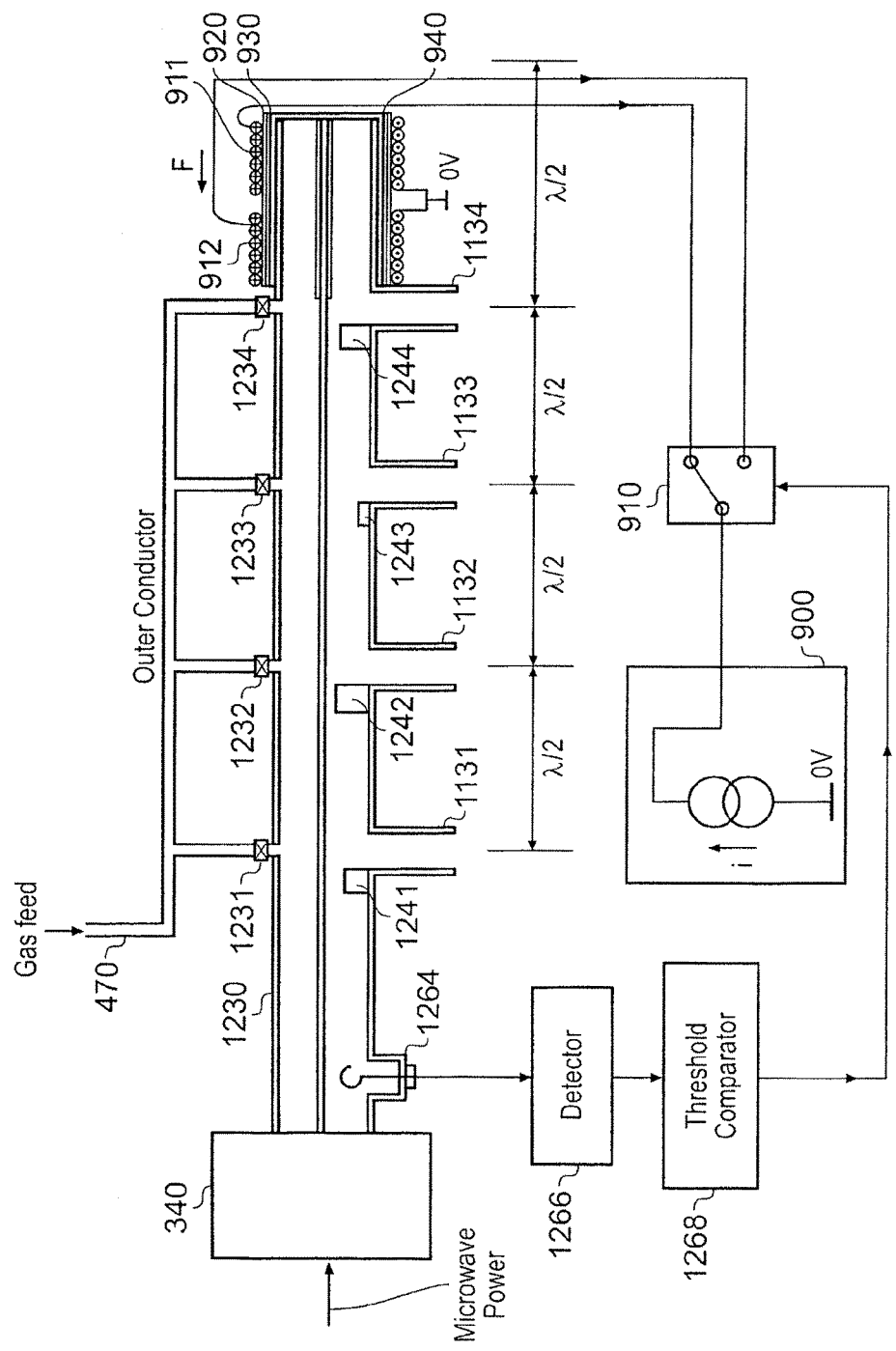

FIGS. 19a-19c shows a plasma applicator structure in which the microwave energy from the source is used to strike the plasma at the plurality of nozzles, i.e. in which a separate high voltage generator is not required.

FIG. 19a shows a structure that may be used to enable the microwave energy produced by microwave generator to initiate plasma at each of four nozzles 1131-1134. This arrangement shows the distal end of outer conductor 1230 shorted to inner conductor 1240 using shorting plate or end 1262. The centre of first nozzle 1134 is placed a distance of a quarter wavelength at the frequency of operation from said shorted end plate 1262 to provide a first E-field maxima (since a quarter wavelength rotation from a short circuit produces an open circuit), which is the preferred condition for an ionisation discharge or plasma strike to occur. The distance between the first nozzle and the second nozzle is then a half wavelength at the frequency of operation to enable the second E-field maxima to be positioned at the centre of second nozzle 1133 (a half wavelength rotation produces the same condition, i.e. a first open circuit condition to a second open circuit condition). The position of subsequent nozzles follows the same pattern to allow E-field maximums to be located at the centre of each remaining nozzle 1132, 1131. Gas is fed into the structure using an arrangement of valves similar to those shown in FIG. 18.

Ionisation discharges occur at the centre of nozzles 1131-1134 and variable gas flow rates along the length of the structure help to ensure a uniform line of plasma is produced along the length of the 'brush' or 'comb' arrangement. The distances between the centres of adjacent nozzles may be reduced by increasing the frequency of operation and/or by introducing dielectric or magnetic loading material into the structure in order to reduce the half wavelength.

As mentioned above, the microwave power may be modulated at a frequency and duty cycle that will enable a plasma to be continuously struck and emitted from nozzles 1131-1134, e.g. microwave source may be modulated at a frequency of 1 MHz with a duty cycle of between 10% and 80% to produce a range of sterilisation effects.

At each opening (slot) in the coaxial structure, a tuning stub 1241-1244 may be provided e.g. to fine tune the impedance to ensure that the electric field is concentrated enough to cause a plasma strike.

FIG. 19b shows a structure similar to that shown in FIG. 19a, but where the length of the shorted end section is variable. In this embodiment, a metallic cap 940 is mounted on the end of the coaxial structure. The cap 940 has a skirt that is inserted over outer conductor 1230 and a centre tube that slides over centre conductor 1240. The cap therefore performs the shorting function at the end wall. The outer wall of end section 940 is coated with a magnetic material 930, which assists with the movement of said end section 940 when a magnetising force F is present. End section 940 therefore forms the plunger or rod of a solenoid valve arrangement. The remaining components of the solenoid arrangement are two fixed solenoidal windings 911 and 912 and a fixed non magnetic former 920. The two windings 911, 912 are placed adjacent to one another and wound on top of non-magnetic former 920. Coated end section 940 will physically move when current from current source 900 is applied to either of the two windings 911, 912. As illustrated, first winding 912 is excited by current source 900, which sets up a magnetising force, which in turn sets up a physical force F to move end section 940 in a direction that extends the overall length of the applicator such that the distance between the end distal shorted end wall and the centre of first nozzle 1134 is three quarters of a wavelength at the frequency of operation. This enables E-field maxima to exist at the centres of each of the four nozzles 1131-1134, which enables plasma to be struck at each of the four nozzles.

The activation of first solenoid 912 is based on the field picked up by loop coupler 1264. The amplitude of the field is detected using detector 1266, which may be a diode detector, and the signal produced by detector 1266 is fed into threshold comparator 1268, which may be an operational amplifier with a voltage reference and a hysteresis circuit. The voltage level produced by threshold comparator 1268 is used to control the position of single pole double pole switch 910, which is used to channel the current produced by current source 900 to one of the two solenoid windings 911, 912.

Current source 900 may be a voltage controlled current source, where a voltage level produced by a DAC contained within microprocessor (not shown here) may be used to control the level of current fed into one of the windings 911, 912, which will determine the mechanical force produced and the movement of end section 940. Current source 900 may be a bipolar transistor or MOSFET based circuit or an arrangement using a power operational amplifier.

FIG. 19c shows a structure similar to that shown in FIG. 19b, but where the length of the shorted end section has been adjusted to provide the low impedance condition required to enable the plasma to be sustained. In this instance, loop coupler 1264 has detected the presence of a high E-field within the coaxial applicator and information is used to imply that the plasma has been struck. The voltage produced by detector 1266 toggles the output of threshold comparator 1268 and a control signal is sent to single pole double pole switch 910 to move the contact that routes the output of current source 900 to enable current to flow in second solenoid 911. Once second solenoid has been excited, it will produce a magnetisation force, together with a physical force, that is in the opposite direction to that previously set up to enable the movable shorted section to move to a position such that the impedance at the centre of nozzles 1131-1134 is reduced to enable the plasma to be sustained. In the arrangement shown in FIG. 19c, the new distance between the distal end wall that shorts the inner and outer conductors together and the centre of first nozzle 1134 is equal to a half of a wavelength at the frequency of operation, which will rotate the short circuit 180° on the Smith Chart back to a short circuit to provide the low impedance condition necessary to sustain plasma. The fixed half wavelength spacing between the centres of subsequent nozzles ensures that the same condition is set up at the centre of each of the four nozzles 1131-1134 to enable the plasma plumes to be sustained.

Figure 20:
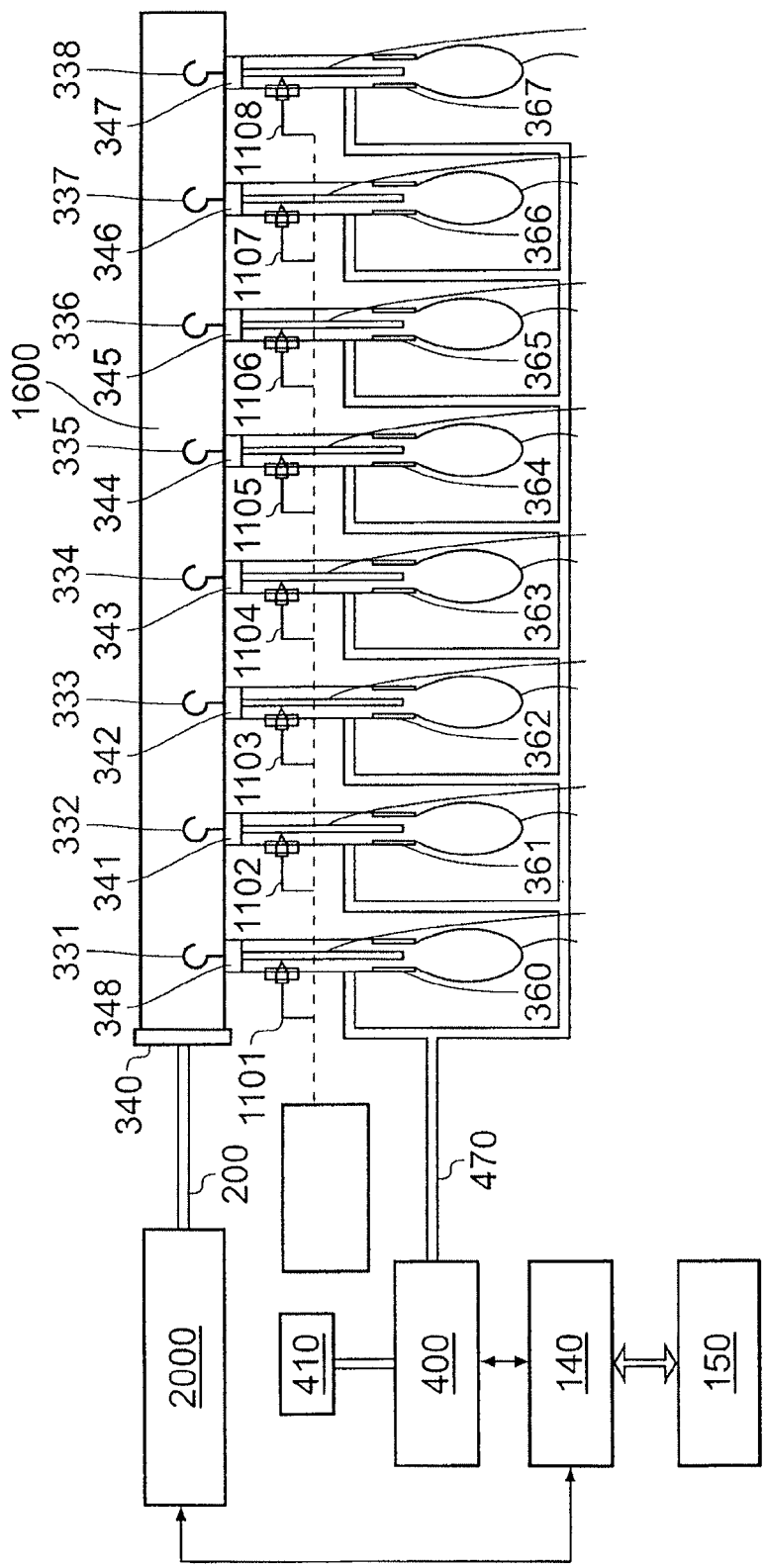
FIG. 20 is a schematic diagram of a handheld waveguide plasma applicator having a plurality of plasma generating regions.

FIG. 20 is a block diagram showing schematically another embodiment of a plasma 'brush' or 'comb'. In this embodiment, a power splitter or divider 1600 is used to divide the microwave power produced by microwave generator (or source) 2000 into a plurality of smaller power levels that are of equal amplitude and each one is used to drive a separate device that can produce plasma.

Power splitter 1600 may take the form of a microstrip or stripline power divider, a quarter-wave power splitter or a similar microwave structure that can be used to split microwave power into a plurality of equal parts. In this embodiment the power splitter 1600 divides the power between eight plasma applicators 360-367. Each plasma applicator is a coaxial transmission line connected to the power splitter 1600 using a connector 341-348, which may be SMA-type or N-type connector assemblies or the like. Each connector 341-348 has an H-field loop couplers 331-338 associated with it for transferring or coupling the microwave energy at the output of power splitter 1600 into the individual coaxial plasma applicators. The invention is not limited to using this particular coupling arrangement, i.e. it may be preferable to use E-field probe launchers or to couple the coaxial applicators directly to the outputs from power splitter 1600 using microstrip or stripline structures.

The inner conductor of each coaxial applicator may be arranged to transform the impedance seen at the launcher or power splitter 1600 to a higher or lower impedance in order to create or maintain plasma at the distal end of the applicator. For the arrangement shown in FIG. 20, one or more quarter wave impedance transformers may be provided in each plasma applicator. The quarter wave impedance transformers may transform the generator impedance seen at the outputs from power splitter 1600 into a lower impedance that matches into the plasma state after it has been struck, i.e. the structure is set up to maintain the plasma, but not to enable it to be initially generated or struck.

The plasma strike or initial breakdown of the gas may be produced by high voltage generator 1260 and igniters 1101-1108, which are coupled into the outer conductors of the coaxial applicators 360-367 in such a manner that a high electric field is generated between the inner and outer conductors when high voltage generator 1260 is activated by a control signal produced by controller 140.

The high voltage element of each igniter 1101-1108 may be a pointed conductor that can withstand high temperatures and high voltage without becoming damaged, e.g. tungsten rod or wire. The system used to generate the high voltage pulses or spikes may also be a boost converter that uses a low frequency oscillator, a switching device (MOSFET or BJT) and a coil or inductor, or a transformer whose primary is connected to a low voltage oscillator circuit with a suitable driver, an ignition coil arrangement or a piezoelectric igniter.

A supply of gas (or mixture of gases) is fed into each of the eight applicators via gas flow controller 400 and gas feed pipe 470. In this embodiment the gas feed is in parallel.

Figure 21:
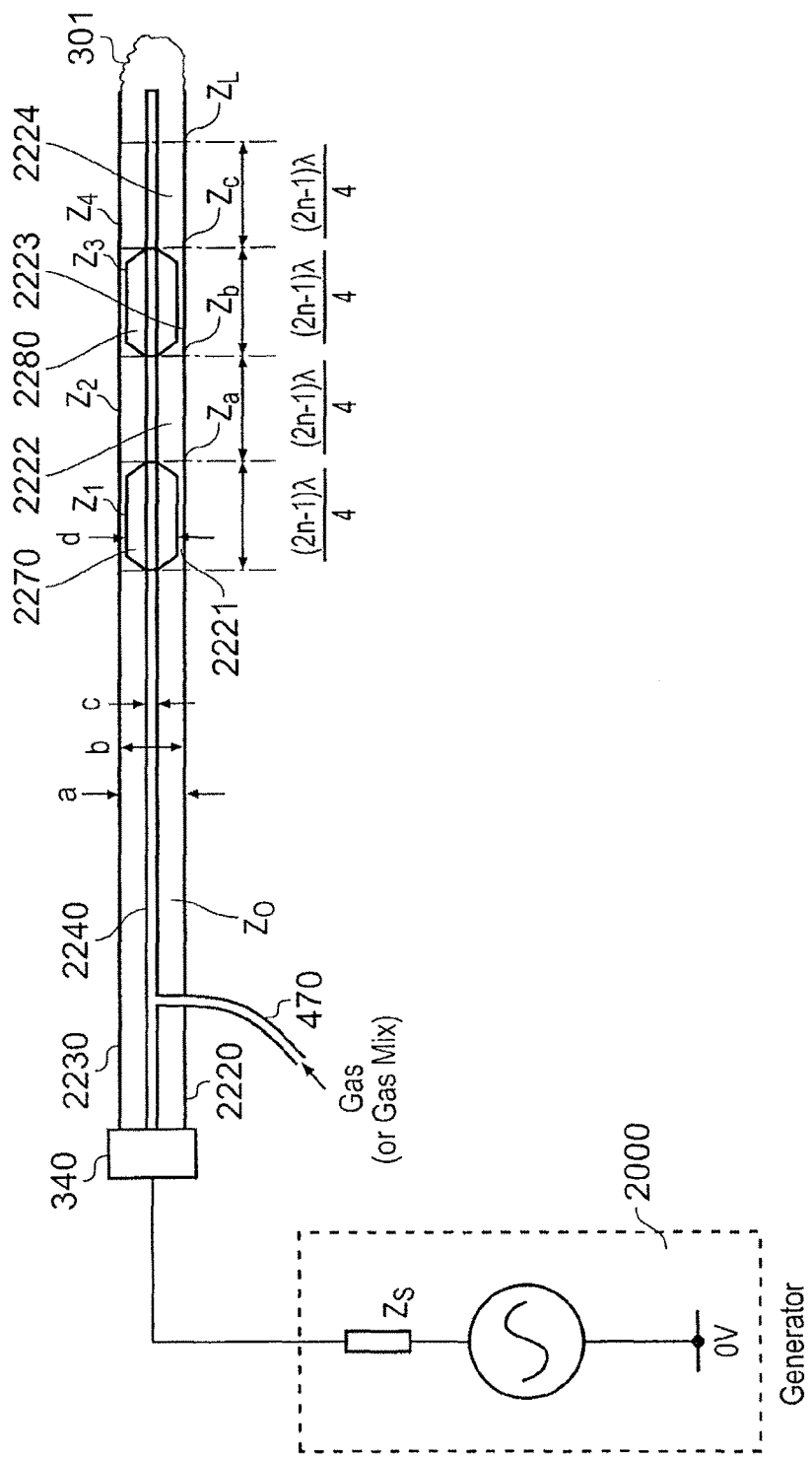
FIG. 21 is a schematic diagram of a coaxial plasma applicator suitable for insertion though an endoscope.

FIG. 21 shows an arrangement for a flexible instrument or applicator that can be inserted into the body through the instrument channel of an endoscope, through a tube or inserted directly into a natural orifice to sterilise tissue structures or items (inserts) placed inside the body using a plasma generated at the distal tip of the instrument from a microwave field and a suitable gas (or combination of gases). For this device, it is preferable for the outside diameter of the cable assembly α to be less than 3 mm and more preferably less than 2 mm to enable it to be inserted down the instrument channel of a standard surgical endoscope. The instrument consists of a coaxial cable assembly, which is preferably a flexible assembly, with an outer conductor 2230, an inner conductor 2240 to form the return and active conductors respectively and a dielectric material 2220 used to separate the two conductors 2230, 2240 from one another and provide constant characteristic impedance along the length of the cable assembly. The cable assembly used to transport microwave energy from the generator 2000 to the distal end of the applicator where plasma is generated. Inner conductor 2240 is hollow to enable a gas (or mixture of gases) to be transported along the coaxial cable assembly to the end of the applicator where plasma is generated. The end section contains an arrangement of impedance transformers 2221-2224 which are used to increase the voltage and electric field available at microwave generator 2000 to a value that can be used to cause ionisation discharge of the gas (or mixture of gases) at the end of the structure to enable suitable plasma to be produced.

In this embodiment, impedance transformers 2221-2224 contain no dielectric or magnetic loading materials. This means their length is solely dependent upon the microwave frequency of operation. It is preferable for the overall length of the end section of the instrument to be as small as possible, and so it is desirable to use transformers that are one quarter of the loaded or unloaded wavelength at the frequency of operation long to implement each of the four stages of the transformer. Note that the lengths that can be used are governed by the formula $$L = \frac{(2n-1)\lambda_0}{4},$$

where L is the physical length of the transformer, n is any integer and $\lambda_0$ is the wavelength at the frequency of operation. Accordingly, $\lambda_0/4$ will give the smallest transformer length that can be used.

It may be desirable for the operating frequency to be as high as is practicably possible, taking into account the relationship between insertion loss of the transmission line and the microwave frequency of operation. Insertion loss typically increases with frequency. If the operating frequency chosen is 24 GHz then the quarter wavelength will be 3.125 mm.

The gas (or mixture of gases) is fed into the coaxial structure using feed pipe 470, which is connected to centre conductor 2240 to enable gas to enter the structure and be transported along the cable. It may be preferable for the feed tube to be made from the same material as the dielectric material that fills the gap between centre conductor 2240 and outer conductor 2230 in order to minimise any discontinuity or mismatch produced at the feed point. It may be necessary to include a tuning stub to introduce a reactance that is of equal magnitude, but opposite sign to any reactance that may be produced by feed pipe 470 being introduced into the structure. In one embodiment the gas may be fed into centre conductor 2240 using a plurality of feed pipes, i.e. 2 or 4, wherein the feed pipes are positioned in such a manner that the reactance produced by one pipe is cancelled out by positioning the second pipe to produce a conjugate match. It may also be necessary to feed the gas into the structure using more than one pipe to enable the gas to flow along the centre conductor and reach the end, i.e. forces within the centre conductor and flow rates must be taken in to account when designing the hollow centre conductor.

Assuming that the transformer sections are not loaded with a dielectric and/or magnetic material then the characteristic impedances $Z_1$-$Z_4$ of the transformers 2221-2224 shown in FIG. 21 may be calculated as follows $$Z_1 = Z_3 = 138 \log_{10} \frac{b}{d}, \text{ and}$$

$$Z_2 = Z_4 = 138 \log_{10} \frac{b}{c},$$

where b is the diameter of the inner surface of the outer conductor 2230, c is the diameter of the outer surface of the inner conductor in the second and fourth transformers 2222, 2224, and d is the diameter of the outer surface of the widened inner conductor 2270, 2280 in the first and third transformers 2221, 2223.

If it is assumed that the generator impedance $Z_S$ is moved to the input end of the first impedance transformer, i.e. $Z_S$ is connected to $Z_1$, the load impedance $Z_L$ can be expressed as $$Z_L = \frac{Z_4^2 Z_2^2 Z_S}{Z_3^2 Z_1^2}.$$

Assuming that the length of the transmission line that carries or holds the four transformer sections is lossless, i.e. ignoring power loss along the length of the structure, then the input power going into the structure is the same as the output power coming out at the end of the structure, and the electric field E set up at the distal end of the fourth impedance transformer, used to create the ionisation discharge, can be expressed as $$E = \frac{\sqrt{P_{out} Z_L}}{\ell},$$

where $P_{out}$ is the output power and l is the distance between the tip of centre conductor contained within the fourth transformer and the inner wall of the outer conductor of the applicator (which in this case is $$\frac{b-c}{2}).$$

A practical embodiment may be as follows:
inner diameter of outer conductor b=1.97 mm
outer diameter of inner conductor C for second and fourth quarter wave sections=0.4 mm
outer diameter of inner conductor d for first and third quarter wave sections=1.8 mm
according to equations listed above, $Z_1$=$Z_3$=5.4Ω and $Z_2$=$Z_4$=95.6Ω
assuming the source impedance $Z_S$ is 50Ω and given that l is 0.785 mm and $P_{out}$ is 25 W:
$Z_L$=4.9 MΩ,
Output voltage $V_L$=11 kV, and
E=14 MV/m.

It can be seen from this analysis that this arrangement may be used to create extremely large electric fields to enable suitable ionisation discharges of air and a number of gases (or gas mixtures) to be created in small applicator structures to enable plasma to be produced at the end of flexible cable assemblies that are of small enough outer diameter and of long enough length to be inserted down the instrument channel of standard surgical endoscopes or similar devices.

The fact that a transmission line exists between generator impedance $Z_S$ and the first transformer $Z_1$ means that a portion of the power produced by generator 2000 will be lost by the time it reaches the first transformer, but since the generator impedance $Z_S$ is the same as the characteristic impedance of the transmission line $Z_0$, there will be no impedance mismatch or standing wave to take into consideration. For example, if the impedance of the generator and the characteristic impedance of the transmission line is 50Ω, the power available from the generator is 47 dBm (50 W), and the insertion loss of the transmission line is 3 dB, then the power at the end of the transmission line (or that at the input to the first transformer) will be 44 dBm (25 W), and the impedance seen at this point will also be 50Ω.

It is preferable for the ends of the low impedance transformer sections (the large diameter cylinders) to be tapered so as to minimise discontinuities within the microwave structure, or to make the transition from the first impedance to the second impedance as gradual as possible.

It is preferable for the materials used for the inner and outer conductors of the transmission line 2230, 2240 respectively and the transformer sections 2221-2224 to have a low conductor loss at the frequency of operation. Suitable materials include: silver plated copper, brass, gold or aluminium. The outer body of these sections may be plated with high conductivity materials to a thickness of around five skin depths at the frequency of operation where the majority of the microwave energy will be transported.

It is preferable for the dielectric material used to be low loss at the frequency of operation, i.e. low density PTFE may be used.

A suitable cable assembly that may be used to implement the current invention is the Multiflex_86 cable from Huber & Suhner.

Table 6 provides insertion loss and maximum CW power handling data for the cable assembly at a range of discrete operating frequencies.

TABLE 6

Insertion Loss and CW Power Handling for Multiflex_86 cable

| Frequency (GHz) | Insertion Loss (dB/m) | Maximum CW Power (W) |
|---|---|---|
| 2.0 | 1.07 | 99 |
| 4.0 | 1.55 | 70 |
| 6.0 | 1.93 | 57 |
| 8.0 | 2.26 | 49 |
| 10.0 | 2.56 | 44 |
| 12.0 | 2.83 | 40 |
| 14.0 | 3.09 | 37 |
| 16.0 | 3.33 | 35 |
| 18.0 | 3.56 | 33 |
| 22.0 | 4.0 | 30 |
| 24.0 | 4.21 | 29 |

It may be preferable to modulate or pulse the microwave energy in order to enable higher peak power levels to be available at the end of the cable assembly to drive the applicator, i.e. it may be possible to increase maximum CW power level from 29 W at 24 GHz to 290 W if using a 10% duty cycle pulsed modulation.

Another embodiment of the invention may provide a hand hygiene system comprising an enclosure for receiving a pair of hands, one or more plasma jets located in the enclosure, and one or more proximity sensors arranged to sense an object in the enclosure, whereby the row of plasma jets are arranged to move over the surface of the object. The plasma jet(s) may be arranged to scan in two or three dimensions. Alternatively, a row of jets may be provided which scan in one dimension. Two or more rows may be provided.

The system may include a temperature sensor arranged to measure the temperature on the surface of the hand and use this information in a control loop to adjust system, e.g. power delivered by the plasma or distance between the applicator and the hand. Alternatively a physical spacer may be provided in the enclosure to fix a minimum separation between the hand and plasma jets.

Clinical Applicability

A number of potential clinically related applications for the current invention have been identified by clinical workers, physicians and the inventor.

One application that has been identified is in open wounds for cleaning wounds or wound beds from bacteria prior to a patient having a skin graft or having a covering placed over the wound such as tissue-engineered skin. In this instance, the invention is used to 'spray' plasma over the region where the new skin is to be placed in order to ensure that the wound is clean and free from bacteria. In this application, the plasma must totally eradicate or kill or destroy all bacteria that exists in the wound. If tissue engineered skin is to be used to replace the natural skin then it may also be possible to use the current invention to remove bacteria or viral infection from the materials used to create the tissue engineered skin structure.

In summary, the invention may be used as follows for this particular application:

the controlled plasma system may be used to remove bacteria from the wound bed;

the controlled plasma system may be used to sterilise or clean the materials used to create the artificial skin to remove bacterial or viruses prior to the material being attached to the wound bed.

Furthermore, the invention may be applied in wound bed sterilisation, killing bacteria manifested in cuts that have not been properly cared for, pre- and post-operative treatment, e.g. to remove bacteria from the surface of the body (e.g. using a wand-shaped applicator) before opening up a patient, and spraying into the body before closing up the patient to ensure no bacteria has got in during the operation, and cleaning surgical equipment, e.g. spraying plasma over the surgeon's gloves before he/she touches the patient.

A second application is in the treatment of sexually transmitted diseases where a small plasma jet may be inserted inside a natural orifice, for example, the mouth, vagina, or penis and the plasma may be used to significantly reduce the bacteria caused by the disease. This treatment solution may overcome drawbacks of currently used antibiotic treatment for gonorrhoea where the disease has become resistant to various antibiotic treatments that have been developed.

The current invention may also lend itself well for killing the bacteria in contained within ulcers (sores). This feature may be particularly useful for people that are otherwise hospitalised. If the bacteria can be removed from an ulcer then the ulcer may begin to heal and the patient may be able to go home to their family where they can be looked after (this would not be possible if the bacteria remained in the ulcer).

The current invention may be useful for the treatment of athlete's foot, whereby the plasma is used to kill the fungus that is formed on the surface of the skin and, in particular, between the toes. The current invention may also be used to treat contact dermatitis and athlete's foot. For example, an 866 MHz microwave source producing up to 300 W of power with a modulation frequency of 400 KHz and a 20% duty cycle may be used to set-up an atmospheric plasma inside a co-axial structure that consisted of two quarter wave impedance matching transformers. In preliminary tests a positive result was obtained when the plasma was administered to a human foot that was infected with athlete's foot and suspected contact dermatitis. Two treatments were undertaken on two consecutive days, each treatment lasted for a period of around 60 seconds. No pain or discomfort was felt by the patient and a significant improvement was found after the second treatment.

It has been identified that the current invention may also be used to sterilise areas or places where bacteria grows or where viruses are present, for example, hospital wards or operating theatres. The invention may be particularly interesting for treating the bacterium called *Clostridium difficile*.

The current invention may also be useful for treating the MRSA virus. In particular, the invention may be used to reduce or destroy all MRSA bacteria that exist inside the nostrils of diagnosed patients or hospital staff, visitors or others that may be carrying the bacteria. It is known that up to a third of the population carry the MRSA virus, but it is mostly contained in the benign state.

The current invention may also be used to kill germs or treat viruses that manifest in regions of the body or externally where it is difficult to clean using conventional cleaning methods, for example, using detergent or other liquid cleaners.

The current invention may be used in a hospital environment or a clinic or an outpatient surgery for effective sterilisation or decontamination of the following external areas: general surfaces, beds, desks, chairs, doctor's notes, pens, medical instruments (mechanical and electrical) and floors. The current invention may be realised in a form whereby it is possible to place items inside the unit for sterilisation, i.e. pens, etc The current invention may also be used to kill bacteria on the hands and, in particular, inside the nails where bacteria or germs can manifest and are difficult to access using conventional cleaning methods. This may be particularly interesting for the treatment of MRSA, which appears to be transmitted through touch and objects used by surgeons, such as pens and clip boards.

The current invention may be particularly useful for treating bacteria and viral diseases that exist or manifest in natural orifices within the human body, for example, the mouth, nostrils, the ear, the vagina, the cavity of the cervix, the penis and the anus or further back inside the rectum. In these regions of the body it is necessary for a certain amount of the bacteria to be present and so, in this instance, the invention shall be used to destroy only a portion of the bacteria, for example, 95%.

The current invention may be used for effective treatment of sexually transmitted diseases (STDs) or sexually transmitted infections (STIs). In this application it will be necessary to be able to determine the amount of bacteria that the system should destroy as for this application, it is likely that the system shall be used to reduce the level of bacteria present rather than trying to eradicate all bacteria. In this instance, the ability to finely control the amount of plasma delivered into the tissue or onto the surface of the tissue will be of paramount importance. The use of a controllable solid state source that can be modulated up to and in excess of 100

KHz may be a highly desirable feature for implementing a system that is suitable for use in this application.

The current invention may be used for personal hygiene, for example, it may be used in bathrooms to sterilise toilets, sinks and urinals. It may even be advantageous for people to own their own unit so that they can make use of its sterilisation features when travelling to foreign countries or regions where there is not such a strong emphasis on personal hygiene.

The current invention may also be used to clean polluted water, for example, in a swimming pool or a water treatment system.

A particular attraction of the current invention is that it may be used to ensure that the bacteria or virus is treated (reduced) or completely destroyed in a localized or selective manner.

One particular application for hospital sterilisation is where visitors of leukaemia sufferers should have their hands and feet sterilised prior to entering the clean room environment where the patient is located.

The current invention may also be used for the treatment of benign or malignant skin tumours. For effective use in this application, it is preferable for the plasma to be generated that creates temperatures on the surface of the skin that is greater than 10° C. above room temperature.

The current invention may be arranged in such a manner that a plurality of small size plasma jets, for example, 12 jets with an outside diameter of 2.5 mm, form a comb or brush and said comb or brush is brushed over the surface of the scalp or skin to treat sebhorraic dermatitis. This application may be of particular interest to the elderly for brushing through their hair.

Plasma may be used to treat bacteria on the surface of the skin caused by acne or sebhorraic dermatitis.

The current invention may be used to treat alopecia, where it is necessary to stimulate the hair follicles. In this application, it may be desirable for the energy to penetrate to a depth of less than 1 mm, for example, 100 μm. For effective treatment in this application it is highly desirable to be able to control the energy delivery into the tissue. This may be achieved by controlling the level of microwave power, the modulation frequency (pulse on/off times), the microwave frequency and the gas flow/mixture combination.

The current invention may also be used to change cell pigmentation or to correct pigmentation defects. Melanocyte cells are responsible for providing skin colour and these are found in the lower layer of the epidermis, therefore, it may be practically possible to use the controlled plasma treatment system to affect these cells.

The current invention may be used for cleaning blisters or for the treatment of blistering diseases such as congenital naevi.

The current invention may be also be used for the treatment of Rendu-Osler syndrome. Rendu-Osler disease or hereditary hemorrhagic telanjectasia is an inherited antosomal dominant trait, which is characterised by the development of telanjectases on the skin, mucous and internal organs with recurrent haemorrhages. The plasma applicators developed for the current invention may be inserted inside regions of the body where the mucous is produced or inside various internal organs. This application may draw on the ability to produce applicators with outside diameters of less than 5 mm.

Other clinical applications where it has been identified that the current invention may be useful are:

fish tank granuloma, where bacteria is released as a foreign body into the skin and causes inflammation of the skin;

to decontaminate baths and water that may be contaminated and where people have been known to get legionaries disease, which may lead to pneumonia and is a big social problem;

for the potential treatment of bird flue where the plasma may be used to treat the bird prior to it flying out of its cage.

Some of the potential uses discussed above are considered in further details below.

Wound Bed Application

The current invention may be used to clean a wound or a wound bed in regions of the body where skin that has been removed from the body by accident or through disease is to be replaced by performing skin grafts or by replacing the missing skin with tissue engineered skin.

Any loss of full thickness skin of more than 4 cm in diameter will not heal without a skin graft being performed. In cases in which considerable amounts of skin are needed, the standard approach is to take split thickness grafts that contain all of the epidermis but only parts of the dermis. These are removed from healthy areas of the body and used to treat the damaged areas. Patients will regrow an epidermis from the source sites if there are sufficient epidermal cells remaining in the residual dermis. The current invention may be used not only to 'clean' the wound bed upon which the skin taken from the skin graft is to cover, but also to ensure that bacteria can not or does not enter the regions where the skin has been taken.

Before tissue engineered skin being available for replacing large areas of skin, surgeons had to avoid making the patient's condition worse by removing too much healthy skin.

Acute burns remain a major healthcare problem in developing countries. On the other hand, in the developed world, life expectancy and affluence have increased so markedly that chronic wounds, associated with ageing and diabetes, have started to become significant. Repeated skin grafts or tissue engineered skin treatment are expensive to the healthcare system and to the patient. Patient suffering due to skin replacement not working due to bacteria residing underneath the new skin layer can cause considerable patient discomfort and in many cases has been known to lead to death of the patient.

Skin comprises of several different cell types. Keratinocytes are the most common cell type in the epidermis and are used to form the surface layer. Melanocyte cells are found in the lower layer of the epidermis and these are responsible from providing skin colour. Fibroblasts form the lower dermal layer and are used to provide strength and resilience.

Application of skin cells, such as keratinocytes or fibroblasts, autologous (from the patient), or allogeneic (from a donor) offer some benefit to non-healing chronic wounds in terms of prompting them to restart healing. Cultured cells are being used as biological 'factories' to assist the body's own healing mechanisms.

Bacteria may also get into the open skin during reconstructive surgery or scar revision, thus, the current invention may be used prior to these treatments taking place.

Most tissue engineered skin is created by expanding skin cells in the laboratory at a rate that is much greater than when on a patient. These cells are then used to restore the barrier function, which is the primary objective for treating burns patients, or to initiate wound healing, e.g. in chronic non healing ulcers.

Other examples of the use of tissue engineered skin are: accelerating healing, reducing pain in superficial burns, and for correcting conditions in which healing has been suboptimal.

Skin must be capable of regeneration, so although synthetic materials can be used temporarily to provide a barrier, a dermal matrix, or a transfer mechanism, for long term healing all synthetic materials must be discarded and replaced by natural live skin cell growth.

Any cultured cell material carries the risk of transmitting viral or bacterial infection. Some support materials, such as bovine collagen, may also carry a risk of disease. The current invention may also be used to 'clean' the materials to ensure that the tissue engineered skin cannot be the carrier of viral or bacterial infection when introduced onto the patient.

The current invention may, therefore, help promote the use of tissue engineered skin as the proper sterilisation of the materials used will help reduce risk of infection to the patient and this may be the underpinning factor for its use.

Before tissue engineered skin can be used, there must be clear evidence that the materials can provide benefit to the patient. One of the essential characteristics of tissue engineered skin is that it heals well; in order to achieve this, the tissue engineered skin must attach well to the wound bed, be supported by new vasculature, not be rejected by the immune system and be capable of self repair throughout the patient's life.

Sexually Transmitted Diseases

The current invention may be used to selectively reduce or kill bacteria or viral diseases that exist in an environment located inside the human body and one particularly useful application for this feature is to treat a number of sexually transmitted diseases. In these applications it is required to insert the applicator inside various natural orifices contained within the human body, e.g. the vagina, the rectum, penis, or the mouth, where the plasma may be used to significantly reduce, or completely destroy, the bacteria caused by the disease. In such an application it is possible for pressure to build up within the body cavity, and it is highly undesirable for this pressure, caused by the gas (or gas mixture), to build up since this may lead to damage being caused to the organ of interest, therefore, some form of exhaust or extraction system is required. This invention may be particularly suitable for treating *Chlamydia* or Gonorrhoea where it is preferable to completely destroy or kill the cells. In this application, the treatment solution may overcome drawbacks of currently used antibiotic treatments where the disease has become resistant to various antibiotic treatments that have been developed by leading drug companies.

Sexually transmitted diseases (STDs) or sexually transmitted infections (STIs) are diseases that can be transmitted through body contact during sex. They are caused by viruses, bacteria, and parasites. There are at least 25 different STDs and they are caused by many different types of bacteria and viruses. They all have one common feature and this is that they are spread by sexual contact through the vagina, the mouth or the anus.

The most common STDs are *Chlamydia*, gonorrhoea, genital herpes (Herpes genitalis), genital warts, and syphilis.

For treatment of some of these diseases it is necessary to completely destroy the bacteria, whereas for others it may be highly desirable to significantly reduce the levels of bacteria rather than completely wiping it out due to the fact that this may destroy the body's natural flora.

Embodiments of the current invention may include applicators that can be inserted inside the vagina, the mouth, or the anus. These applicators may be of diameter such that they can be inserted into the orifice without causing pain or discomfort to the patient. The system can be set-up to enable controlled plasma plumes to be emitted at the distal end of the applicators and the plasma may be used to destroy or reduce the bacteria. In this particular application, the temperature of the plasma will not exceed body temperature to ensure that no tissue damage can be caused by excessive heating of the tissue. In this application, the plasma may be produced using a combination of helium or argon with compressed air or oxygen. The microwave power level, modulation frequency, duty cycle, and gas flow rate are controlled to enable the plasma to be optimised to create the most desirable clinical effect.

Hospital Ward Cleaning

The current invention may also be used to kill bacteria that may exist in an environment that is defined as being located outside the human or animal body, for example, within a hospital ward, an operating theatre, an outpatient surgery, or within the home. The current invention may be used to kill bacteria existing in both of these environments. One application for the current invention is to kill bacteria linked with healthcare associated infections (HCAIs). There is a growing concern that HCAIs are increasing. Addressing HCAIs is currently of high priority and a significant problem not only within the UK, but also in other countries throughout the world. With HCAIs, not only is the safety and wellbeing of patients compromised but the resources consumed by potentially avoidable infections is ever increasing.

Some forms of the HCAIs are mutating and becoming more resilient to heat and cleaning agents and are therefore very good at establishing themselves in hospitals. Treating patients with antibiotics has the adverse affect of exacerbating the stronghold of the HCAIs. The HCAIs are generally spread through cross human infection or via a contaminated environment around a patient. With certain HCAIs, the bacterium takes the form of spores excreted in the patient's faeces, which can then contaminate the general area around the patient's bed. With aggressive strains this can then lead to hospital wide outbreak, where patients and wards have to be completely isolated, thus hospital resources that are already limited and currently stretched to breaking point, become even more loaded.

Various prevention and control methods are used or being considered to prevent the onset of HCAIs. These include cleaning the wards at night times where the through traffic is considerably lower, isolation of infected patients, hand washing, wearing gloves and aprons, and use of enhanced cleaning agents and methods. Conventional cleaning methods using standard detergents can have the detrimental effect of spreading the HCAIs and so this procedure should be avoided. One particular HCAI that is currently receiving much interest is *Clostridium difficile* infection (*C. difficile*). *C. difficile* is now recognized as the major causative agent of colitis (inflammation of the bladder) and diarrhoea that may occur following antibiotic intake. *C. difficile* infection represents one of the most common hospital infections present around the world. In the USA alone, it currently causes around three million cases of diarrhoea and colitis per year. The bacteria associated with *C. difficile* is primarily acquired in hospitals and chronic care facilities following antibiotic therapy covering a wide variety of bacteria and is the most frequent cause of diarrhoea in hospitalised patients.

A characteristic of *C. difficile* associated diarrhoea and colitis is its high prevalence among hospitalized patients, thus *C. difficile* contributes significantly to length of stay in hospitals and may be associated in some elderly adults with chronic diarrhoea, and other potentially life threatening consequences. The *C. difficile* bacterium infections involve extensive extended spells in hospital and can even be fatal if the disease progresses unfavourably.

Some hospitals have resorted to using high pressure steam cleaning combined with toxic substances. However, this requires that whole wards have to be evacuated and isolated with all gaps between doors sealed. Even with these cleaning measures in place, the spores are not necessarily completely destroyed but merely washed off hard surfaces. Unfortunately, these cleaning methods do not apply to soft fabric based furnishings in the hospital which can therefore still remain infected. The current invention will be effective for use on fabric furnishings. The current invention also overcomes many of the problems listed above and may offer a viable alternative solution.

The current invention detailed here may be used to eradicate the HCAIs by targeting the bacteria locally. The current invention may be used to decontaminate medically controlled environments, for example, hospital wards, outpatient surgeries, etc.

The current invention may also be used to treat certain bacterial infections, for example, methicillin-resistant *Staphylococcus aureus* (MRSA) that do not respond or have become less responsive to certain antibiotics, MRSA is a type of bacterium commonly found on the skin and/or in the nostrils of healthy people. Although it is usually harmless at these sites, it may occasionally get into the body, for example, through breaks in the skin such as abrasions, cuts, wounds, surgical incisions or indwelling catheters, and cause infections. These infections may be mild resulting in pimples or boils, or more serious, for example, infection of the bloodstream, bones or joints may occur.

The treatment of infections due to *Staphylococcus aureus* was revolutionised in the 1940s by the introduction of the antibiotic penicillin. Unfortunately, most strains of *Staphylococcus aureus* are now resistant to penicillin. This is because *Staphylococcus aureus* has 'learnt' to make a substance called β-lactamase, that degrades penicillin, destroying its antibacterial activity.

Some related antibiotics, such as methicillin and flucloxacillin, are not affected by β-lactamase and can still be used to treat many infections due to β-lactamase-producing strains of *Staphylococcus aureus*. Unfortunately, however, certain strains of *Staphylococcus aureus*, known as MRSA, have now also become resistant to treatment with methicillin and flucloxacillin.

Although other types of antibiotics can still be used to treat infections caused by MRSA, these alternative drugs are usually not available in tablet form and must be administered through a drip inserted into a vein.

MRSA infections most often occur in patients in hospitals and are rarely seen among the general public. As with ordinary strains of *Staphylococcus aureus*, some patients harbour MRSA on their skin or nose without harm (such patients are said to be 'colonised'), whereas other patients may develop infections. Some patients are at increased risk of developing infection; these include: those with breaks in their skin due to wounds (including those caused by surgery), indwelling catheters or burns, and those with certain types of deficiency in their immune system, such as low numbers of white cells in their blood.

When MRSA spreads from an initial site of colonisation to a site where they cause infection in the same patient, i.e. spread from the colonised nose to a wound, the resulting infection is described as 'endogenous'.

In addition to causing endogenous infections, MRSA can spread between patients, usually by direct or indirect physical contact. For example, hospital staff attending to a colonised or infected patient may become contaminated or colonised with MRSA themselves (perhaps only briefly). They may then spread the bacteria to other patients with whom they subsequently have contact. These patients may in turn become colonised and/or infected. The spread of MRSA, or other bacteria, between patients is known as cross-infection and techniques to prevent this from occurring will offer significant advantage.

Some strains of MRSA that are particularly successful at spreading between patients may also spread between hospitals, when colonised patients, or staff, are moved from one hospital to another. These strains are known as epidemic MRSA (or EMRSA).

The plasma sources and applicators developed for use in the current invention may be used to destroy the MSRA bacterium by introducing the energy into the body non-invasively using natural orifices or minimally invasively by producing a man made channel or orifice. Suitable applicators or antennas may be introduced into this orifice. The current invention may also be used to 'disinfect' those with a high risk of attracting MSRA, for example, patients or nurses, by exposing certain regions of the body, for example, the hands or the nose, to focussed plasma where it is preferable for the maximum temperature reached at the biological tissue treatment site is limited to be less than 10° C. above room temperature.

A further point that should be noted is that with the use of conventional sterilisation techniques, i.e. disinfectants, it is very difficult, if not impossible, to sterilise general items that require handling on a day to day basis, for example, pads of paper, documents, paper money, files, pens, books and report lists. The current invention may be used to sterilise these items prior or subsequent to use. The current invention may also be used to sterilise various hospital furnishings, such as window curtains, ward curtains and food trays.

For this application, the current invention may be implemented as a plurality of plasma jets located around a door or entrance to a hospital ward in order to sterilise the person as they walk through.

Embodiments of the current invention that may be suitable for this application include a plurality of plasma jets that take the form of a floor brush or a device that can be wiped over surfaces. The microwave power requirements for implementation of devices that are suitable for this application may be greater than those required to implement the other applications, for example, power levels in excess of 10 kW may be required. This requirement may be met using a plurality of solid state sources or microwave tube or resonant cavity sources may be considered.

Due to the nature of the operating environment for this particular application, it may be desirable to use plasma at elevated temperatures, i.e. above body temperature. The requirement here will be to ensure that the materials being sterilised are not damaged in any way by the plasma plume or beam.

The invention claimed is:

1. A plasma sterilization apparatus comprising:
   a plasma applicator having an enclosed plasma generating region and an outlet for directing plasma out of the plasma generating region towards a surface to be sterilised;
   a microwave radiation generator connected to deliver microwave energy into the plasma generating region; and a common cable assembly arranged to transport simultaneously the microwave energy and gas to the plasma generating region, wherein the common cable assembly comprises a coaxial transmission line formed from an inner conductor, an outer conductor and a dielectric material separating the inner conductor from the outer conductor, wherein the inner conductor has a longitudinal bore therethrough for transporting the gas to the plasma generating region.

2. The plasma sterilization apparatus according to claim 1, wherein the common cable assembly comprises a longitudinal passageway formed beyond the outer conductor for transporting residual gas away from the plasma generating region.

3. The plasma sterilization apparatus according to claim 2, wherein the longitudinal passageway terminates at a reservoir from which the gas is re-introduced to the longitudinal bore.

4. The plasma sterilization apparatus according to claim 1, wherein the coaxial transmission line comprises a flexible tube made from the dielectric material, and wherein the inner conductor is conductive coating on an inner surface of the flexible tube and the outer conductor is a conductive coating on the outer surface of the flexible tube.

5. The plasma sterilization apparatus according to claim 1, wherein the common cable assembly has an outer diameter of less than 3 mm.

6. The plasma sterilization apparatus according to claim 1, wherein the common cable assembly comprises a coaxial waveguide arranged to support the propagation of a transverse electromagnetic (TEM) wave.

7. The plasma sterilization apparatus according to claim 6, wherein the coaxial waveguide has an outer conductive wall located inside a protective jacket, and wherein a channel for transporting the gas is formed between the outer conductive wall of the waveguide and an inner wall of the protective jacket.

8. The plasma sterilization apparatus according to claim 1, wherein the common coaxial cable assembly has a first physical diameter, and wherein the plasma applicator comprises a hollow coaxial structure forming an instrument having a second physical diameter which is the same as the first physical diameter of the common coaxial cable assembly, and wherein the plasma applicator has an impedance transformer arranged to multiply a voltage at a distal end of the transmission line to strike the plasma.

9. The plasma sterilization apparatus according to claim 1 further comprising a radiofrequency (RF) source, wherein the common cable assembly is arranged to transport RF energy from the RF source to the plasma generating region to strike the plasma and to transport the microwave energy from the microwave radiation generator to sustain the plasma.

10. A plasma sterilization apparatus comprising:
a plasma applicator having an enclosed plasma generating region and an outlet for directing plasma out of the plasma generating region towards a surface to be sterilised;
a microwave radiation generator connected to deliver microwave energy into the plasma generating region; and
a coaxial waveguide or transmission line arrangement comprising a tube of flexible dielectric material having a center section bored out or extruded to form a channel for directing a gas to the plasma generating region,
wherein the microwave energy has a frequency, and wherein inner and outer walls of the tube are coated with a metallic layer having a thickness between 1 and 10 skin depths at the frequency of the microwave energy.

11. The plasma sterilization apparatus according to claim 10, wherein the dielectric material is solid polytetrafluoroethylene (PTFE) having a loss factor between 0.0001 and 0.0008 at a frequency of 2.45 GHz.

* * * * *